United States Patent
Blanchette et al.

(10) Patent No.: US 9,895,365 B2
(45) Date of Patent: Feb. 20, 2018

(54) COMBINATION THERAPY FOR CANCER TREATMENT

(71) Applicant: Ipsen Biopharm Ltd., Wrexham (GB)

(72) Inventors: Sarah F. Blanchette, Lynnfield, MA (US); Daryl C. Drummond, Lincoln, MA (US); Jonathan Basil Fitzgerald, Arlington, MA (US); Victor Moyo, Ringoes, NJ (US)

(73) Assignee: Ispen Biopharm Ltd., Wrexham (GB)

( * ) Notice: Subject to any disclaimer, the term of this patent is extended or adjusted under 35 U.S.C. 154(b) by 0 days.

(21) Appl. No.: 15/337,274

(22) Filed: Oct. 28, 2016

(65) Prior Publication Data

US 2017/0049767 A1 Feb. 23, 2017

Related U.S. Application Data

(63) Continuation of application No. PCT/US2016/047827, filed on Aug. 19, 2016.
(Continued)

(51) Int. Cl.
*A61K 31/454* (2006.01)
*A61K 31/4745* (2006.01)
(Continued)

(52) U.S. Cl.
CPC ........ *A61K 31/4745* (2013.01); *A61K 9/0019* (2013.01); *A61K 9/127* (2013.01);
(Continued)

(58) Field of Classification Search
CPC .................................................... A61K 31/454
See application file for complete search history.

(56) References Cited

U.S. PATENT DOCUMENTS

2007/0265324 A1 11/2007 Wernet et al.
2009/0123419 A1 5/2009 Sherman et al.
(Continued)

FOREIGN PATENT DOCUMENTS

WO 2006110816 A2 10/2006

OTHER PUBLICATIONS

Messerer et al (Ciln Can Rsch, Oct. 2004, vol. 10, No. 19, pp. 6638-6649).*
(Continued)

*Primary Examiner* — Benjamin Packard
(74) *Attorney, Agent, or Firm* — Honigman Miller Schwartz and Cohn LLP; Cynthia M. Bott; Jonathan P. O'Brien

(57) ABSTRACT

Combination therapies for treating cancer comprising administration of a topoisomerase-1 inhibitor and a PARP inhibitor are provided. The topoisomerase-1 inhibitor can be delivered as a liposomal formulation that provides for prolonged accumulation of the topoisomerase-1 inhibitor within a tumor relative to outside of the tumor. Therapeutic benefit can thereby be obtained by delaying the administration of the PARP inhibitor after each administration of a liposomal irinotecan formulation until the accumulation of the topoisomerase inhibitor in the tumor is sufficiently greater than outside the tumor to result in increased efficacy of the PARP inhibitor and topoisomerase inhibitor within the tumor, while reducing the peripheral toxicity of the combination therapy. The therapies disclosed herein are useful in the treatment of human cancers with solid tumors, including cervical cancer.

20 Claims, 30 Drawing Sheets

Related U.S. Application Data

(60) Provisional application No. 62/323,422, filed on Apr. 15, 2016, provisional application No. 62/308,924, filed on Mar. 16, 2016, provisional application No. 62/269,511, filed on Dec. 18, 2015, provisional application No. 62/269,756, filed on Dec. 18, 2015, provisional application No. 62/207,709, filed on Aug. 20, 2015, provisional application No. 62/207,760, filed on Aug. 20, 2015.

(51) Int. Cl.

| | | |
|---|---|---|
| *A61K 47/06* | (2006.01) | |
| *A61K 9/127* | (2006.01) | |
| *A61K 31/436* | (2006.01) | |
| *A61K 31/04* | (2006.01) | |
| *A61K 31/166* | (2006.01) | |
| *A61K 31/416* | (2006.01) | |
| *A61K 31/4184* | (2006.01) | |
| *A61K 31/475* | (2006.01) | |
| *A61K 31/502* | (2006.01) | |
| *A61K 31/55* | (2006.01) | |
| *A61K 9/00* | (2006.01) | |
| *A61K 31/5025* | (2006.01) | |
| *A61K 45/06* | (2006.01) | |

(52) U.S. Cl.
CPC ............ *A61K 31/04* (2013.01); *A61K 31/166* (2013.01); *A61K 31/416* (2013.01); *A61K 31/4184* (2013.01); *A61K 31/436* (2013.01); *A61K 31/454* (2013.01); *A61K 31/475* (2013.01); *A61K 31/502* (2013.01); *A61K 31/5025* (2013.01); *A61K 31/55* (2013.01); *A61K 45/06* (2013.01); *A61K 47/06* (2013.01)

(56) References Cited

U.S. PATENT DOCUMENTS

| | | |
|---|---|---|
| 2009/0149397 A1 | 6/2009 | Ossovskaya et al. |
| 2012/0045524 A1 | 2/2012 | Wernet et al. |
| 2016/0206615 A1 | 7/2016 | Tangutoori et al. |

OTHER PUBLICATIONS

Genther-Williams et al (Cancer Cell Intrl, 2015, 15:14, pp. 1-11).*

Znojek, P. et al. "Preferential Potentiation of Topoisomerase I Poison cytotoxicity by PARP Inhibition in S Phase", British Journal of Cancer (2014) vol. 111, pp. 1319-1326; doi: 10.1038/bjc.2014.378.

Tahara, M. et al., "The Use of Olaparib (AZD2281) Potentiates SN-38 Cytotoxicity in Colon Cancer Cells by Indirect Inhibition of Rad51-Mediated Repair of DNA Double-Strand Breaks", Molecular Cancer Therapeutics; 13(5) May 2014, pp. 1170-1180.

Murai, J. et al., "Rationale for Poly(ADP-ribose) Ploymerase (PARP) Inhibitors in Combination Therapy with Campothecins or Temozolomide Based on PARP Trapping versus Catalytic Inhibition", The Journal of Pharmacology and Experimental Therapeutics; 349:408-416 (Jun. 2014).

Kalra, Ashish V., et al., "Preclinical Activity of Nanoliposomal Irinotecan Is Governed by Tumor Deposition and Intratumor Prodrug Conversion", Cancer Research; Published OnlineFirst Oct. 1, 2014; DOI: 10.1158/0008-5472.CAN-14-0572, 12 pages.

Kalra, Ashish V., et al. "Preclinical activity of nanoliposomal irinotencan Is governed by tumor deposition and intratumor prodrug conversion", Cancer Research; Author Manuscript Published OnlineFirst Oct. 1, 2014; DOI: 10.1158/0008-5472.CAN-14-0572, 31 pages.

Koshkaryev, Alexander, et al., Differential Tissue Clearance Results in Improved Therapeutic Index for Nanoliposomal Irinotecan (nal-IRI; Onivyde) when Combined with the PARP inhibitor veliparib; Poster presented at AACR Meeting on Apr. 16-20, 2016.

Alagoz, M., et al., "DNA Repair and Resistance to Topoisomerase I Inhibitors: Mechanisms, Biomarkers and Therapeutic Targets", Current Medicinal Chemistry, 2012, vol. 19, pp. 3874-3885.

Davidson, David, et al., "The PARP inhibitor ABT-888 synergizes irinotecan treatment of colon cancer cell lines", Invest New Drugs; DOI: 10.1007/s10637-012-9886-7; Published online: Oct. 9, 2012, 8 pages.

Gilbert, D.C., et al., "Topoisomerase I inhibition in colorectal cancer: biomarkers and therapeutic targets", British Journal of Cancer (2012) 106(1), pp. 18-24.

Lo Russo, Patricia M., et al., Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors; Clinical Cancer Research (2016) pp. 3227-3237; DOI: 10.1158/1078-0432.CCR-15-0652.

Murai, Junko, et al., "Identification of novel PARP inhibitors using a cell-based TDP1 inhibitory assay in a quantitative high-throughput screening platform" Author manuscript; Published in final edited form as: DNA Repair (Amst). Sep. 2014; 21:177-182; DOI: 10.1016/j.dnarep.2014.03.006, pp. 1-13.

Tentori, Lucio, et al. "Influence of MLH1 on colon cancer sensitivity to poly(ADP-ribose) polymerase inhibitor combined with irinotecan", Internal Journal of Oncology 43; 210-218, 2013.

Zander, Serge A., et al. EZN-2208 (PEG-SN38) Overcomes ABCG2-Mediated Topotecan Resistance in BRCA1-Deficient Mouse Mammary Tumors, PLOS One, Sep. 2012, vol. 7, Issue 9, pp. 1-9.

Zhang, Yong-Wei, et al. "Poly(ADP-ribose) polymerase and XPF-ERCC1 participate in distinct pathways for the repair of topoisomerase I-induced DNA damage in mammalian cells", Nucleic Acids Research, 2011, vol. 39, No. 9, pp. 3607-3620; DOI: 10.1093/nar/gkq1304; Published online Jan. 11, 2011.

LYNPARZA™ (olaparib) capsules Prescribing Information, © AstraZeneca 2014; Revised: Dec. 2014; 6 pages.

Clinical Trials Archive: "Liposomal Irinotecan and Veliparib in Treating Patients with Solid Tumors That Are Metastatic or Cannot be Removed by Surgery", NCT02631733, Updated: Dec. 15, 2015, Retrieved from the Internet: https://clinicaltrials.gov/archive/NCT02631733/2015_12_15, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Feb. 16, 2016, Retrieved from the Internet: https://clinicaltrials.gov/archive/NCT02631733/2016_02_16, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jun. 20, 2016, Retrieved from the Internet: https://clinicaltrials.gov/archive/NCT02631733/2016_06_20, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jun. 21, 2016, Retrieved from the Internet: https://clinicaltrials.gov/archive/NCT02631733/2016_06_21, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 6, 2016, Retrieved from the Internet: https://clinicaltrials.gov/archive/NCT02631733/2016_07_06, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 11, 2016, Retrieved from the Internet: https://clinicaltrials.gov/archive/NCT02631733/2016_07_11, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Jul. 19, 2016, Retrieved from the Internet: https://clinicaltrials.gov/archive/NCT02631733/2016_07_19, pp. 1-6.

(56) References Cited

OTHER PUBLICATIONS

Clinical Trials Archive: "Liposomal Irinotecan and Veliparib in Treating Patients With Solid Tumors That Are Metastatic or Cannot Be Removed by Surgery", NCT02631733, Updated: Aug. 7, 2016, Retrieved from the Internet: https://clinicaltrials.gov/archive/NCT02631733/2016_08_07, pp. 1-6.

Clinical Trials Archive: "Liposomal Irinotecan and Veliparib in Treating Patients With Solid Tumors That Are Metastatic or Cannot Be Removed by Surgery", NCT02631733, Updated: Sep. 21, 2016, Retrieved from the Internet: https://clinicaltrials.gov/archive/NCT02631733/2016_09_21, pp. 1-6.

Douillard J. et al, "Irinotecan Combined With Fluorouracil Compared with Fluorouracil Alone as First-Line Treatment for Metastatic Colorectal Cancer: A Multicentre Randomised Trial," The Lancet, 2000, pp. 1041-1047, vol. 355, No. 9209.

Hare Jennifer I et al., "Treatment of Colorectal Cancer Using a Combination of Liposomal Irinotecan (Irinophore C(TM)) and 5-Fluorouracil," PLOS ONE, 2013, pp. 1-12, vol. 8, No. 4, E62349.

PCT/US2016/047814 International Search Report, dated Nov. 17, 2016, 3 pages.

PCT/US2016/047827 International Search Report, dated Nov. 17, 2016, 3 pages.

\* cited by examiner

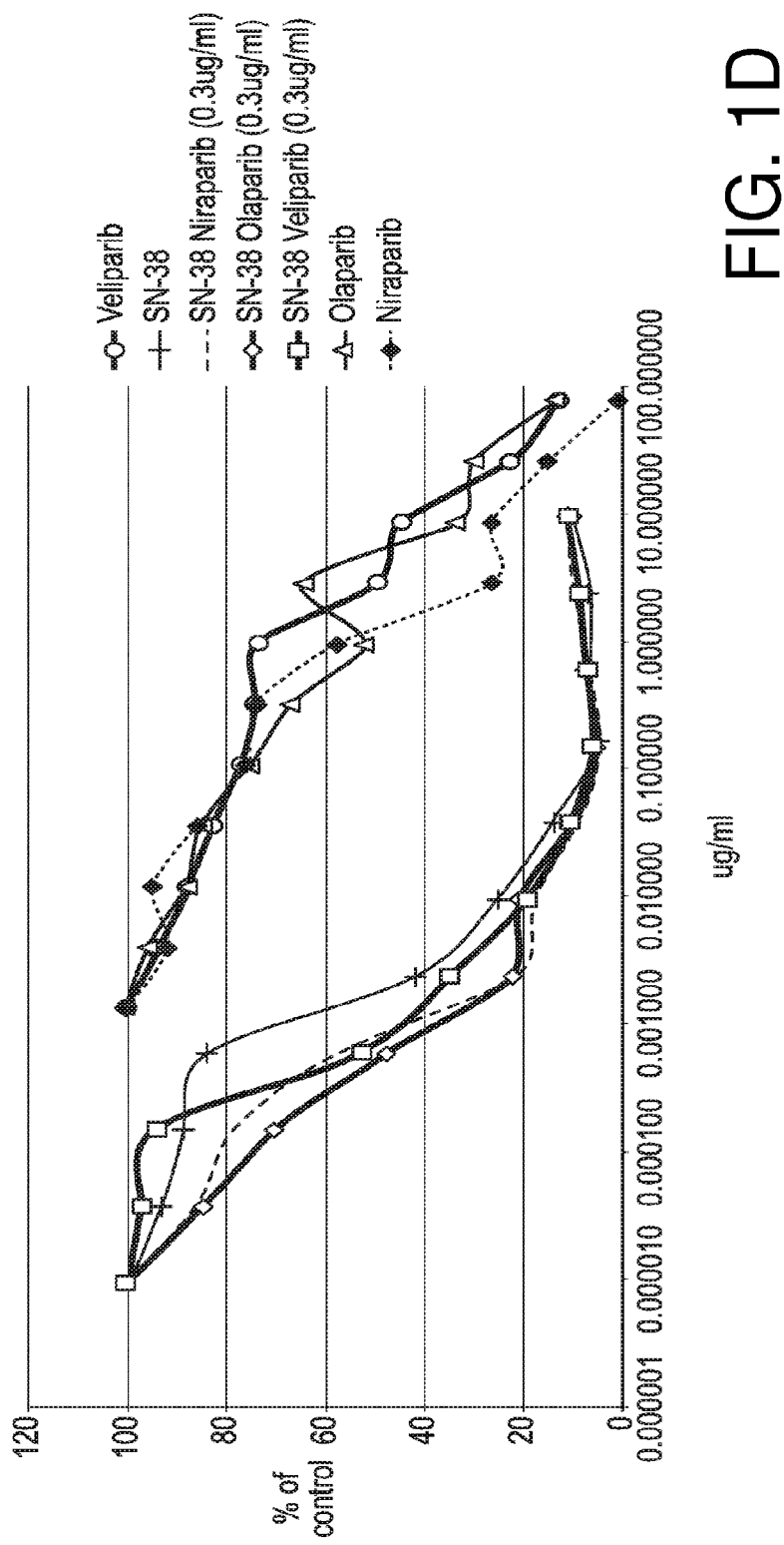

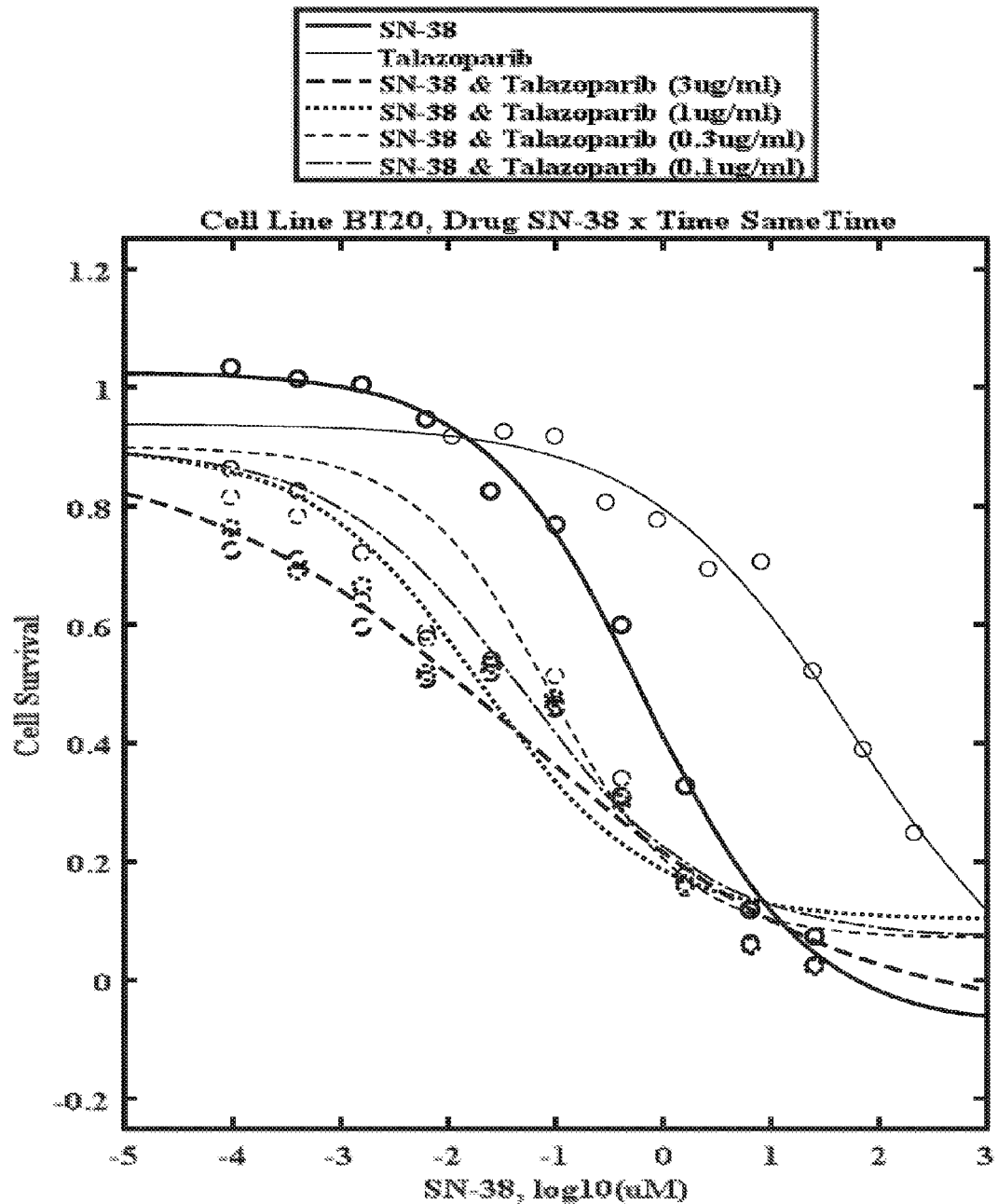

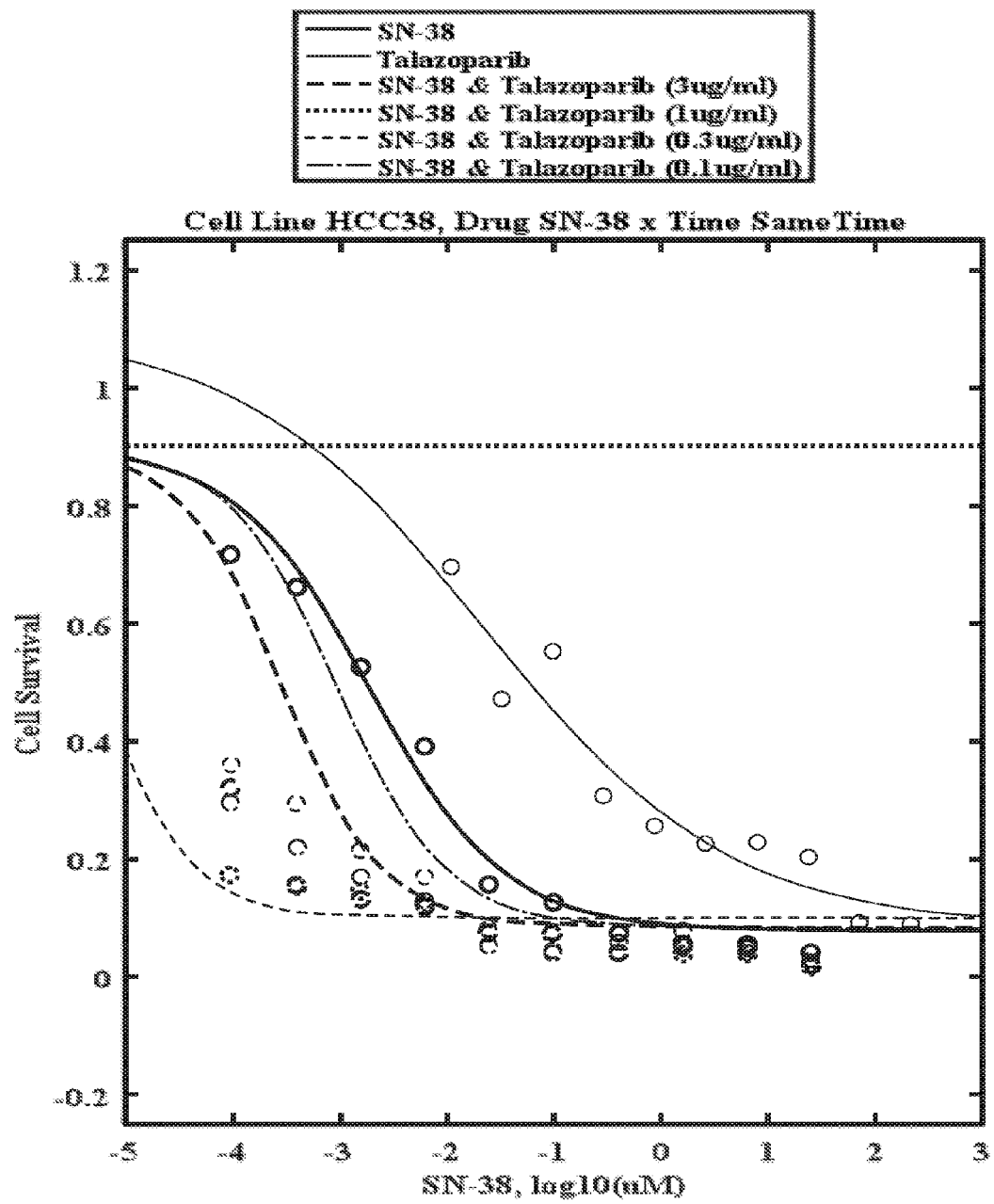

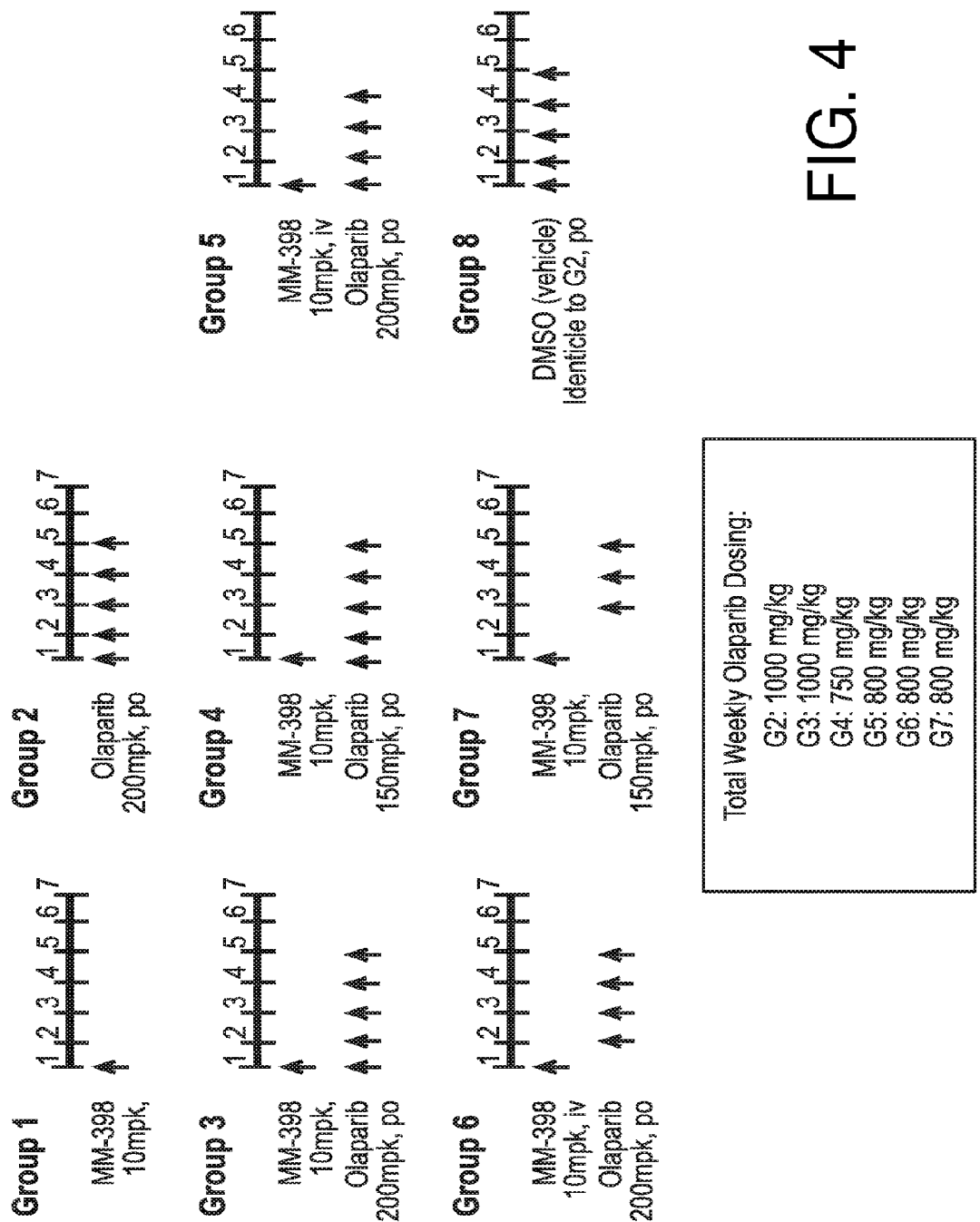

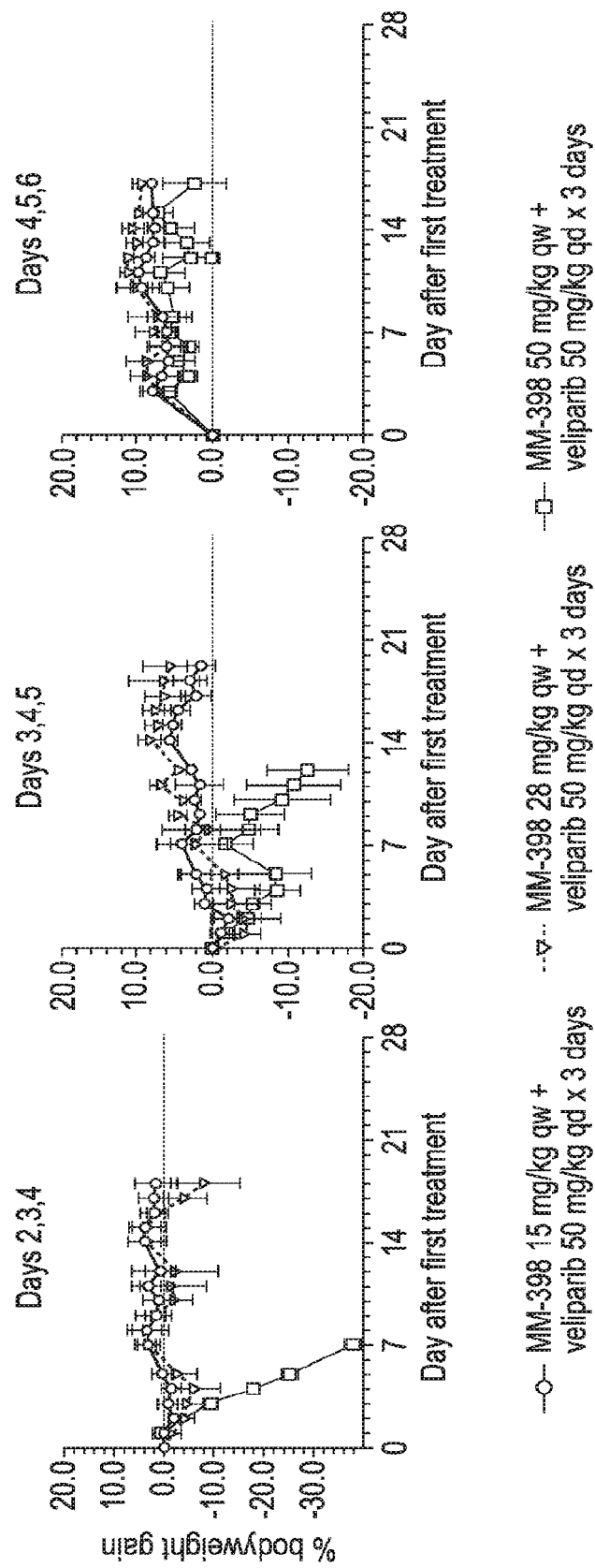

COMBINATION THERAPY FOR CANCER TREATMENT

CROSS-REFERENCE TO RELATED APPLICATIONS

This application is a continuation of PCT No.: PCT/US2016/047827, filed on Aug. 19, 2016, which claims the benefit of priority under 35 U.S.C. §119 to U.S. Provisional Application Ser. Nos. 62/323,422, filed on Apr. 15, 2016, 62/308,924, filed on Mar. 16, 2016, 62/269,511, filed on Dec. 18, 2015, 62/269,756, filed on Dec. 18, 2015, 62/207,709, filed on Aug. 20, 2015, and 62/207,760, filed on Aug. 20, 2015. The contents of each of the foregoing applications are incorporated herein by reference in their entirety.

TECHNICAL FIELD

This invention relates to the treatment of cancer with a Poly(ADP-ribose) polymerase (PARP) inhibitor and a topoisomerase inhibitor.

BACKGROUND

Liposomal irinotecan and PARP inhibitors are therapies useful in the treatment of cancer. Liposome encapsulated irinotecan formulations of the topoisomerase inhibitor irinotecan provide sustained exposure of irinotecan and the metabolite SN-38 in a tumor. ONIVYDE (irinotecan liposome injection) is an example of liposomal irinotecan recently approved in the United States for the treatment of patients with metastatic adenocarcinoma of the pancreas after disease progression following gemcitabine-based therapy. Poly(ADP-ribose) polymerases are a family of enzymes involved in DNA repair believed to act via two mechanisms: catalytic inhibition and trapping of PARP-DNA complexes, and inhibition of this repair pathway can result in cell death following DNA damage. PARP inhibitors are a new class of chemotherapeutic agents currently in development for the treatment of various cancer types.

While certain combinations of PARP and topoisomerase inhibitors have shown to be synergistic in in vitro assays, the clinical development of PARP inhibitor and topoisomerase inhibitor combinations has been limited due to increased toxicities and resultant dose reductions, thereby limiting the potential clinical utility of the combination. For example, significant myelosuppression was seen in a dose-escalation study of veliparib and topotecan, wherein the maximum tolerated dose was exceeded at the first planned dose level. Most PARP inhibitors are being developed to date solely as monotherapies. As a result, there is a need for methods to safely and effectively combine a PARP inhibitor with a Top1 inhibitor to treat cancer.

SUMMARY

The present disclosure provides methods of treating cancer by administering a topoisomerase inhibitor and a PARP inhibitor with reduced peripheral toxicity. This can be accomplished by administering the topoisomerase inhibitor in a form (e.g., liposomal irinotecan) that prolongs accumulation of the topoisomerase inhibitor in a tumor relative to sites outside the tumor, and then subsequently administering the PARP inhibitor(s) to the patient after an interval between the administration of the topoisomerase inhibitor and the PARP inhibitor. The interval can be selected to provide enough time for the topoisomerase inhibitor (e.g., irinotecan and/or its metabolite SN-38) to clear plasma or tissue outside of the tumor to a greater extent than inside the tumor. Preferably, the interval is an effective topoisomerase-1 inhibitor plasma clearing interval. As used herein, the term "effective topoisomerase-1 inhibitor plasma clearing interval" (e.g., irinotecan plasma clearing interval) is that interval between concluding the administration of a topoisomerase-1 inhibitor formulation (e.g., liposomal irinotecan) and initiating the administration of one or more PARP inhibitors, where the time interval is selected to allow sufficient clearance of the topoisomerase-1 inhibitor (e.g., irinotecan or its active metabolite SN-38) from the blood plasma (or peripheral tissue) but allows an effective quantity of the topoisomerase-1 inhibitor (e.g., irinotecan and/or SN38) to remain in one or more tumors within the patient during the subsequent administration of the PARP inhibitor in an amount effective to provide a desired effect on the tumor (e.g., heightened combined toxicity localized within the tumor). Preferably, the PARP inhibitor is administered after an irinotecan plasma clearing interval of 3-5 days (e.g., 3, 4 or 5 days) after completing the administration of liposomal irinotecan on days 1 and 15 during each of one or more 28-day treatment cycles.

Methods of treating cancer disclosed herein include the treatment of solid tumors. In certain examples, the cancer treated can be selected from the group consisting of cervical cancer, ovarian cancer, triple negative breast cancer, non-small cell lung cancer, small cell lung cancer, gastrointestinal stromal tumors gastric cancer, pancreatic cancer, colorectal cancer, and a neuroendocrine cancer. Preferably, the cancer is cervical cancer.

The topoisomerase inhibitor can be provided as a liposome formulation. Preferably, the topoisomerase inhibitor is a liposomal irinotecan. The liposomal irinotecan can provide an irinotecan terminal elimination half-life of 26.8 hours and a maximal irinotecan plasma concentration of 38.0 micrograms/ml. In some examples, the liposomal irinotecan can include irinotecan sucrose octasulfate encapsulated within phospholipid vesicles having a size of about 110 nm. For example, the liposomal irinotecan can be the product ONIVYDE® (irinotecan liposome injection) (Merrimack Pharmaceuticals, Inc, Cambridge, Mass.), previously designated "MM-398." The PARP inhibitor can include one or more compounds selected from the group consisting of niraparib, olaparib, veliparib, and rucaparib, preferably veliparib or olaparib.

The topoisomerase-1 inhibitor is preferably a liposomal irinotecan (e.g., MM-398), which can be administered at dose of 80 mg/m$^2$ (salt) irinotecan once every 2 weeks in combination with a PARP inhibitor (e.g., veliparib, olaparib, niraparib or rucaparib) administered daily during each two week cycle starting 3-5 days after administration of liposomal irinotecan without administering the PARP inhibitor on days when the liposomal irinotecan is administered (e.g., without administering the PARP inhibitor 1, 2 or 3 days before the next liposomal irinotecan administration). Preferably, the PARP inhibitor is not administered within 3 days of (i.e., neither 3 days after nor 3 days before) the administration of liposomal irinotecan.

Specific methods of treating a cancer provided herein include administering an antineoplastic therapy consisting of the administration of liposomal irinotecan every 2 weeks (e.g., on days 1 and 15 of a 28-day treatment cycle), and the administration of a PARP inhibitor one or more times per day (e.g., twice per day) for one or more days (e.g., 7-9 days) starting at least 3 days (e.g., 3, 4 or 5 days) after each administration of the liposomal irinotecan, without administering other antineoplastic agents during the antineoplastic therapy. For example, one antineoplastic therapy is a 28-day treatment cycle consisting of: administering 70 mg/m² MM-398 liposomal irinotecan (free base) on days 1 and 15, and administering a therapeutically effective amount of the PARP inhibitor (e.g., 50-400 mg twice per day for veliparib) on each of days 5-12 and days 19-25 of the treatment cycle, where no other antineoplastic agent is administered during the treatment cycle. Another antineoplastic therapy is a 28-day treatment cycle consisting of: administering 70 mg/m² MM-398 liposomal irinotecan (free base) on days 1 and 15, and administering a therapeutically effective amount of the PARP inhibitor (e.g., 50-400 mg twice per day for veliparib) on each of days 3-12 and days 17-25 of the treatment cycle, where no other antineoplastic agent is administered during the treatment cycle.

In some examples, liposomal irinotecan and a PARP inhibitor can be combined in an antineoplastic therapy for the treatment of a solid tumor, comprising a 28-day antineoplastic therapy treatment cycle consisting of: administering the liposomal irinotecan on days 1 and 15 of the treatment cycle, and administering the PARP inhibitor on one or more days starting at least 3 days after the liposomal irinotecan and ending at least 1 day prior to administration of additional liposomal irinotecan. In some examples, the PARP inhibitor is not administered for at least 3 days after the administration of liposomal irinotecan. For example, the PARP inhibitor can be administered on one or more of days 5-12 of the antineoplastic therapy treatment cycle, and administered on one or more of days 19-25 of the antineoplastic therapy treatment cycle. In some examples, the PARP inhibitor is administered on one or more of days 3-12 of the antineoplastic therapy treatment cycle, and administered on one or more of days 17-25 of the antineoplastic therapy treatment cycle. In some examples, the PARP inhibitor is not administered within 3 days before or after the administration of the liposomal irinotecan.

In addition, therapeutically effective doses of the topoisomerase inhibitor and PARP inhibitor compounds are provided herein. In some examples, each administration of liposomal irinotecan is administered at a dose of 80 mg/m² (salt) of MM-398. In some examples, each administration of the PARP inhibitor is administered at a dose of from about 20 mg/day to about 800 mg/day. Each administration of the PARP inhibitor can be administered once or twice daily at a dose of from about 20 mg/day to about 400 mg/day.

BRIEF DESCRIPTION OF THE DRAWINGS

FIG. 1D is a graph showing the results of a cell viability in vitro measurement of SW756 human cervical cancer cells treated with the topoisomerase 1 inhibitor SN-38 and various PARP inhibitors.

FIG. 3A is a graph showing the results of in vitro measurement of cell survival for BT-20 triple negative breast cancer (TNBC) cancer cells treated with the topoisomerase inhibitor SN-38 and the PARP inhibitor talazoparib.

FIG. 3B is a graph showing the results of in vitro measurement of cell survival for HCC38 triple negative breast cancer (TNBC) cancer cells treated with the topoisomerase inhibitor SN-38 and the PARP inhibitor talazoparib.

FIG. 4 depicts a graphical representation of a murine tolerability study design comparing MM-398 and olaparib as a monotherapy or in combination using a fixed dose of MM-398 and varying doses of olaparib, with various dosing schedules for different groups.

FIG. 5A is a graph showing the results of a murine tolerability study of a combination of MM-398 and veliparib, measuring % change in bodyweight after administration of 15 mg/kg of MM-398 on day 1, and 50 mg/kg of veliparib on days 2, 3, and 4.

FIG. 5B is a graph showing the results of a murine tolerability study of a combination of MM-398 and veliparib, measuring % change in bodyweight after administration of 28 mg/kg of MM-398 on day 1, and 50 mg/kg of veliparib on days 3, 4, and 5.

FIG. 5C is a graph showing the results of a murine tolerability study of a combination of MM-398 and veliparib, measuring % change in bodyweight after administration of 50 mg/kg of MM-398 on day 1, and 50 mg/kg of veliparib on days 4, 5, and 6.

DETAILED DESCRIPTION

Figure 1A:
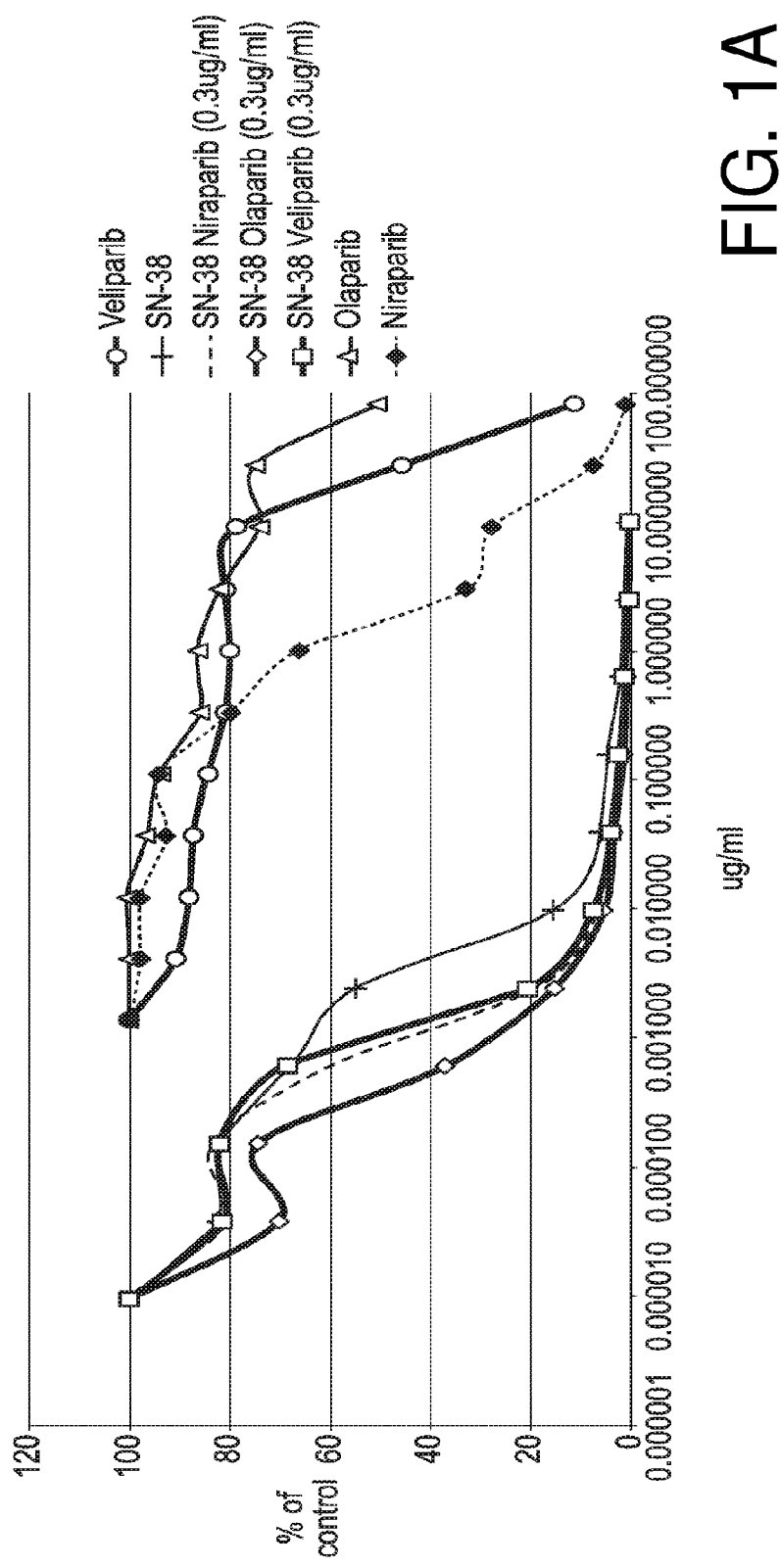
FIG. 1A is a graph showing the results of a cell viability in vitro measurement of ME-180 human cervical cancer cells treated with the topoisomerase 1 inhibitor SN-38 and various PARP inhibitors.
Figure 1B:
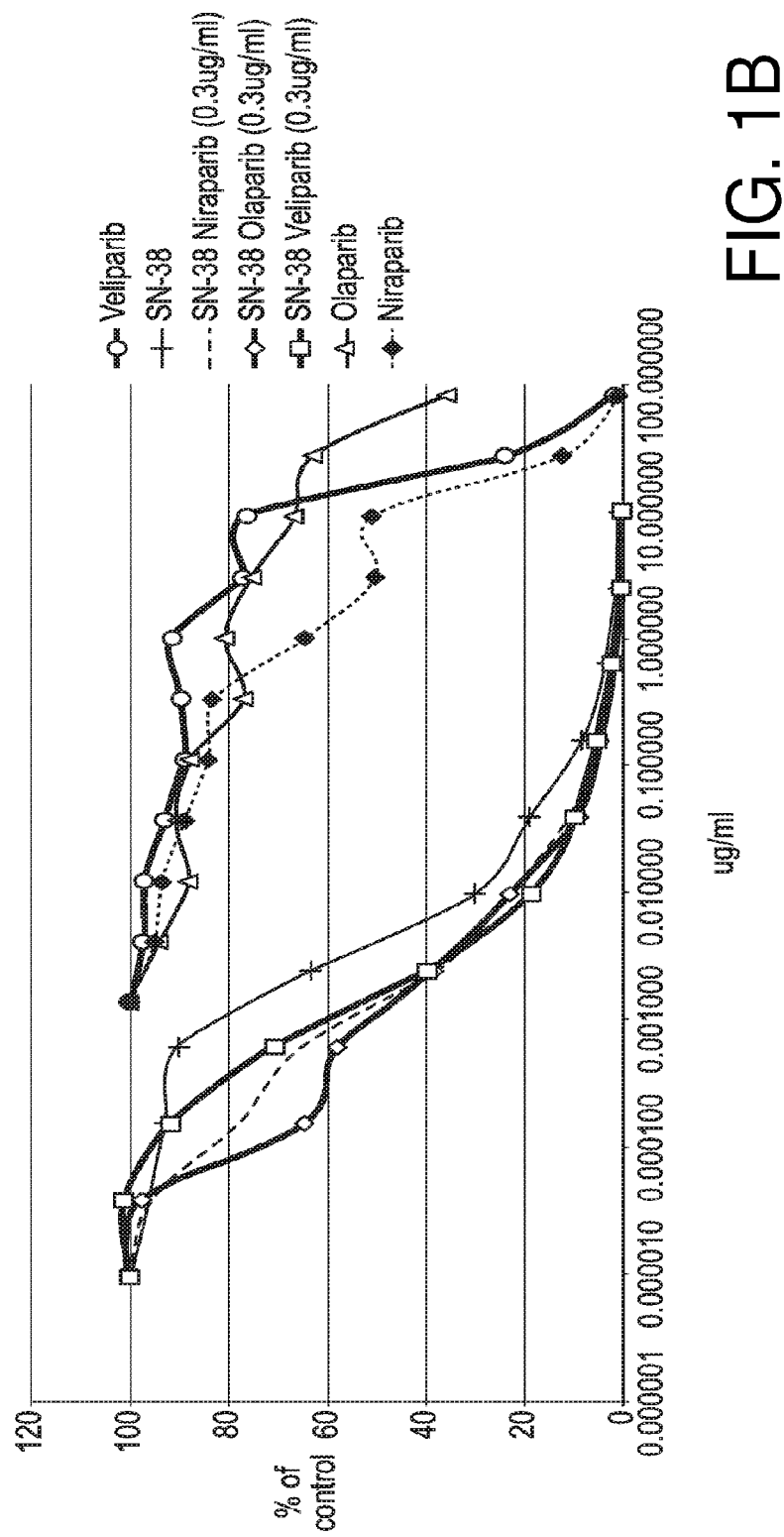
FIG. 1B is a graph showing the results of a cell viability in vitro measurement of MS-751 human cervical cancer cells treated with the topoisomerase 1 inhibitor SN-38 and various PARP inhibitors.
Figure 1C:
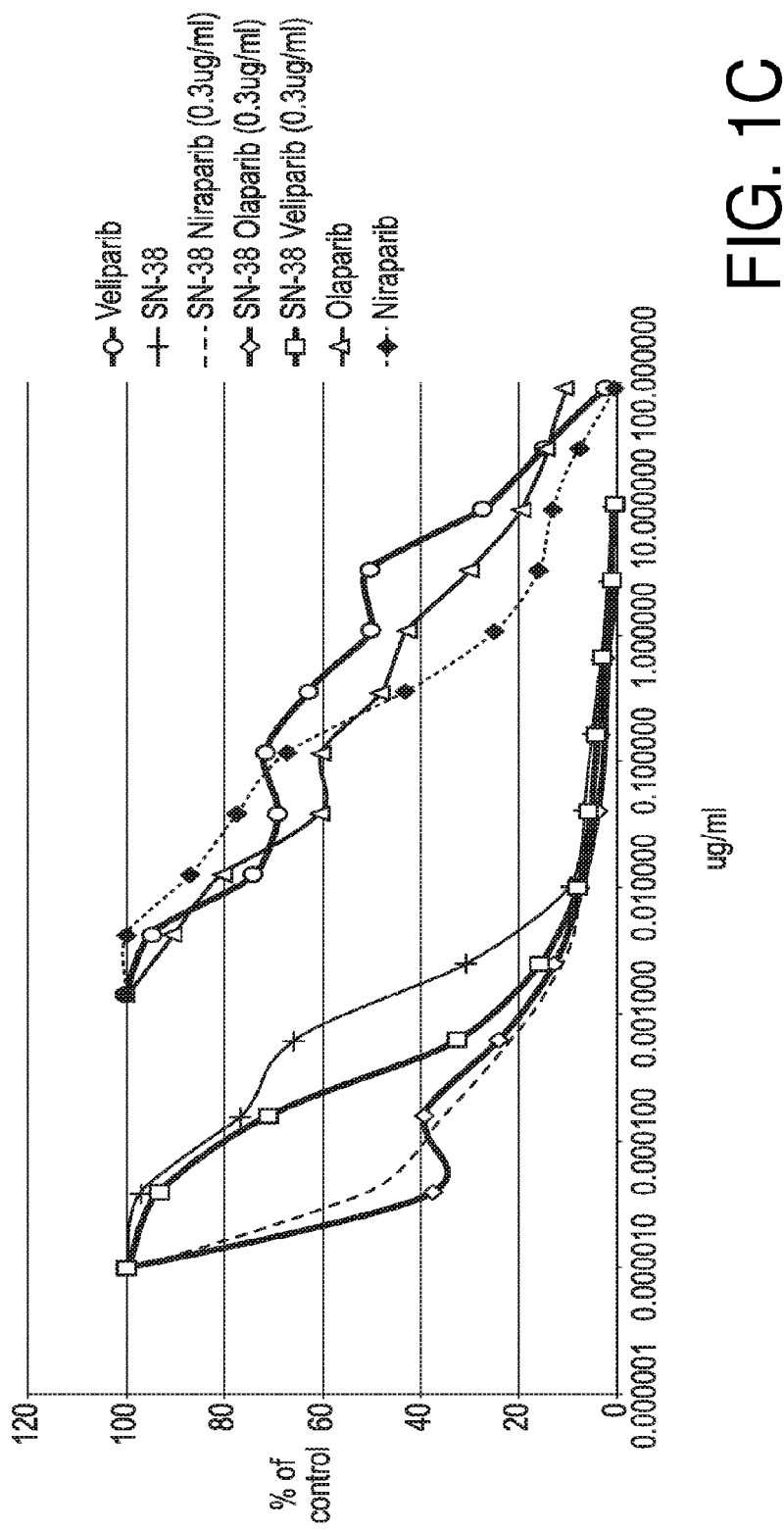
FIG. 1C is a graph showing the results of a cell viability in vitro measurement of C-33A human cervical cancer cells treated with the topoisomerase 1 inhibitor SN-38 and various PARP inhibitors.
Figure 1E:
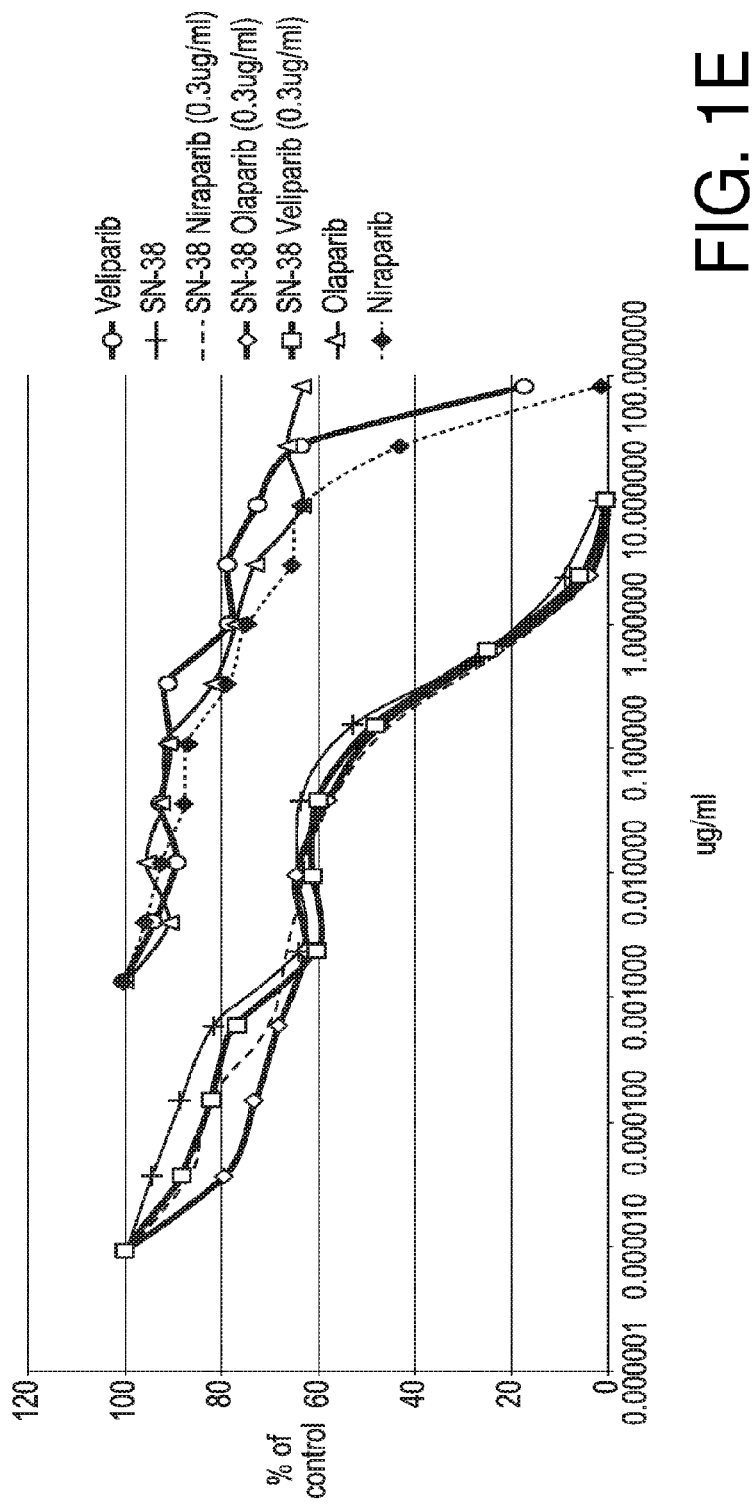
FIG. 1E is a graph showing the results of a cell viability in vitro measurement of SiHa human cervical cancer cells treated with the topoisomerase 1 inhibitor SN-38 and various PARP inhibitors.

The present disclosure provides for methods of administering a combination of a topoisomerase-1 (Top1) inhibitor (e.g., irinotecan and/or its metabolite SN-38) and a PARP inhibitor to a tumor with reduced peripheral toxicity. The Top1 inhibitor can be administered in a liposome formulation resulting in the prolonged accumulation of the Top1 inhibitor in a solid tumor compared to peripheral plasma and/or healthy organs. Subsequently, a PARP inhibitor can be administered after a period of time permitting a reduction in the amount of the Top1 inhibitor outside the tumor relative to the amount of Top1 inhibitor within the tumor. Preferably, the Top1 inhibitor is administered as a liposomal irinotecan that provides SN-38 to a solid tumor.

Methods of treating a cancer are provided, as well as therapeutic uses of PARP inhibitor compounds in combination with liposomal irinotecan formulations for the treatment of cancer, particularly cancer comprising solid tumors. These uses and methods can provide a treatment regimen comprising: (a) administering to a patient in need thereof an effective amount of an irinotecan liposomal formulation; and (b) after completion of the administration of the Top1 inhibitor, administering to the patient an effective amount of a PARP inhibitor, wherein the PARP inhibitor is administered to the patient following an interval that allows for a reduction in peripheral toxicity as compared to simultaneous administration of the Top1 inhibitor and the PARP inhibitor. The interval can be selected to provide time for sufficient clearance of the Top1 inhibitor (e.g., either or both of irinotecan and SN-38) from the blood plasma to avoid peripheral toxicity due to the synergistic toxic effects of the combination of Top1 inhibitor and PARP inhibitor, while allowing an effective quantity of Top1 inhibitor to remain in one or more tumors within the patient for the subsequent administration of the PARP inhibitor to have a desired synergistic therapeutic effect. This treatment regimen can preferably provide one or more attributes, which may include increased efficacy of the combination as compared to single agent treatment; reduced side effects, dosing the drugs at a higher dose compared with administration of the combination of a PARP inhibitor and a non-liposomal Top1 inhibitor.

The uses and methods disclosed herein are based in part on experiments evaluating the combination of a topoisomerase 1 inhibitor (e.g., liposomal irinotecan or SN-38) and a PARP inhibitor in both pre-clinical and human clinical studies. The topoisomerase 1 inhibitor was administered in certain in vitro animal models using a formulation delivering a more prolonged exposure of the topoisomerase 1 inhibitor (e.g., irinotecan and/or the irinotecan active metabolite designated SN-38) within solid tumors than in peripheral tissue and plasma outside the tumor. Combinations of the topoisomerase 1 inhibitor SN38 and/or irinotecan and PARP inhibitor compounds were tested in various in vitro experiments. As detailed in Example 1, the in vitro testing of multiple combinations of a topoisomerase 1 inhibitor (SN38) and various PARP inhibitors in more than 20 different cancer cell lines (including cervical, breast, ovarian, colorectal, pancreatic, and small cell lung cancer cell lines) all demonstrated decreased cancer cell line viability (FIGS. 1A, 1B, 1C, 1D, 1E, 2A, 2B, 2C, 2D, 2E, and 13A). The liposomal irinotecan (MM398) demonstrated greater tumor volume reduction than non-liposomal (free) irinotecan (CPT11) in mouse xenograft studies across multiple types of cancer cell lines (including breast, ovarian, colorectal and pancreatic cancer cell lines).

As detailed in Example 2, the tolerability of a topoisomerase 1 inhibitor (liposomal irinotecan) administered in combination with various PARP inhibitors was evaluated by measuring the change in animal (mouse) body weight in multiple murine models by comparing various dosing schedules. In some experiments, both liposomal irinotecan and a PARP inhibitor were administered together on the same day (day 1). In other experiments, the PARP inhibitor was first administered daily starting 2, 3 or 4 days after each administration of the liposomal irinotecan. The PARP inhibitor was administered for multiple consecutive days (e.g., 3 consecutive days), and not administered on the same day as the topoisomerase 1 inhibitor. As detailed in multiple experiments herein, administration of the PARP inhibitor at least one day after the liposomal irinotecan resulted in improved tolerability of comparable combined doses of the PARP inhibitor and liposomal irinotecan (MM-398) as measured by change in percent bodyweight in the animal (e.g., FIGS. 6A, 6B, 6C, 6D, 8A, and 8B). Delaying the administration of the PARP inhibitor 2, 3 or 4 days after administration of the liposomal irinotecan led to greater overall tolerability of a combined administration of the liposomal irinotecan and the PARP inhibitor, compared to the administration of the liposomal irinotecan and the PARP inhibitor on the same day. For example, administration of veliparib on days 2, 3 and 4 after administration of liposomal irinotecan on day 1 resulted in successively increased tolerability (measured as higher percent mouse bodyweight) of the combination of these two drugs (observed at 15 mg/kg liposomal irinotecan dose on day 1 followed by veliparib dosing on days 2, 3 and 4 (FIG. 5A); at 28 mg/kg liposomal irinotecan dosage on day 1 followed by veliparib dosing on days 3, 4, and 5 (FIGS. 5B and 8B), or followed by veliparib dosing on days 2, 3 and 4 (FIG. 8B); and at 50 mg/kg liposomal irinotecan dose on day 1 followed by veliparib dosing on days 4, 5 and 6 (FIG. 5C), or followed by veliparib dosing on days 2, 3 and 4 or followed by veliparib dosing on days 3, 4, and 5 (FIG. 8A)). Similarly, administering olaparib starting on days 2 or 3 after MM398 resulted in comparable or improved tolerability compared to administration of both agents on day 1. For example, administering a 200 mg/kg dose of olaparib to mice on days 2, 3, 4 and 5 after administration of 10 mg/kg MM398 liposomal irinotecan on day 1 resulted in a lower reduction in bodyweight than administering the same doses of both MM398 and olaparib on days 1, 2, 3 and 4.

Combinations of a topoisomerase 1 inhibitor (SN38 and/or irinotecan) and PARP inhibitor compounds were tested in various preclinical in vivo experiments to evaluate the effectiveness of the administration of various PARP inhibitors starting 3 or 4 days after administration of the liposomal topoisomerase 1 inhibitor MM398. As detailed in Example 3, the administration of liposomal irinotecan (MM398) on day 1 followed by the PARP inhibitor veliparib on either days 3, 4 and 5 or days 4, 5, and 6, resulted in decreased tumor volume and extended percent survival in mouse xenograft models of cervical cancer using two different cell lines (MS751 and C33A) (FIGS. 7A, 7B, 9A, 9B, 10 and 11).

Based in part on these experiments, methods of treating human cancer include the administration of a PARP inhibitor one or more days (preferably 2, 3, 4, 5 or 6 days) after the administration of liposomal topoisomerase inhibitor such as liposomal irinotecan. Preferably, the PARP inhibitor and the liposomal irinotecan are not administered on the same day. Example 5 provides preferred embodiments for the use of liposomal irinotecan and one or more PARP inhibitors for the treatment of human cancer, such as cervical cancer, while other embodiments (e.g., Table 3) are also provided.
Topoisomerase Inhibitors, Including Liposomal Irinotecan and Camptothecin Conjugates The topoisomerase inhibitor can be administered in any form that provides for the prolonged retention of a topoisomerase-1 inhibitor activity within a tumor compared to outside the tumor, after administration of the topoisomerase inhibitor. For example, the topoisomerase inhibitor can be a formulation that delivers SN-38 to a tumor cell in vivo, administered in an amount and manner providing a higher concentration of the SN-38 within the tumor than outside the tumor for a period of time after administration of the topoisomerase inhibitor. Suitable formulations of topoisomerase inhibitors include conjugate molecules of a topoisomerase inhibitor (e.g., camptothecin conjugated to a polymer or antibody), liposomes containing a topoisomerase inhibitor or other targeted release formulation technologies. The Top1 inhibitor is preferably formulated to provide prolonged accumulation in a tumor site, compared to accumulation in healthy (non-cancer) tissue outside the tumor site (e.g., in the plasma and/or healthy organs such as colon, duodenum, kidney, liver, lung and spleen). Various Top1 inhibitor liposomal formulations are described in U.S. Pat. No. 8,147,867 and U.S. Patent Application Publication No. 2015/0005354, both of which are incorporated herein by reference.

In one embodiment, the topoisomerase inhibitor is SN-38, camptothecin or a compound that is converted to SN-38 within the body, such as irinotecan. Irinotecan and SN-38 are examples of Top1 inhibitors. Irinotecan is converted by esterase enzymes into the more active metabolite, SN-38. The chemical name of irinotecan is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan hydrochloride trihydrate is also referred to by the name CPT-11 and by the trade name CAMPTOSAR®.

The topoisomerase inhibitor can be camptothecin conjugated to a biocompatible polymer such as a cyclodextrin or cyclodextrin analog (e.g., sulfonated cyclodextrins). For example, the topoisomerase inhibitor can be a cyclodextrin-containing polymer chemically bound to a camptothecin, irinotecan, SN-38 or other topoisomerase 1 inhibitor compound. A cyclodextrin-camptothecin conjugated topoisomerase 1 inhibitor can be administered at a pharmaceutically acceptable dose including 6, 12, or 18 mg/m2 weekly administration, or 12, 15 or 18 mg/m2 biweeekly administration. Examples of camptothecin-cyclodextrin conjugate topoisomerase 1 inhibitors (e.g., the cyclodextrin-containing polymer conjugate with camptothecin designated "CRLX101"), and related intermediates for preparing the same, are disclosed, for example, in Greenwald et al., Bioorg. Med. Chem., 1998, 6, 551-562, as well as United States Patent Application 2010/0247668, United States Patent Application 2011/0160159 and United States Patent Application 2011/0189092

The topoisomerase inhibitor can also be a liposomal formulation of a topoisomerase inhibitor such as irinotecan, camptothecin or topotecan. Liposomal irinotecan (e.g., MM-398, also called "nal-IRI") is a highly stabilized liposomal formulation of irinotecan that provides for sustained exposure of irinotecan, and the active metabolite SN-38 in the tumor to a higher proportion of cells during the more sensitive S-phase of the cell cycle. MM-398 is a liposomal irinotecan that has shown promising preclinical and clinical activity in a range of cancer types, and was recently approved in the United States in combination with 5-FU/LV for patients with metastatic adenocarcinoma of the pancreas after disease progression following gemcitabine-based therapy. Compared with free irinotecan, nal-IRI has an extended PK profile with prolonged local tumor exposure of MM-398 and SN-38. Since SN-38 is cleared more quickly from normal tissues than from tumor, it is hypothesized that delayed dosing of veliparib relative to MM-398 will allow for the expected window of maximum irinotecan-induced toxicity to pass in the absence of concurrent veliparib toxicity. However, the tumor levels of SN-38 are predicted to be sustained upon subsequent veliparib dosing, therefore maintaining the ability of both drugs to act on tumor tissue simultaneously and maintain synergy.

One suitable liposomal Top1 inhibitor formulation is liposomal irinotecan available under the brand name ONIVYDE® (irinotecan liposome injection) (Merrimack Pharmaceuticals, Inc, Cambridge, Mass.), previously designated "MM-398" prior to FDA approval, and liposomal irinotecan products that are bioequivalent to ONIVYDE. The ONIVYDE/MM-398 (irinotecan liposome injection) includes irinotecan as an irinotecan sucrosofate salt encapsulated in liposomes for intravenous use. The drug product liposome is a small unilamellar lipid bilayer vesicle, approximately 110 nm in diameter, which encapsulates an aqueous space which contains irinotecan in a gelated or precipitated state, as the sucrosofate salt. The liposome carriers are composed of 1,2-distearoyl-sn-glycero-3-phosphocholine (DSPC), 6.81 mg/mL; cholesterol, 2.22 mg/mL; and methoxy-terminated polyethylene glycol (MW 2000)-distearoylphosphatidylethanolamine (MPEG-2000-DSPE), 0.12 mg/mL. Each mL also contains 2-[4-(2-hydroxyethyl) piperazin-1-yl]ethanesulfonic acid (HEPES) as a buffer, 4.05 mg/mL; sodium chloride as isotonicity reagent, 8.42 mg/mL. ONIVYDE/MM-398 is believed to include about 80,000 molecules of irinotecan in a gelated or precipitated state as a sucrosofate salt encapsulated in a liposome of about 100 nm in diameter.

As used herein, unless otherwise indicated, the dose of irinotecan in ONIVYDE/MM-398 refers to the dose of irinotecan based on the molecular weight of irinotecan hydrochloride trihydrate (i.e., "(salt)" dose), unless clearly indicated otherwise. Alternatively, the irinotecan dose in ONIVYDE/MM-398 may also be expressed as the irinotecan free base (i.e., "(base)" dose). Converting a dose based on irinotecan (salt) dose to an irinotecan (base) dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, the 80 mg/m$^2$ irinotecan (salt) dose of ONIVYDE/MM-398 refers to the amount of irinotecan based on irinotecan hydrochloride trihydrate, and is equivalent to a 69.60 mg/m$^2$ irinotecan (base) dose of ONIVYDE/MM-398 based on irinotecan free base (80×0.87). In the clinic this is rounded to 70 mg/m$^2$ to minimize any potential dosing errors. Similarly, a clinical dose of 120 mg/m$^2$ (salt) dose of ONIVYDE/MM-398 (based on the corresponding amount of irinotecan hydrochloride trihydrate providing the same amount of irinotecan free base) is equivalent to 100 mg/m$^2$ (base) dose of ONIVYDE/MM-398 (based on the actual amount of irinotecan free base administered in the liposomal irinotecan).

ONIVYDE/MM-398 has been shown to improve the pharmacokinetic and safety profile of the free irinotecan, through high retention of the irinotecan molecules within the liposome, by extending the half-life of irinotecan in the plasma, and increased exposure of tumor cells to irinotecan compared with other organs. Table 1 below provides a summary of median (% IQR)*total irinotecan and SN-38 pharmacokinetic parameters observed in patients with solid tumors after administration of ONIVYDE/MM-398 at a dose of 80 mg/m$^2$ irinotecan (salt) dose administered once every 2 weeks.

TABLE 1

| Dose (mg/m$^2$) | Total Irinotecan | | | | | SN-38 | | |
|---|---|---|---|---|---|---|---|---|
| | $C_{max}$ [µg/ml] | $t_{1/2}$ [h]† | $AUC_{0-\infty}$ [h · µg/ml]† | $V_d$ [L/m$^2$]† | CL [L h/m$^2$]† | $C_{max}$ [ng/ml] | $t_{1/2}$ [h]† | $AUC_{0-\infty}$ [h · ng/ml]† |
| 80 (n = 25) | 38.0 (36%) | 26.8 (110%) | 1030 (169%) | 2.2 (55%) | 0.077 (143%) | 4.7 (89%) | 49.3 (103%) | 587 (69%) |

*% IQR: % Interquartile Ratio = $\frac{\text{Interquartile–range}}{\text{Median}}$ *100%

†$t_{1/2}$, $AUC_{0-\infty}$ and $V_d$ were only calculated for a subset of patients with sufficient number of samples in the terminal phase: n = 23 for total irinotecan; n = 13 for SN-38.
$C_{max}$: Maximum plasma concentration
$t_{1/2}$: Terminal elimination half-life
$AUC_{0-\infty}$: Area under the plasma concentration curve extrapolated to time infinity
$V_d$: Volume of distribution For ONIVYDE/MM-398, over the dose range of 60 to 180 mg/m$^2$, the maximum concentrations of both total irinotecan and SN-38 increase linearly with dose. The AUCs of total irinotecan increase linearly with dose; the AUCs of SN-38 increase less than proportionally with dose. The half-lives of both total irinotecan and SN-38 do not change with dose. In a pooled analysis from 353 patients, higher plasma SN-38 $C_{max}$ was associated with increased likelihood of experiencing neutropenia, and higher plasma total irinotecan $C_{max}$ was associated with increased likelihood of experiencing diarrhea. Direct measurement of liposomal irinotecan shows that 95% of irinotecan remains liposome-encapsulated during circulation. The volume of distribution of MM-398 80 mg/m$^2$ is 2.2 L/m$^2$. The volume of distribution of Irinotecan HCl is between 110 L/m$^2$ (dose=125 mg/m$^2$) and 234 L/m$^2$ (dose=340 mg/m$^2$). The plasma protein binding of MM-398 is <0.44% of the total irinotecan in MM-398. The plasma protein binding of irinotecan HCl is 30% to 68% and approximately 95% of SN-38 is bound to human plasma proteins. The plasma clearance of total irinotecan from MM-398 80 mg/m$^2$ is 0.077 L/h/m$^2$ with a terminal half live of 26.8 h. Following administration of irinotecan HCl 125 mg/m$^2$, the plasma clearance of irinotecan is 13.3 L/h/m$^2$ with a terminal half live of 10.4 h.

Examples of an effective amount of liposomal irinotecan provided as MM-398 include doses (salt) from about 60 mg/m$^2$ to about 120 mg/m$^2$, including doses of 70, 80, 90, 100, 110 or 120 mg/m$^2$ (based on the weight of irinotecan hydrochloride trihydrate salt) and doses of 50, 60, 70, 80, 95, and 100 mg/m$^2$ (based on the weight of irinotecan free base), each given once every two (2) weeks (e.g., on days 1 and 15 of a 28 day antineoplastic treatment cycle). In some embodiments, the effective amount of MM-398 is about 80 mg/m$^2$ (salt), optionally administered in combination with 400 mg/m$^2$ of leucovorin over 30 minutes, followed by intravenous administration of 2400 mg/m$^2$ of 5-fluorouracil as an infusion over 46 hours. In some embodiments, the effective amount of MM-398 is about 90 mg/m$^2$ (free base).

Figure 16A:
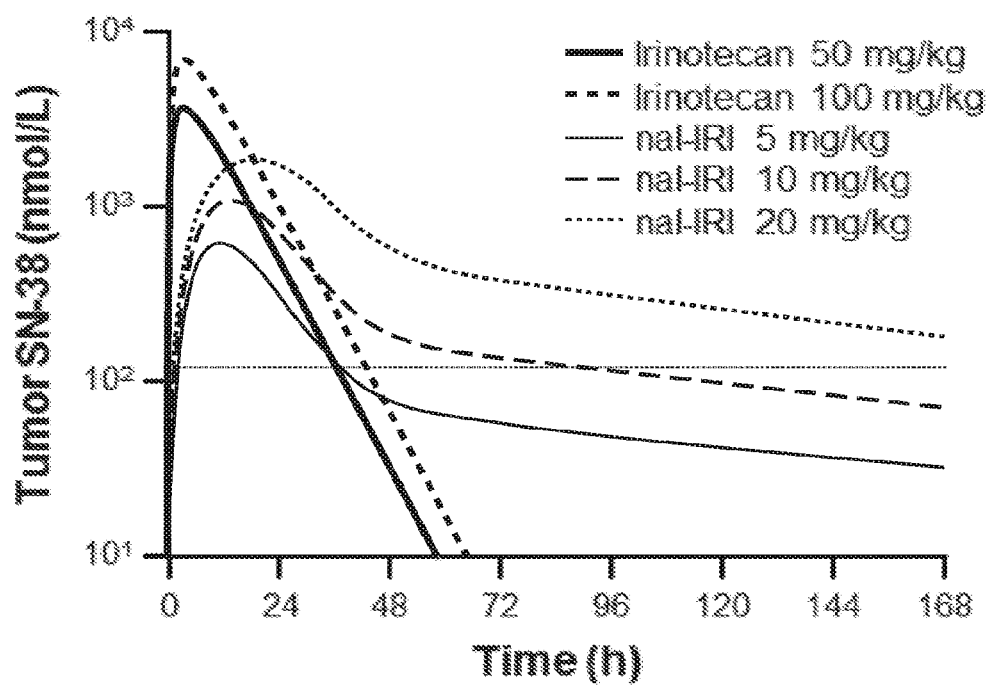
FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg).
Figure 16B:
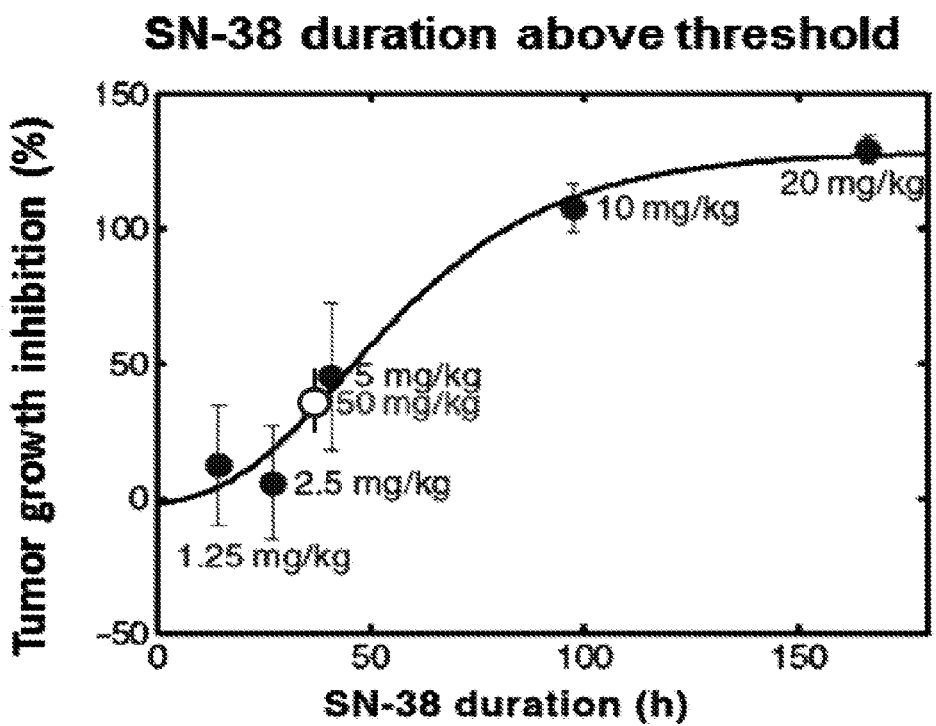
FIG. 16B is a graph showing levels of tumor growth inhibition as a function of time of SN-38 concentration required to yield tumor response.

Liposomal irinotecan MM-398 extends the tumor exposure of the topoisomerase 1 inhibitor SN-38. MM-398 liposomal irinotecan was found to be more active than irinotecan in multiple murine xenograph models. The duration of tumor exposure to the topoisomerase 1 inhibitor SN-38 above a threshold minimum concentration (e.g., 120 nM) correlated with anti-tumor activity of the liposomal irinotecan. In addition, MM-398 liposomal irinotecan can provide prolonged SN-38 tumor durations that exceed those provided by non-liposomal irinotecan. For example, FIG. 13B depicts tumor content of SN-38 in multiple murine cervical cancer models. Nude mice bearing cervical tumors were injected with a single dose of MM-398 at 10 mg/kg and tumor content of CPT-11 and SN-38 were measured by LC-MS. FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg). The graph depicts the prolonged accumulation of SN-38 (concentration) measured in a tumor after liposomal irinotecan (MM-398) administration compared to other organs, obtained using a using HT-29 colorectal cancer (CRC) tumor xenograft-bearing mice. FIG. 16B is a graph showing levels of tumor growth inhibition as a function of time of SN-38 concentration required to yield tumor response. Levels of SN-38 of 120 nM were identified as the SN-38 tumor concentration required to yield tumor response. The in vitro IC50 for SN-38 effect on cell line can be used as an in vivo threshold (GI50 for HT-29 was observed to be about 60 nM). MM-398 liposomal irinotecan was observed to prolong the duration of SN-38 exposure at doses of 10 mg/kg and 20 mg/kg.

PARP Inhibitors

PARPs are a family of enzymes involved in DNA repair that act via two mechanisms: catalytic inhibition and trapping of PARP-DNA complexes, and inhibition of this repair pathway can result in cell death following DNA damage. In preferred embodiments, combining PARP inhibitors with Top1 inhibitors results in increased efficacy in the clinic compared to either agent alone. While it has been demonstrated that synergism between PARP inhibitors and Top1 inhibitors is due to PARP catalytic inhibition, and does not involve PARP trapping, this promising preclinical activity has given rise to unacceptable toxicity in the clinic for these combinations.

The PARP inhibitor can be selected from compounds that inhibit Poly(ADP-ribose) polymerase (PARP), a family of enzymes involved in DNA repair. Preferably, the PARP inhibitor is a compound that acts via two mechanisms: catalytic inhibition and trapping of PARP-DNA complexes. The PARP inhibitor can be one or more clinically available PARP inhibitor compounds (e.g. talazoparib, niraparib, olaparib, and veliparib, among others), including compounds that can act via both mechanisms, although to different degrees. For example, niraparib is much more potent at PARP trapping than veliparib, whereas they both exhibit similar PARP catalytic activity. The PARP inhibitor can be selected from one or more compounds selected from the group consisting of talazoparib, niraparib, olaparib, veliparib, iniparib, rucaparib, CEP 9722 or BGB-290. In a further embodiment, the PARP inhibitor is veliparib, olaparib, rucaparib or niraparib. In another embodiment, the PARP inhibitor is veliparib, or olaparib. The PARP inhibitor can be veliparib administered after liposomal irinotecan. The PARP inhibitor can be olaparib administered after liposomal irinotecan Olaparib is indicated as monotherapy in patients with deleterious or suspected deleterious germline BRCA mutated (as detected by an FDA-approved test) advanced ovarian cancer who have been treated with three or more prior lines of chemotherapy. The recommended dose of olaparib for this indication is 400 mg (eight 50 mg capsules) taken twice daily, for a total daily dose of 800 mg. Patients taking olaparib are instructed to avoid concomitant use of strong and moderate CYP3A inhibitors and consider alternative agents with less CYP3A inhibition. If the inhibitor cannot be avoided, reduce the Lynparza dose to 150 mg (three 50 mg capsules) taken twice daily for a strong CYP3A inhibitor or 200 mg (four 50 mg capsules) taken twice daily for a moderate CYP3A inhibitor.

The PARP inhibitor can inhibit PARP 1 and/or PARP 2. For example, the PARP inhibitor can be a PARP 1/2 inhibitor with IC50 of 5 nM/1 nM in cell-free assays and 300-times less effective against tankyrase-1 (e.g., olaparib). The PARP inhibitor can be an inhibitor of PARP 1 and PARP2 with Ki of 5.2 nM and 2.9 nM respectively in cell-free assays, and inactive to SIRT2 (e.g., veliparib). The PARP inhibitor can be an inhibitor of PARP1 with a Ki of 1.4 nM in a cell-free assay, and can also show binding affinity for other PARP domains (e.g., rucaparib). The PARP inhibitor can be effective against triple negative breast cancer (TNBC) alone or in combination with other agents. The PARP inhibitor can be a PARP1 inhibitor with an IC50 of 0.58 nM in a cell free assay that does not inhibit PARG and is sensitive to a PTEN mutation (e.g., talazoparib). The PARP inhibitor can be a potent and selective tankyrase inhibitor with an IC50 of 46 nM and 25 nM for TNKS 1/2, respectively (e.g., G007-LK). The PARP inhibitor can be a potent inhibitor of PARP 1 with a Ki of less than about 5 nM in a cell free assay (e.g., AG-14361). The PARP inhibitor can be a selective inhibitor of PARP 2 with an IC50 of 0.3 micromolar, and can be about 27-fold selective against PARP 1 (e.g., UPF-1069). The PARP inhibitor can be a potent and selective inhibitor with an IC50 for PARP 3 of about 0.89 micromolar, and about 7-fold selectivity over PARP 1 (e.g., ME0328). The PARP inhibitor can be an inhibitor of PARP 1 and PARP2 with Ki values of 1 nM and 1.5 nM, respectively.

Preferred examples of PARP inhibitors are provided in the table 2A below, as well as pharmaceutically acceptable prodrugs, salts (e.g., tosylates) and esters thereof.

TABLE 2A

Examples of PARP inhibitors

Olaparib (AZD-2281)

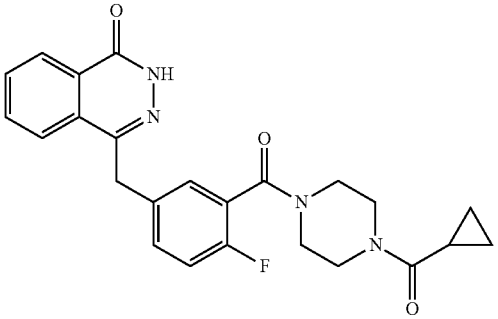 [SMILES: O=C(c1cc(Cc2n[nH]c(=O)c3ccccc23)ccc1F)N1CCN(C(=O)C2CC2)CC1]

Veliparib (ABT-888)

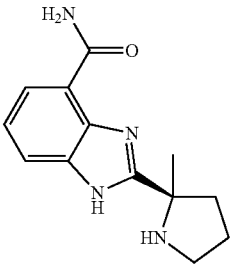 [SMILES: C[C@]1(c2nc3c(C(N)=O)cccc3[nH]2)CCCN1]

Niraparib (MK04827)

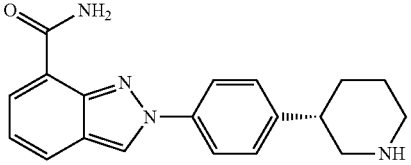 [SMILES: NC(=O)c1cccc2cn(-c3ccc([C@@H]4CCCNC4)cc3)nc12]

Rucaparib (AG 014699)

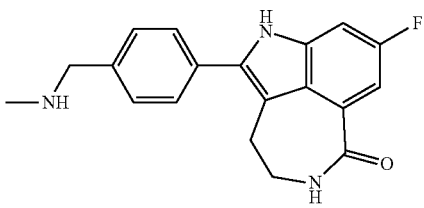 [SMILES: CNCc1ccc(-c2[nH]c3cc(F)cc4c3c2CCNC4=O)cc1]

Talazoparib (BMN-673)

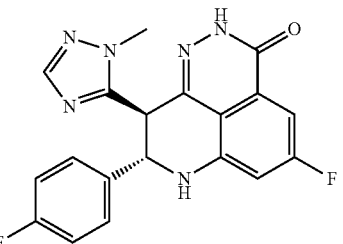

TABLE 2A-continued

Examples of PARP inhibitors

Iniparib (BSI-201

[Chemical structure: benzamide with H₂N-C(=O)- group, NO₂ substituent, and methyl group]

The dose of the PARP inhibitor and the frequency of dosing can be selected based on various characteristics of the PARP inhibitor, including the pharmacokinetic properties of the compound (e.g., half-life), prior dosing regimens and patient characteristics. Parameters that can be used in selecting the PARP inhibitor dose include those listed in Table 2B below.

In addition, patients can be selected to receive treatment combining a topoisomerase inhibitor and a PARP inhibitor. For example, patients can be selected based on their status in BRCA (e.g. BRCA1, BRCA2), Homologous Recombination Deficiency (HRD), BROCA-HR or other genetic risk panel analysis of a patient.

TABLE 2B

Characteristics of Some PARP inhibitors

| Characteristic | Veliparib | Olaparib | Rucaparib | Niraparib | Talazoparib |
|---|---|---|---|---|---|
| Molecular Weight | 244.3 | 434.5 | 323.4 | 320.4 | 380.4 |
| PARP1 IC50 | 4.73-5.2 | 1.94-5 | 1.4-1.98 | 2.1-3.8 | 0.57-1.2 |
| PAR EC50 | 5.9 | 3.6 | 4.7 | | 2.5 |
| Monotherapy dosing | 200-400 mg BID | 300 mg BID | 240-600 mg BID | 300 mg QD | 1 mg QD |
| CDx | BRCA | BRCA, HRD | HRD | BRCA, HR | HRD, HR |

In the methods of this disclosure, the PARP inhibitor is administered at a therapeutically effective dose (e.g., a dose selected for the PARP inhibitor monotherapy, such as from about 200 mg/day to about 800 mg/day for veliparib). In a further embodiment, the PARP inhibitor is administered twice daily at a dose of from about 100 to about 400 mg for veliparib, rucaparib or olaparib. In some embodiments, 200 mg BID dose of veliparib is administered to patients after (e.g., 3-5 days after) each administration of liposomal irinotecan.

Uses in the Treatment of Cancer

In the methods of this disclosure, the PARP inhibitor is preferably administered after an "effective irinotecan plasma clearing interval," as defined above. The effective plasma clearing interval in the methods of this disclosure is from about 24 to about 168 hours, including 48 hours to about 168 hours. In a further embodiment, the effective plasma clearing interval is from about 48 to about 96 hours. In a further embodiment, the effective plasma clearing interval is 24 hours or 2, 3, 4 or 5 days.

In certain embodiments, the MM-398 and the PARP inhibitor are administered in at least one cycle. A cycle comprises the administration of a first agent (e.g., a first prophylactic or therapeutic agents) for a period of time, followed by the administration of a second agent (e.g., a second prophylactic or therapeutic agents) for a period of time, optionally followed by the administration of a third agent (e.g., a third prophylactic or therapeutic agents) for a period of time and so forth, and repeating this sequential administration, i.e., the cycle. In one embodiment, the combination of MM-398 and a PARP inhibitor is administered for at least one cycle. In one embodiment the cycle is a 2 week cycle. In another embodiment, the cycle is a 3 week cycle. In another embodiment, the cycle is a 4 week cycle. In one embodiment MM-398 is administered at the beginning of the cycle and administration of a PARP inhibitor (e.g., veliparib) is delayed until at least about 24, 48, 72, 96, or 120 hours, after the administration of MM-398. In one embodiment, MM-398 is administered as part of a 28 day cycle on days 1 and 15 and the PARP inhibitor is administered on days 3-12 and on days 17-25. In another embodiment, MM-398 is administered as part of a 28 day cycle on days 1 and 15 and the PARP inhibitor is administered on days 5-12 and days 19-25.

In some examples, including the protocols in Table 3, the PARP inhibitor is not administered within 3 days of the administration of liposomal topoisomerase 1 inhibitor such as MM-398 liposomal irinotecan (i.e., the PARP inhibitor is only administered on days that are both at least 2, 3, 4 or 5 days after the administration of the liposomal topoisomerase 1 inhibitor, and 2, 3, 4 or 5 days prior to the next administration of the liposomal topoisomerase 1 inhibitor). Table 3 shows dose timing protocols for administering a therapeutically effective amount of a PARP inhibitor and liposomal irinotecan on certain days of a 28-day antineoplastic treatment cycle.

TABLE 3

Examples of 28-day Treatment Cycles

| Protocol | PARP inhibitor given on days | Liposomal Irinotecan given on days |
|---|---|---|
| 1 | 3-12; 17-25 | 1, 15 |
| 2 | 4-12; 17-25 | 1, 15 |
| 3 | 5-12; 17-25 | 1, 15 |
| 4 | 6-12; 17-25 | 1, 15 |

TABLE 3-continued

Examples of 28-day Treatment Cycles

| Protocol | PARP inhibitor given on days | Liposomal Irinotecan given on days |
|---|---|---|
| 5 | 3-12; 18-25 | 1, 15 |
| 6 | 4-12; 18-25 | 1, 15 |
| 7 | 5-12; 18-25 | 1, 15 |
| 8 | 6-12; 18-25 | 1, 15 |
| 9 | 3-12; 19-25 | 1, 15 |
| 10 | 4-12; 19-25 | 1, 15 |
| 11 | 5-12; 19-25 | 1, 15 |
| 12 | 6-12; 19-25 | 1, 15 |

In some examples, the PARP inhibitor is administered on one or more of days of a 28-day antineoplastic treatment cycle. For example, the PARP inhibitor can be administered on one or more of days 3, 4, 5, 6, 7, 8, 9, 10, 11 and 12 and 19, 20, 21, 22, 23, 24 and 25 of the 28-day antineoplastic treatment cycle when the liposomal irinotecan (e.g., MM-398) is administered once every two weeks, or on days 1 and 15 of the 28-day antineoplastic treatment cycle.

Methods of treatment and therapeutic uses of PARP inhibitors and topoisomerase inhibitors (e.g., liposomal irinotecan) disclosed herein are useful in the treatment of various forms of cancer. Preferably, the cancer includes a diagnosed solid tumor. In some examples, the cancer (e.g., solid tumor) is of a tumor type with one or more DNA repair pathway deficiencies, such as breast and ovarian tumors with BRCA1 or BRCA2 mutations.

In the methods of this disclosure, the cancer is cervical cancer, ovarian cancer, breast cancers including triple negative breast cancer (TNBC), non-small cell lung cancer (NSCLC), small cell lung cancer (SCLC), gastric cancer, pancreatic cancer, colorectal cancer, or a neuroendocrine tumor.

The methods of this disclosure can further comprise administering to the patient one or more additional agents including, but not limited to, anti-emetics such as a 5-HT3 antagonist; agents for treating of diarrhea, such as loperamide; dexamethasone; or other chemotherapeutic agents.

In one embodiment, the methods of the present disclosure result in a pathologic complete response (pCR), complete response (CR), partial response (PR) or stable disease (SD). In another embodiment the combination therapy with MM-398 and a PARP inhibitor, e.g., veliparib, results in therapeutic synergy.

Further aspects include providing an existing standard of care therapy to the patients, which may or may not include treatment with appropriate single agents. In some instances, the standard of care may include administration of a PARP inhibitor compound.

Thus, in one aspect, the present disclosure provides a method of treating a patient with cancer and having a tumor, the method comprising:

i. parenterally (e.g., intravenously) administering to the patient an effective amount of an irinotecan liposomal formulation; and ii. administering to the patient an effective amount of a PARP inhibitor wherein the PARP inhibitor is administered after an effective irinotecan plasma clearing interval.

The present disclosure provides a method of treating a patient with cancer and having a tumor, the method comprising a treatment regimen that may be repeated at weekly or longer intervals (e.g., Q2W, Q3W, or Q4W), each instance of the treatment comprising:

i. intravenously administering to the patient an effective amount of an irinotecan liposomal formulation of a Top1 inhibitor such as irinotecan, topotecan, lurtotecan, indotecan, and indimitecan; and ii. administering to the patient and effective amount of a PARP inhibitor wherein the PARP inhibitor is administered after an interval following completion of the administration of the Top1 inhibitor, e.g., an effective irinotecan plasma clearing interval.

In a further embodiment, the method comprises:

i. intravenously administering to the patient an effective amount of an irinotecan liposomal formulation having a terminal elimination half-life of about 26.8 hours and a maximal irinotecan plasma concentration of about 38.0 micrograms/ml; and ii. administering to the patient and effective amount of a PARP inhibitor wherein the PARP inhibitor is administered after an interval of 24 hours or up to three days following completion of the administration of the irinotecan.

EXAMPLES

The following non-limiting examples illustrate the methods of the present disclosure.

Example 1: In Vitro Studies

In vitro studies were performed testing combinations of various PARP inhibitors and topoisomerase inhibitors liposomal irinotecan and SN-38.

FIGS. 1A-1D show line graphs that depict cervical cancer cell viability following treatment with SN-38 and/or various PARP inhibitors. Unless otherwise indicated, the data in each of these figures was obtained by measuring cell viability of 5 different cervical cancer cells (ME-180 in FIG. 1A, MS-751 in FIG. 1B, C-33A in FIG. 1C, SW756 in FIG. 1D and SiHa in FIG. 1E) with 1000 cells/well in a 384 well plate treated with SN-38 (topoisomerase 1 inhibitor) and/or one of 3 different PARP inhibitors (veliparib, niraparib, or olaparib) at 0.33 micrograms/mL) for 24 hours, followed by washing and incubation for an additional 72 hours with fresh media.

The combination of the topoisomerase 1 inhibitor SN-38 and various PARP inhibitors (veliparib, olaparib and rucaparib) were tested in vitro with various small cell lung cancer (SCLC), pancreatic cancer and breast cancer cell lines. At 2 nM SN-38 concentration, an additive/synergistic growth inhibition of the cancer cells was observed in combination with olaparib, veliparib and rucaparib (with veliparib observed to be slightly less potent in the combination with SN-38 than olaparib and rucaparib). At all concentrations tested, the static growth of the cancer cell population was achieved. FIGS. 2A-2E are graphs showing the results of in vitro experiments evaluating combinations of the topoisomerase 1 inhibitor SN38 with various PARP inhibitors, formatted according to the tables 4-5 below (plates of 5,000 cells/well, 100 microliters per well; drugs added with 20× at 10 microliters per drug, top up to 100 microliters total with DMEM; then initiate scan every 4 hours up to 68 hours).

TABLE 4

| Treatment | Small Cell Lung Cancer | | Pancreatic Cancer | | TNBC MDA-MB-231 |
|---|---|---|---|---|---|
| | DMS-114 | NCI-H1G48 | CFPAC-1 | BxPC-3 | |
| SN-38 & Olaparib | Plate 1 | Plate 2 | Plate 3 | Plate 4 | Plate 5 |
| SN-38 & Rucaparib | Plate 1 | Plate 2 | Plate 3 | Plate 4 | Plate 5 |
| SN-38 & Veliparib | Plate 1 | Plate 2 | Plate 3 | Plate 4 | Plate 5 |

TABLE 5

Target Concentrations

| Drug | Active Range based on XTC008 | Estimated tumor range (nM) | Dose Level | Conc' (nM) |
|---|---|---|---|---|
| SN-38 | 1-50 nM | 3-103 nM (396); IRI <200 nM | S1 | 2 |
| | | | S2 | 5 |
| | | | S3 | 10 |
| | | | S4 | 20 |
| | | | S5 | 50 |
| Olaparib | 1000-10000 nM | 8000 nM | O1 | 2000 |
| | | | O2 | 4000 |
| | | | O3 | 8000 |
| Veliparib | 1000-10000 nM | >2000 nM | V1 | 2000 |
| | | | V2 | 4000 |
| | | | V3 | 8000 |
| Rucaparib | 3-100 nM (Panc) | <6000 nM | R1 | 2000 |
| | | | R2 | 4000 |
| | | | R3 | 8000 |

Figure 2A:
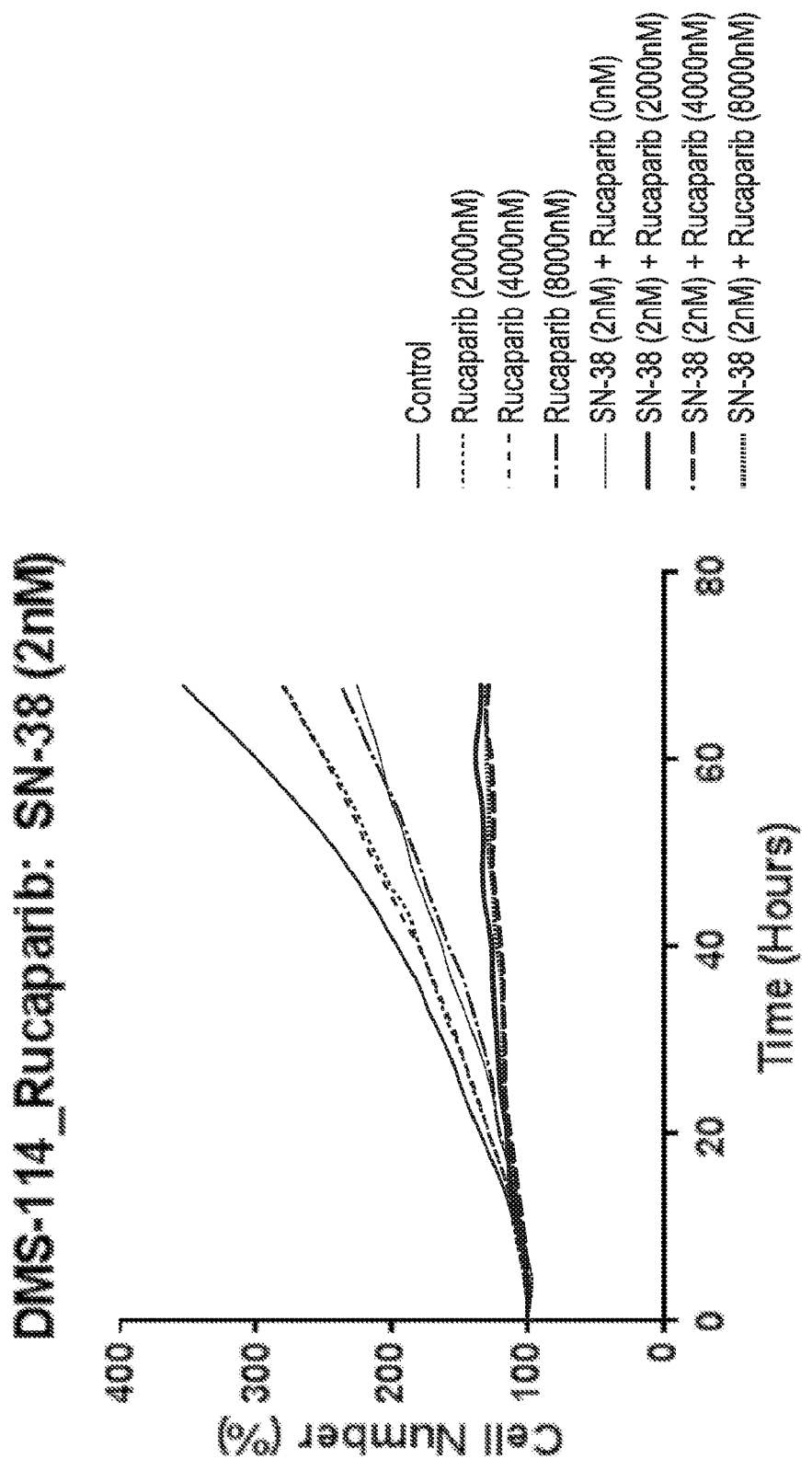
FIG. 2A is a graph showing the results of in vitro measurement of % cell number over time for DMS-114 small cell lung cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with DMS-114 SCLC cells. FIG. 2A is a graph showing the results of in vitro measurement of % cell number over time for DMS-114 small cell lung cancer cells treated with the topoisomerase inhibitor SN-38 and the PARP inhibitor rucaparib.

Figure 2B:
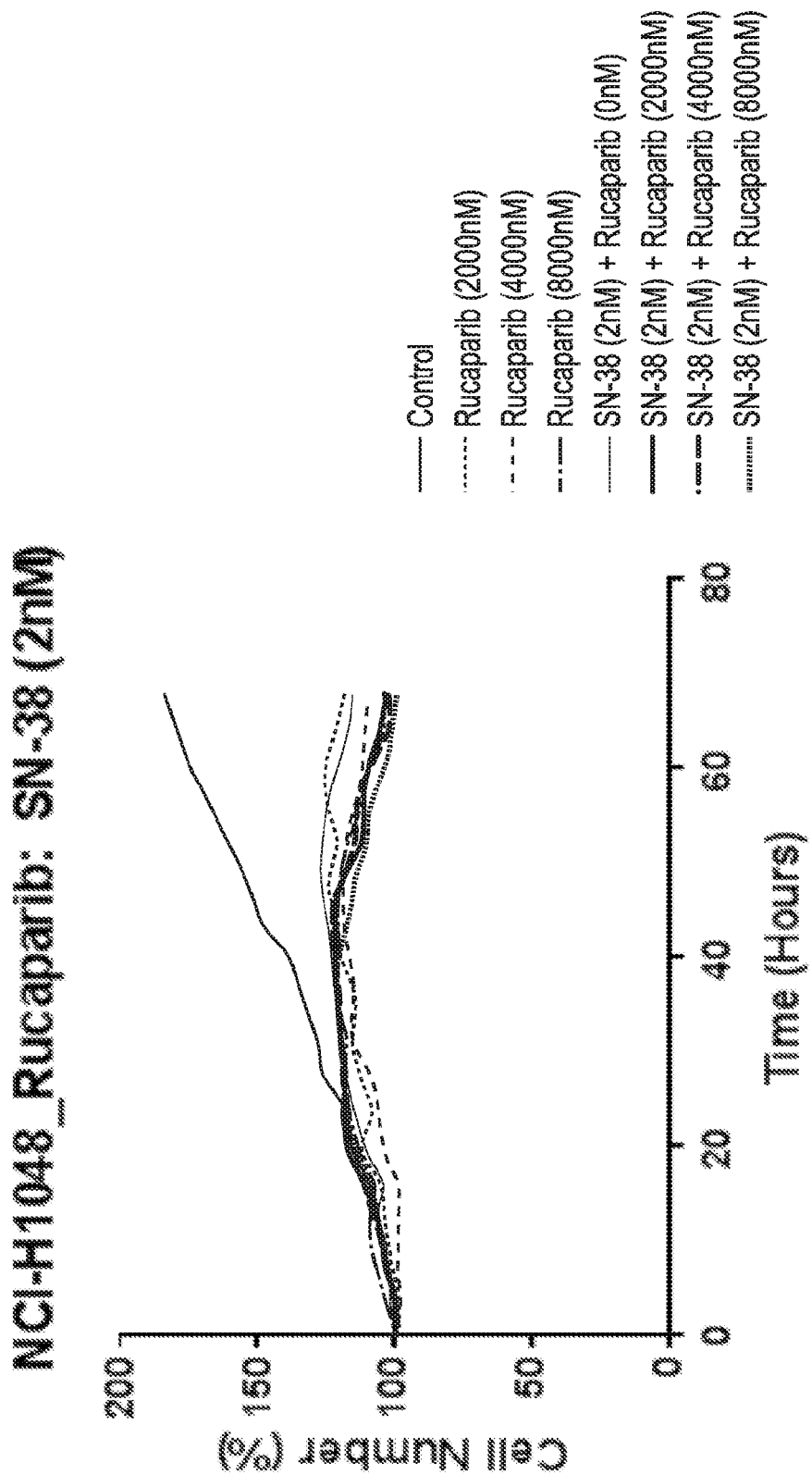
FIG. 2B is a graph showing the results of in vitro measurement of % cell number over time for NCI-H1048 small cell lung cancer cells treated with the topoisomerase inhibitor SN-38 and the PARP inhibitor rucaparib.

The NCI-H1048 SCLC cells were slow-growing and very sensitive to combinations of olaparib and rucaparib with SN-38 at 2 nM. FIG. 2B is a graph showing the results of in vitro measurement of % cell number over time for NCI-H1048 small cell lung cancer cells treated with the topoisomerase inhibitor SN-38 and the PARP inhibitor rucaparib.

Figure 2C:
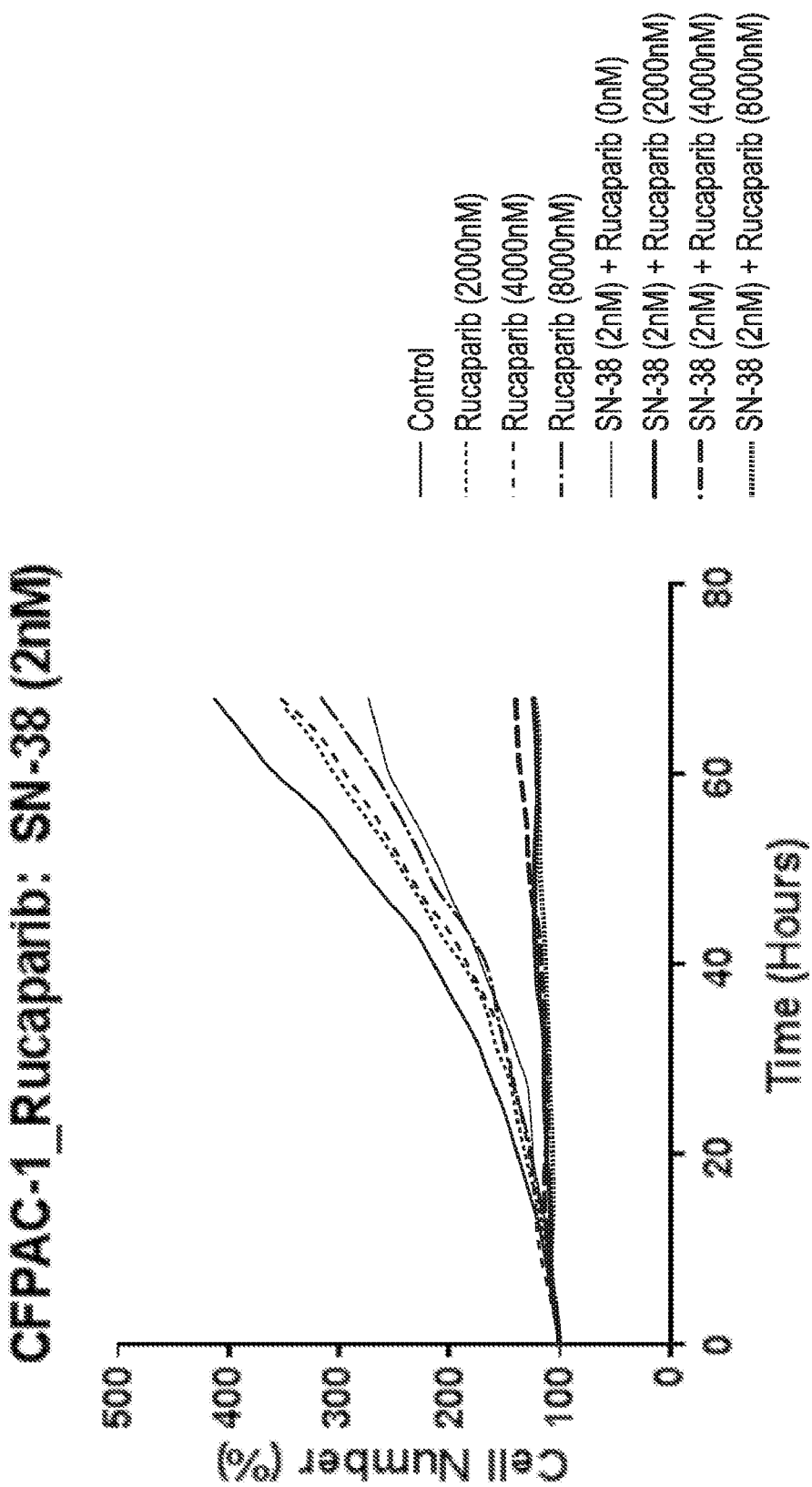
FIG. 2C is a graph showing the results of in vitro measurement of % cell number over time for CFPAC-1 pancreatic cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with CFPAC-1 pancreatic cancer cells. FIG. 2C is a graph showing the results of in vitro measurement of % cell number over time for CFPAC-1 pancreatic cancer cells treated with the topoisomerase inhibitor SN-38 and the PARP inhibitor rucaparib.

Figure 2D:
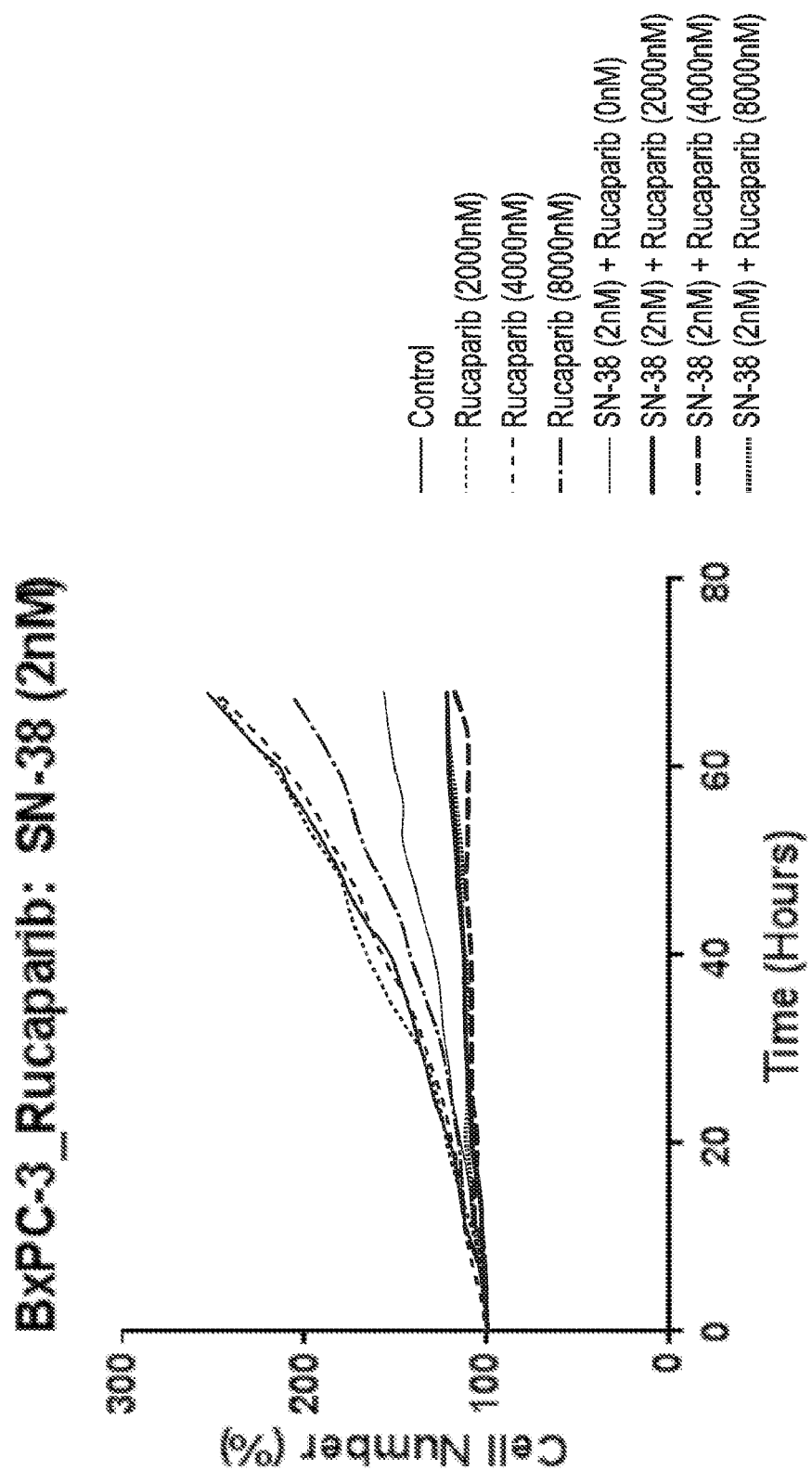
FIG. 2D is a graph showing the results of in vitro measurement of % cell number over time for BxPC-3 pancreatic cancer cells treated with the topoisomerase inhibitor SN-38 and the PARP inhibitor rucaparib.
Figure 2E:
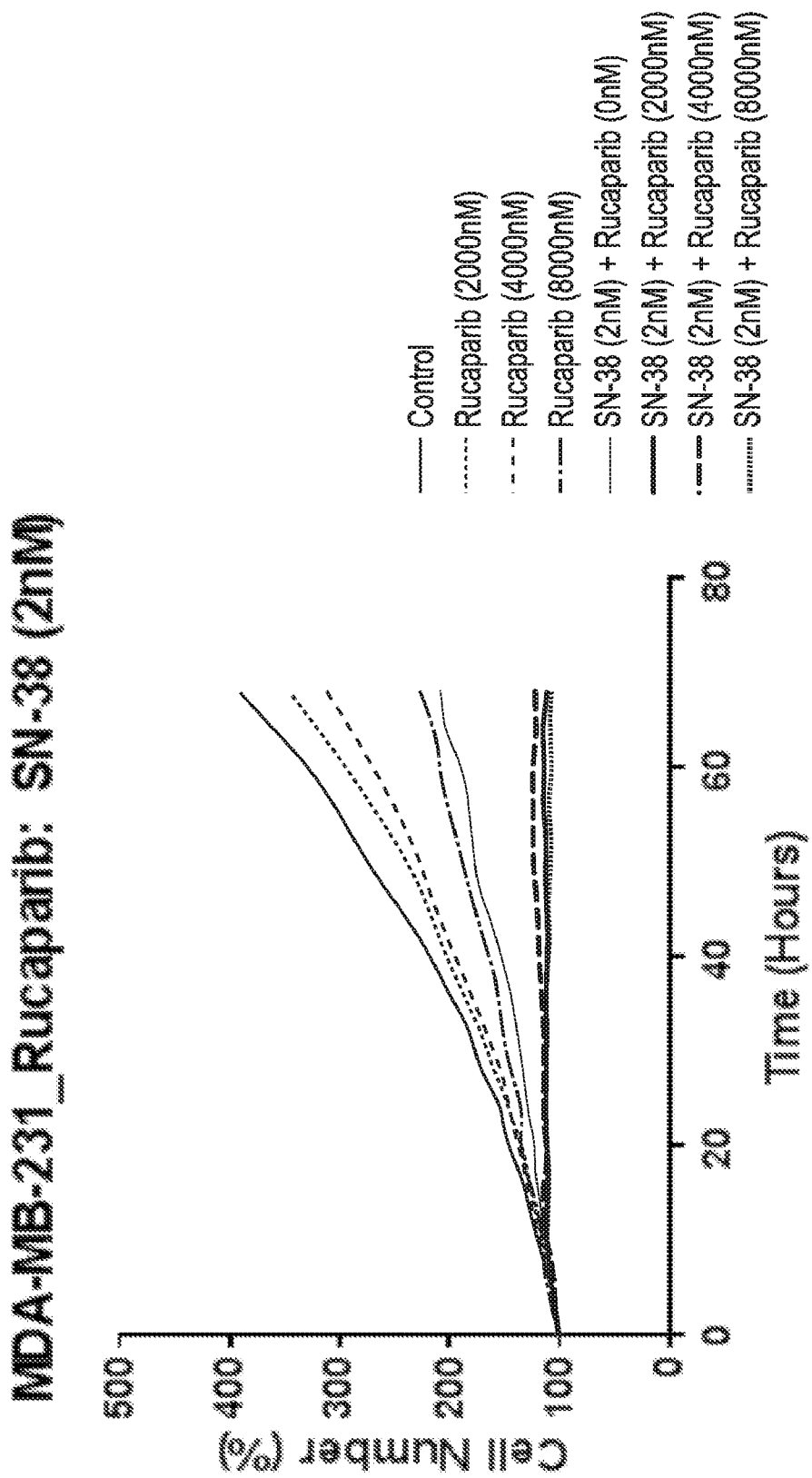
FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.
Figure 6A:
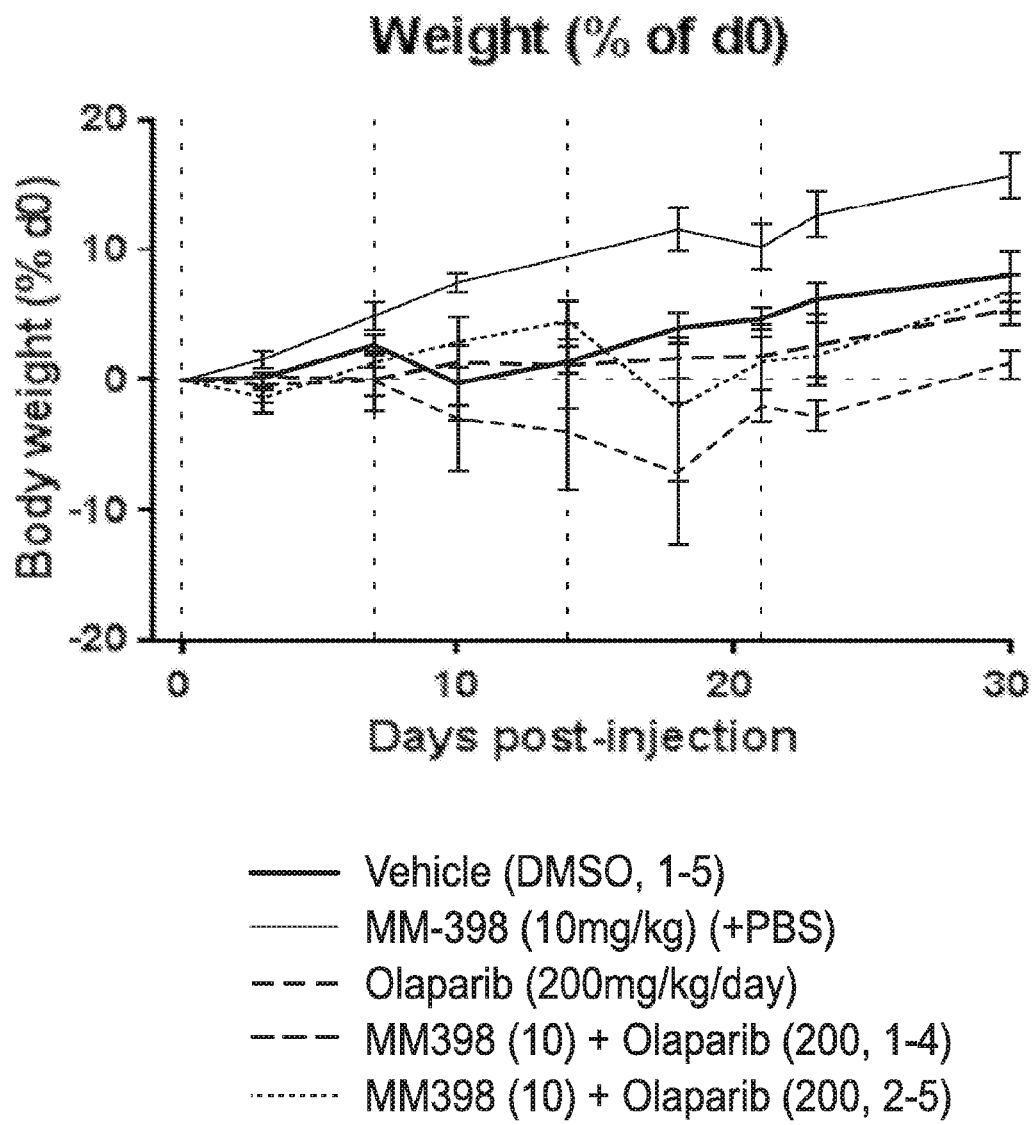
FIG. 6A is a graph comparing the results of a murine tolerability study measuring % change in bodyweight after administration of 10 mg/kg of MM-398 (+PBS); 200 mg/kg/day of Olaparib; 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6B:
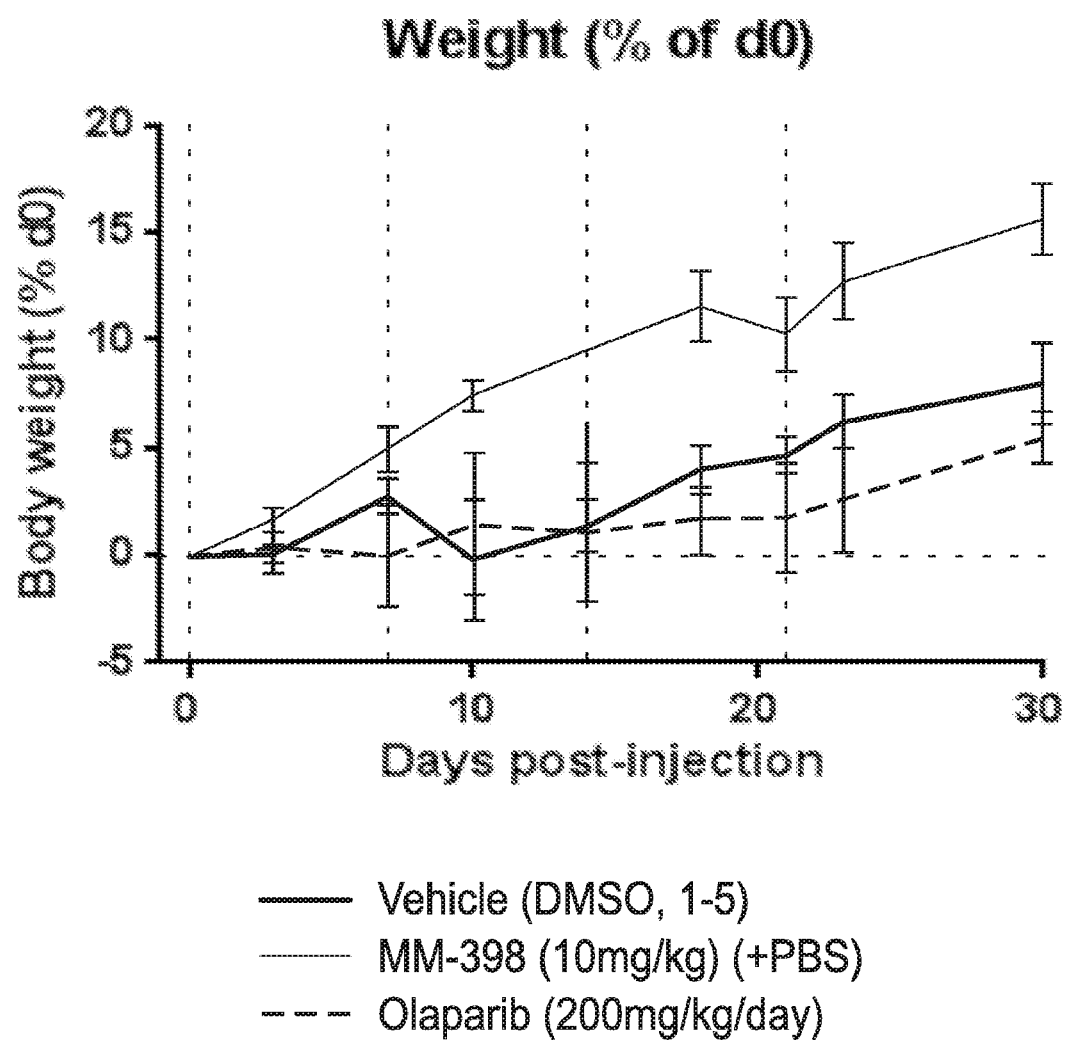
FIG. 6B is a graph comparing the results of a murine tolerability study measuring % change in bodyweight after administration of 10 mg/kg of MM-398 (+PBS) and 200 mg/kg/day of Olaparib.
Figure 6C:
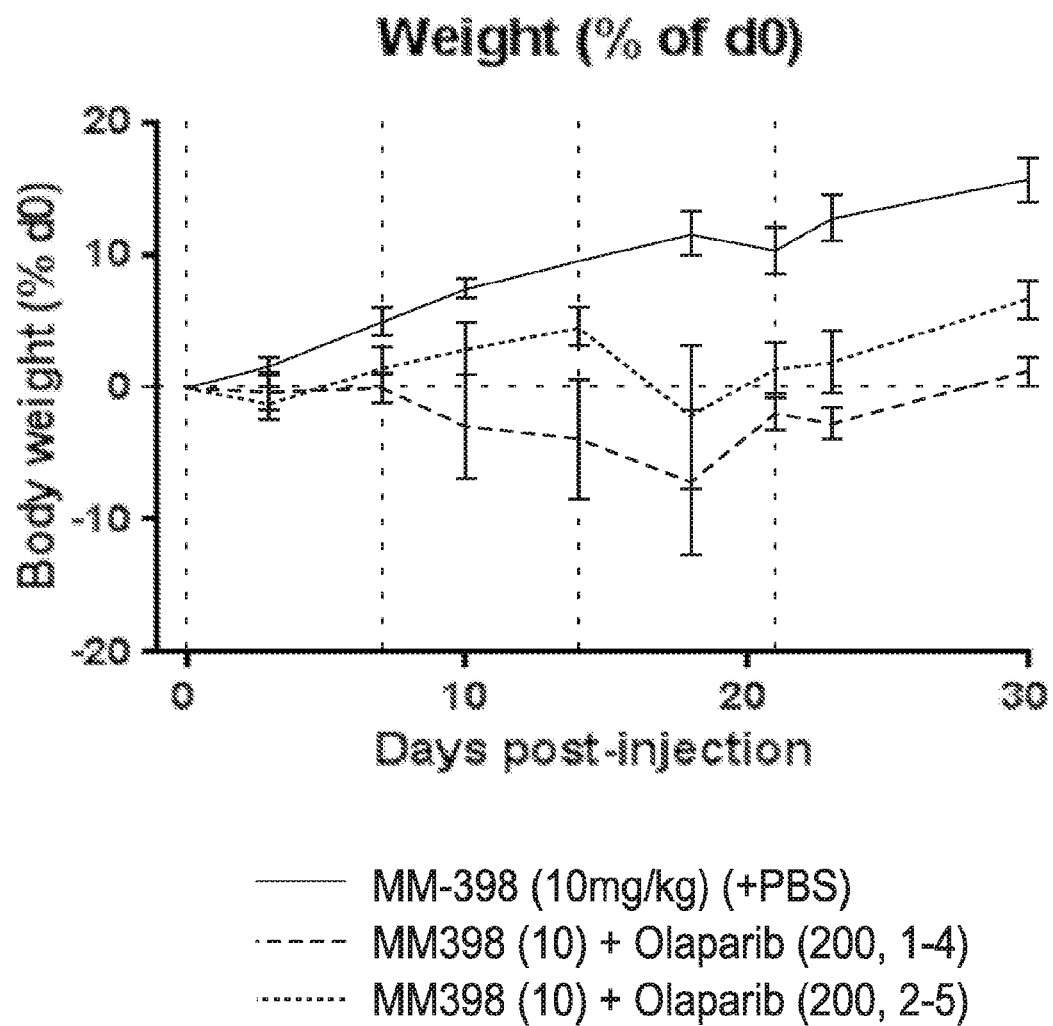
FIG. 6C is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6D:
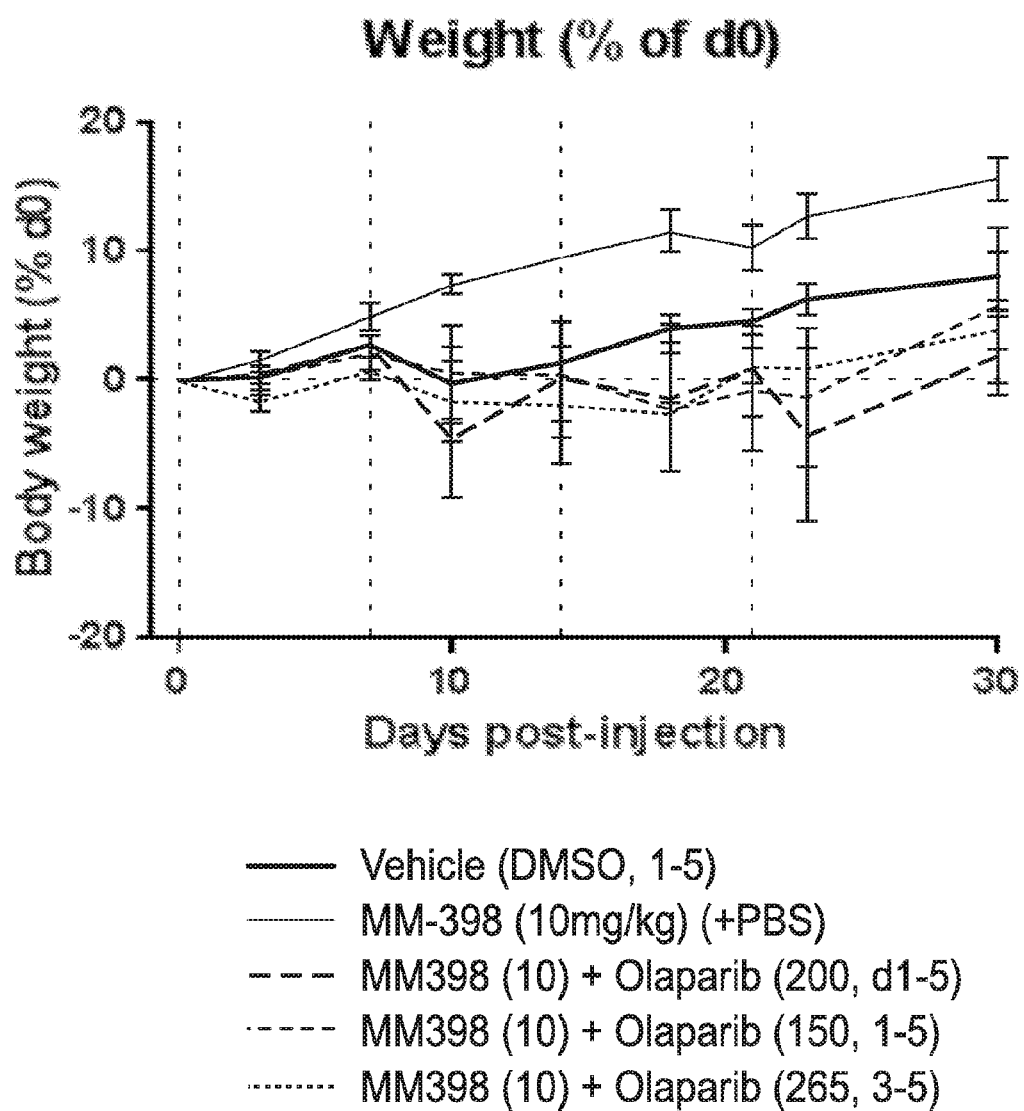
FIG. 6D is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-5; 10 mg/kg of MM-398 (+PBS) with 150 mg/kg/day of Olaparib on days 1-5; and 10 mg/kg of MM-398 (+PBS) with 265 mg/kg/day of Olaparib on days 3-5.

FIG. 2D is a graph showing the results of in vitro measurement of % cell number over time for BxPC-3 pancreatic cancer cells treated with the topoisomerase inhibitor SN-38 and the PARP inhibitor rucaparib. FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.

Figure 13A:
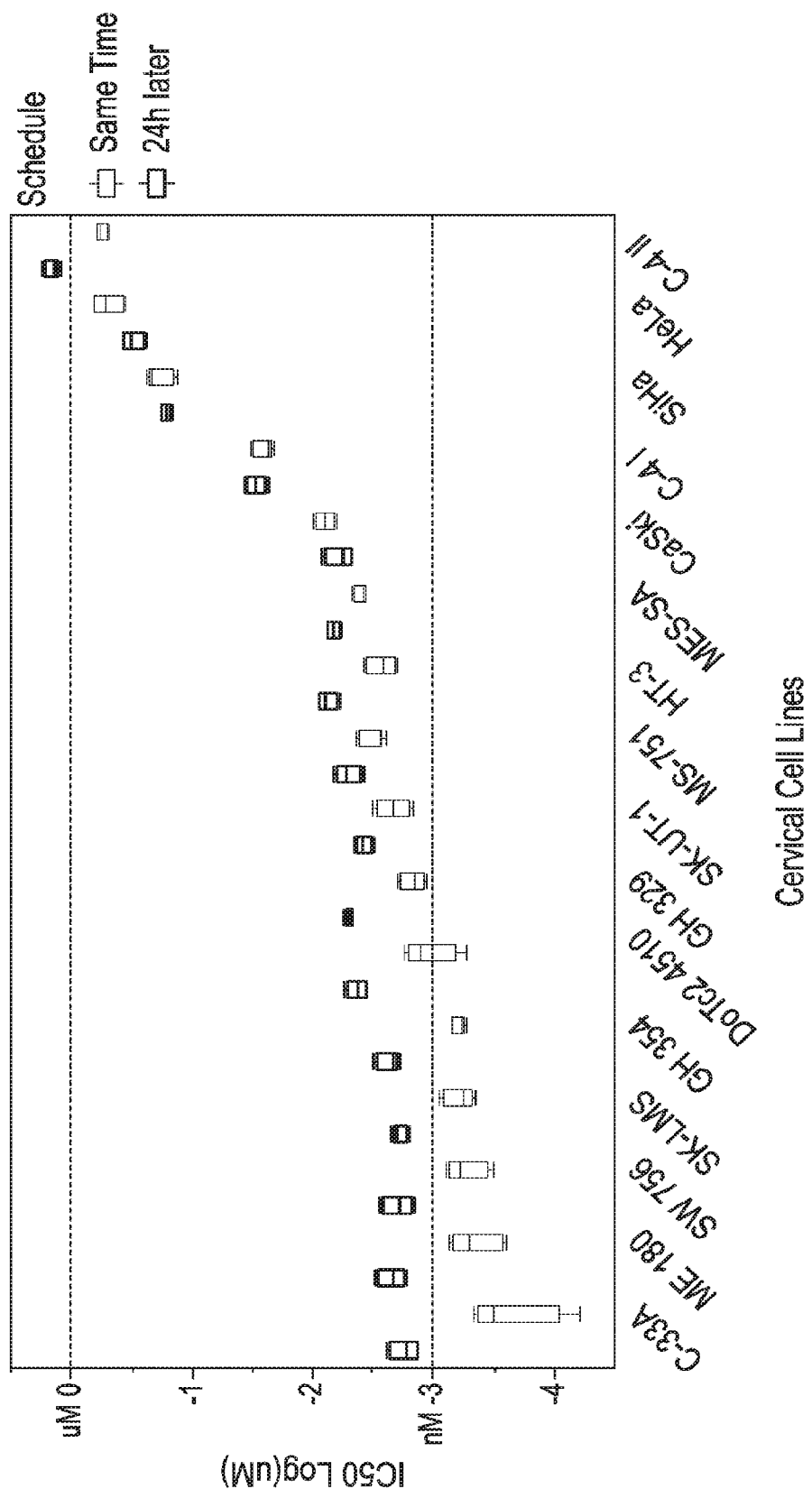
FIG. 13A is a graph showing the in vitro activity (IC50) for multiple cervical cancer cell lines treated with veliparib and SN38, added together or with the veliparib added 24 hours after the SN38.
Figure 13B:
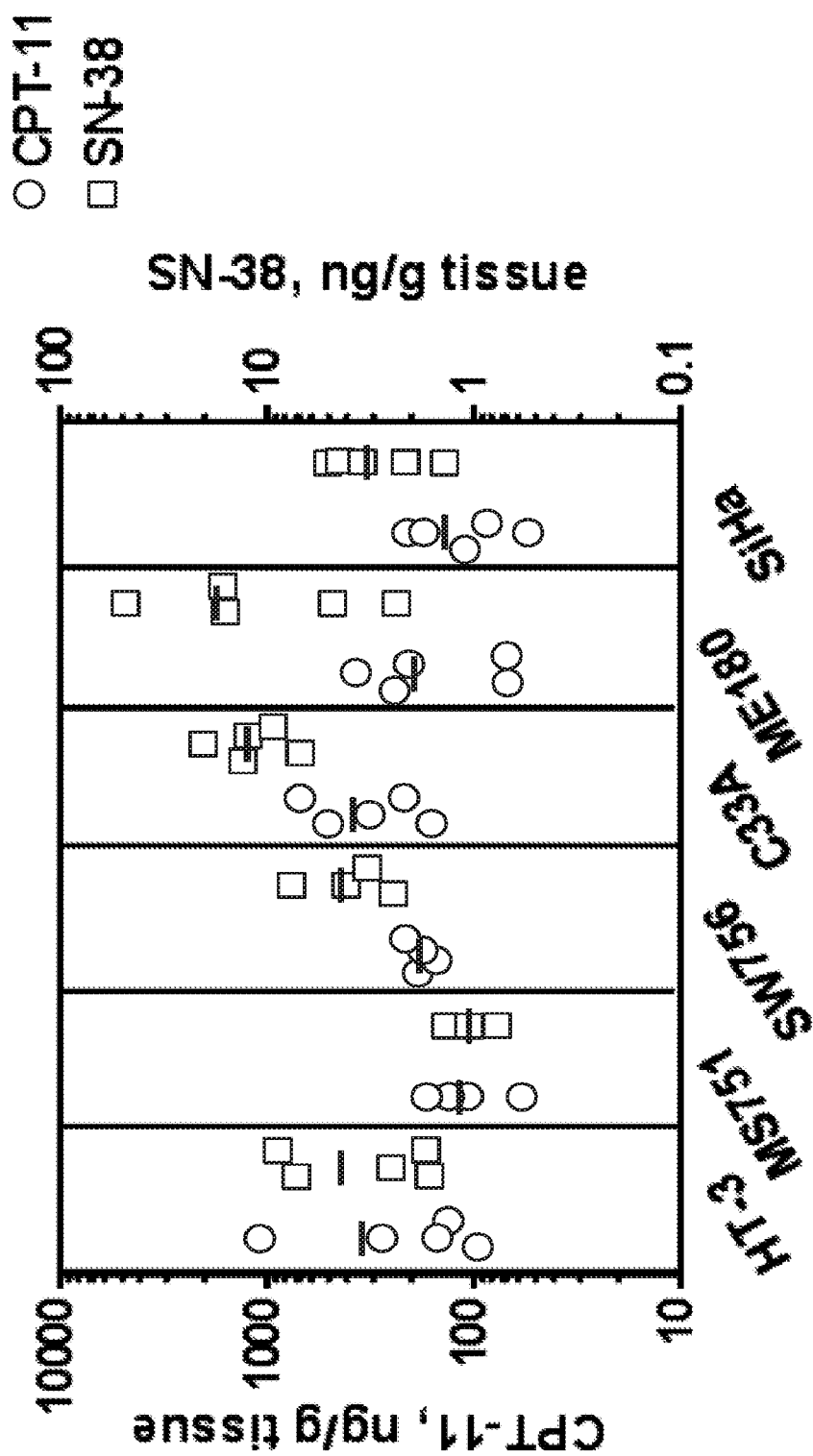
FIG. 13B is a graph showing the cell viability (CTG assay) in nude mice with cervical cancer tumors, injected with a single dose of MM-398 (10 mg/kg) followed by measurement of irinotecan and SN38 content in the tumor measured by LC-MS.

FIG. 13A depicts the in vitro activity of SN-38 in cervical models. Cervical cells lines were treated with veliparib and SN-38 at either the same time or with scheduling with Veliparib being added 24 h after SN-38, and cell viability was measured using CTG assay.

Example 2: Pre-Clinical Dose Tolerability Studies

Various pre-clinical in vivo experiments were conducted to evaluate delayed dosing of veliparib relative to liposomal irinotecan can alleviate systemic toxicity, including a pre-clinical dose tolerability study. The combination of veliparib and irinotecan has been plagued by dose-limiting toxicities that have prevented this combination from being dosed at high (effective) doses of each drug, thereby limiting its clinical utility. To address this problem, pre-clinical studies evaluated administering a liposomal preparation of a topoisomerase 1 inhibitor, followed by the administration of a PARP inhibitor at least 1 day (preferably 2-3 days) after the day on which the liposomal topoisomerase 1 inhibitor was administered.

The advantage of dosing with MM-398 compared to free irinotecan is the extended PK profile and prolonged local tumor exposure of MM-398. Since SN-38 is cleared more quickly from normal tissues than from tumor, delayed dosing of veliparib (e.g. starting veliparib dosing a few days after MM-398 administration) allows for the window of maximum irinotecan-induced toxicity to pass in the absence of concurrent veliparib toxicity. However, the tumor levels of SN-38 are sustained longer than in healthy tissue, such that upon PARP inhibitor dosing subsequent to liposomal Top1 inhibitor (e.g., MM-398) administration, both drugs will act on tumor tissue simultaneously.

To demonstrate that delayed dosing of veliparib relative to nal-IRI can alleviate systemic toxicity, a pre-clinical dose tolerability study was performed. Mice were dosed chronically with nal-IRI once weekly at various doses on Day 1, while veliparib was dosed once daily at a fixed dose for 3 consecutive days each week (either on Days 2-4, Days 3-5, or Days 4-6), and body weight was followed as a gross measure of toxicity. All mice were dosed chronically once weekly on day 1, with veliparib subsequently dosed for 3 consecutive days either on days 2-4, days 3-5, or days 4-6. Mice were weighed daily and % bodyweight gain is indicated on the Y-axis. Weight loss is indicative of intolerability of the combination. Notably, the highest (50 mg/kg) dose of MM-398 liposomal irinotecan was best tolerated (i.e., lowest measured reduction in % bodyweight observed over the experiment) when the veliparib was administered on days 4, 5 and 6 (FIG. 5C). Similarly, the combination of veliparib and MM-398 was best tolerated at lower MM-398 liposomal irinotecan doses when the veliparib was only administered on days 4, 5, and 6 after MM-398 administration. Toxicity of the combination was seen at the highest doses of MM-398 when given in close proximity to the veliparib doses (FIG. 5A). However, this toxicity could be alleviated either by dose reducing MM-398 or delaying the start of veliparib dosing, whereby the highest dose of MM-398 could be successfully dosed with veliparib if given on Days 4-6 following Day 1 dosing of MM-398. The Day 4-6 veliparib dosing schedule (following day 1 dosing of MM398) was followed in subsequent efficacy studies which demonstrated synergy of the combination in two cervical cancer tumor xenograft models, in which veliparib alone was not efficacious (FIG. 7A) and a second model in which neither MM-398 or veliparib were efficacious as single agents (FIG. 7B), however the combination demonstrated tumor growth inhibition (FIG. 7B).

To exemplify an embodiment demonstrating that delayed dosing of olaparib relative to MM-398 can alleviate systemic toxicity, a pre-clinical dose tolerability study was performed. FIG. 4 depicts a graphical representation of a murine tolerability study design comparing MM-398 and olaparib as a monotherapy or in combination using a fixed dose of MM-398 and varying doses of olaparib, with various dosing schedules for different groups: Group 1: MM-398 alone IV (10 mg/kg); Group 2: olaparib alone oral (200 mg/kg); Group 3: MM-398 (d1)+olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (265 mg/kg, d3-5); group 8: DMSO alone oral (FIGS. 6A-6D). Mice that received monotherapy of MM-398, olaparib were dosed 5× weekly. Mice that received a combination of a constant concentration of MM-398 (10 mg/kg) and varying concentration of olaparib were dosed in varying schedules: Group 3: MM-398 (d1)+olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (200 mg/kg, d3-5). Mice were monitored for treatment dependent toxicities by charting body weight and percent survival. Addition of olaparib seemed to be more toxic as compared to monotherapy, however delaying start of olaparib administration to d3 seemed to decrease olaparib specific toxicity as compared to concurrent therapy. Mice were dosed chronically with MM-398 once weekly at various doses on Day 1, while olaparib was dosed once daily at a weekly fixed dose for 5, 4 or 3 consecutive days each week (either on Days 1-5, Days 1-4, Days 2-5 or Days 3-5), and body weight and percent survival were followed as a gross measure of toxicity. Toxicity of the combination was seen at the highest doses of MM-398 when given in close proximity to the olaparib doses (FIG. 4). However, this toxicity could be alleviated either by delaying the start of olaparib dosing, whereby the highest dose of MM-398 could be successfully dosed with olaparib if given on Days 3-5 following Day 1 dosing of MM-398.

Mice were dosed chronically with MM-398 once weekly at various doses on Day 1, while veliparib was dosed once daily at a fixed dose for 3 consecutive days each week (either on Days 2-4, Days 3-5, or Days 4-6) and body weight was followed as a gross measure of toxicity. Toxicity of the combination was seen at the highest doses of nal-IRI when given in close proximity to the veliparib doses. However, this toxicity could be alleviated either by dose reducing nal-IRI or delaying the start of veliparib dosing. This dosing schedule was followed in subsequent mouse efficacy studies which demonstrated synergy of the combination in two cervical cancer tumor xenograft models, in which veliparib alone was not efficacious, and a second model in which neither nal-IRI or veliparib were efficacious as single agents, however the combination demonstrated tumor growth inhibition.

Figure 8A:
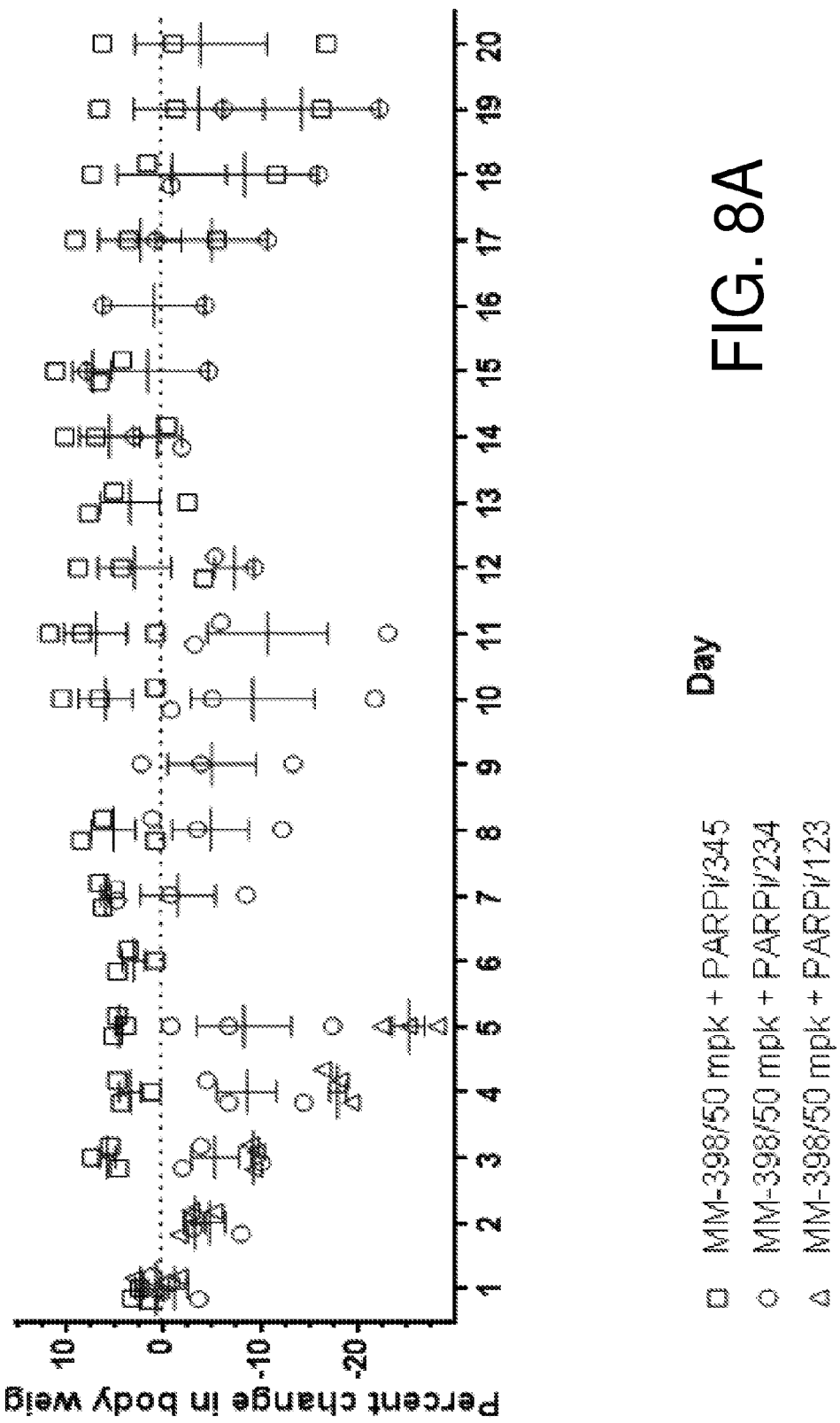
FIG. 8A is a graph that depicts the in vivo tolerability of 50 mg/kg dose of MM-398 in combination with 50 mg/kg veliparib given on days 1, 2, and 3; or 2, 3, and 4; or 3, 4, and 5 after administration of the MM-398.
Figure 8B:
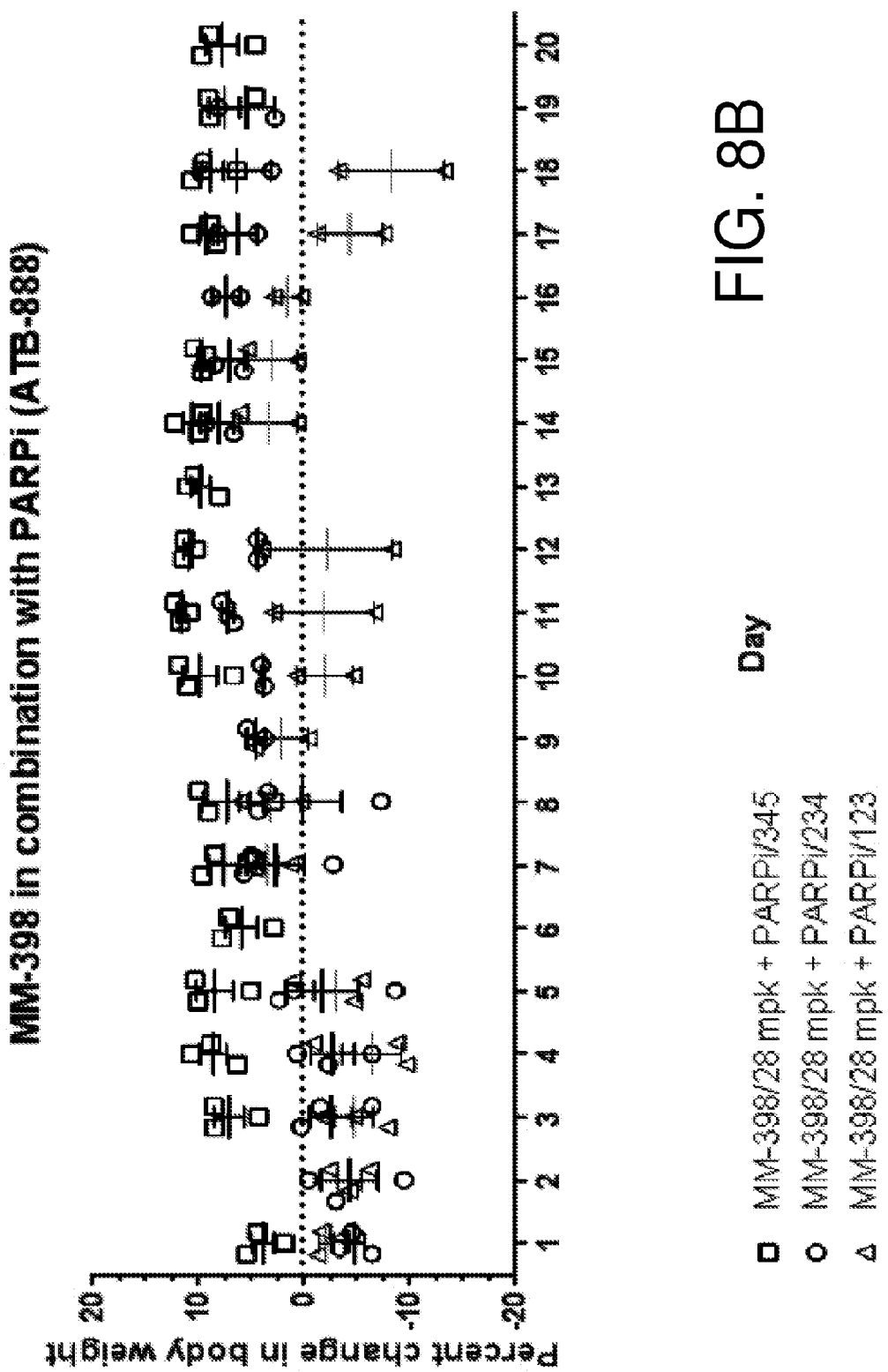
FIG. 8B is a graph that depicts the in vivo tolerability of 28 mg/kg dose of MM-398 in combination with 50 mg/kg veliparib given on days 1, 2, and 3; or 2, 3, and 4; or 3, 4, and 5 after administration of the MM-398.

The tolerability of the combination of MM398 in a mouse model on day 1 was evaluated in combination with the administration of veliparib on days 1-3, days 2-4 and days 3-5. The tolerability of the combined regimen in mice (measured by change in percent bodyweight over 20 days) increased as the first administration of the veliparib occurred on day 2 and day 3, with day 3 initial veliparib dosing providing the most tolerated dosing schedule. FIG. 8A is a graph that further depicts the in vivo tolerability of the 50 milligrams/kilogram (mpk) dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit. FIG. 8B is a graph that further depicts the in vivo tolerability of the 28 mpk dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit.

Figure 12:
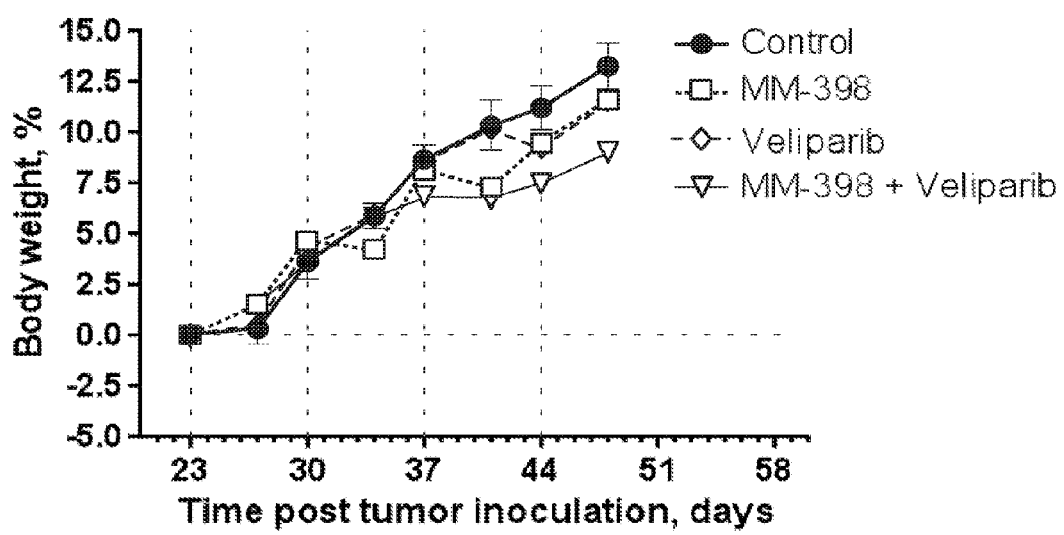
FIG. 12 depicts the effect of MM-398 in combination with veliparib in C33A xenograft model and body weight, where veliparib was dosed 72 h following liposomal irinotecan (5 mg/kg MM398) and/or the PARP inhibitor veliparib (50 mpk) on days 3-5 starting after administration of MM398.

FIG. 12 is a graph showing that treatment of mice with the combination of MM-398 with veliparib in C33A xenograft model described in Example 4 also lead to decreases in body weight as compared to administration of either drug alone.

These studies demonstrated that this toxicity could be alleviated by delaying the start of PARP inhibitor dosing, preferably by 2-3 days after the day on which liposomal irinotecan was administered. A dosing schedule where the PARP inhibitor was only administered on days subsequent to administration of liposomal irinotecan was followed in mouse efficacy studies (Example 3) demonstrating therapeutic synergy of the combination of a PARP inhibitor and liposomal irinotecan in two cervical cancer tumor xenograft models (in which veliparib alone was not efficacious, and a second model in which neither MM-398 or veliparib were efficacious as single agents, however the combination demonstrated tumor growth inhibition).

Example 3: Pre-Clinical Efficacy of Liposomal Irinotecan

In vivo tumor xenograft studies demonstrated that the efficacy of liposomal irinotecan is greater than free irinotecan. In addition, in vivo tumor xenograft studies demonstrated MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Liposomal irinotecan (MM-398) has greater efficacy in various cancer models, compared to non-liposomal irinotecan. Cancer cells were implanted subcutaneously in mice; when tumors were well established and had reached mean volumes of 200 mm3, IV treatment with free irinotecan, MM-398 or control was initiated. The doses of free and nanoliposomal irinotecan used in each study are indicated above, with dose time points indicated by arrows. Tumor permeability as well as tumor tissue carboxylesterase (CES) activity, which is responsible for the enzymatic conversion of CPT-11 to SN-38, are predicted to be critical factors for local tumor exposure of SN-38 following MM-398 dosing. In vivo tumor xenograft studies have demonstrated that efficacy of MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Example 4: Pre-Clinical Activity of Liposomal Irinotecan and PARP Inhibitors

Figure 7A:
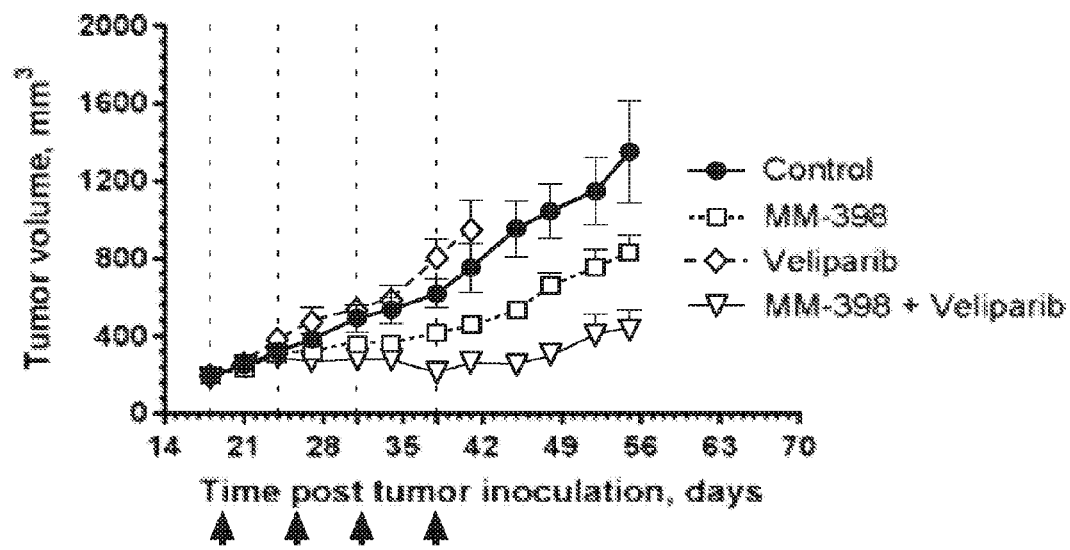
FIG. 7A is a graph showing data from a mouse xenograft study using MS751 cervical cancer cells in a murine model treated with liposomal irinotecan (5 mg/kg MM398) and/or the PARP inhibitor veliparib on days 4-6 after administration of MM398.
Figure 7B:
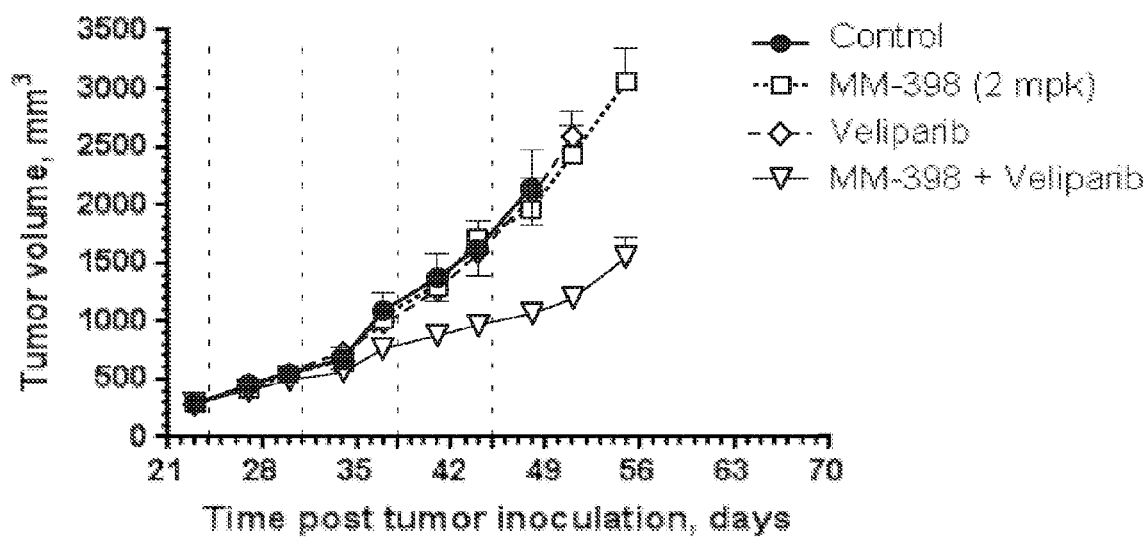
FIG. 7B is a graph showing data from a mouse xenograft study using MS751 cervical cancer cells in a murine model treated with liposomal irinotecan (2 mg/kg MM398) and/or the PARP inhibitor veliparib on days 4-6 after administration of MM398.

Referring to FIG. 7A and FIG. 7B, the antitumor activity of MM-398 was studied in combinations with veliparib (PARPi) in multiple cervical xenograft models. In this study, MS-751 and C33A xenograft models of cervical cancer were employed to probe the effect of administering suboptimal doses of MM-398 in combination with the PARP inhibitor veliparib. Differential tissue levels of MM-398 at 24 and 72 hours indicated that MM-398 and the active metabolite SN-38 cleared faster from the liver, spleen, colon, and plasma, than from tumors. The combination of veliparib and MM-398 gave improvements in key PD biomarkers (cleaved caspase and yH2AX) when compared to veliparib or MM-398 alone. FIGS. 7A and 7B show that the combination of MM-398+veliparib is synergistic. Two different cervical cancer xenograft models were utilized to study the efficacy of MM-398 dosed once weekly on Day 1 (arrows), veliparib dosed at 50 mg/kg orally once daily for 3 consecutive days on Days 4-6 of each week, or the combination dosed on the same schedule as the single agent treatments combined. (A) MS751 cervical cancer xenograft model using MM-398 dosed at 5 mg/kg and (B) C33A cervical cancer xenograft model using MM-398 dosed at 2 mg/kg. In the study, control mice were the same strain, and were harvested prior to tested mice (slightly younger). Data is not presented for mice removed from study for weight loss or for mice removed unintentionally before end date.

Cervical MS-751 Xenograft Model

The MS-751 Xenograft Model details are summarized in Table 6.

TABLE 6

| Mouse strain: | Nude (Tacoma) | | |
|---|---|---|---|
| Tumor Inoculation: | Cervical MS-751, C33A | | |
| | 5*10^6 (s.c.) in 30% MG | | |
| Drug: | MM-398 (iv) + Veliparib (oral) | | |

| Groups: | | Animal per group: | Dose (mpk) | |
|---|---|---|---|---|
| 1 | Saline | 10 | | |
| 2 | MM-398 | 10 | 5 | |
| 3 | veliparib/oral | 10 | 50 | 3/4/5th day |
| 4 | MM-398 + veliparib | 10 | 5 + 50 | 3/4/5th day |

Figure 9A:
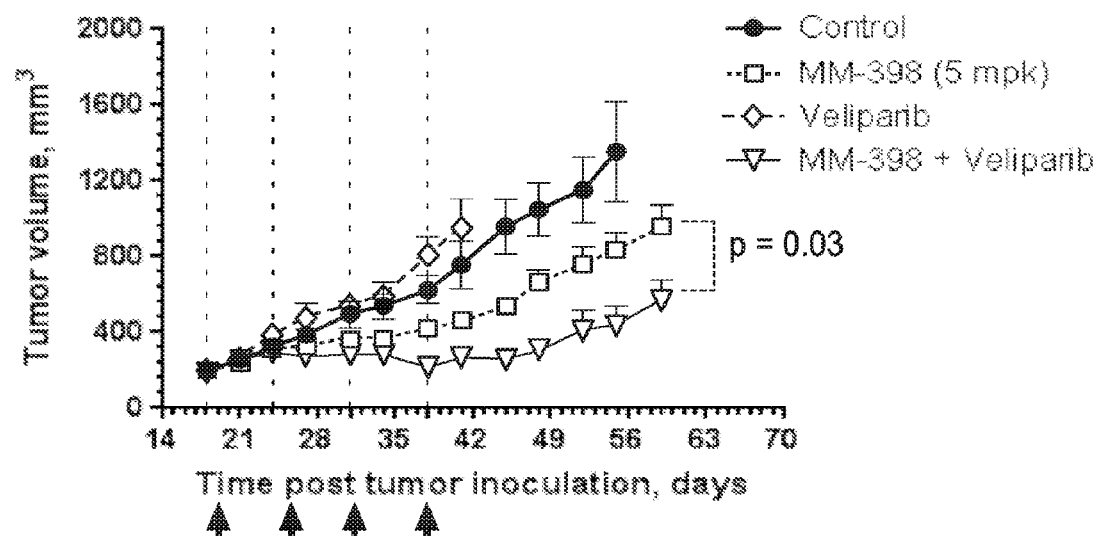
FIG. 9A is a graph showing data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9B:
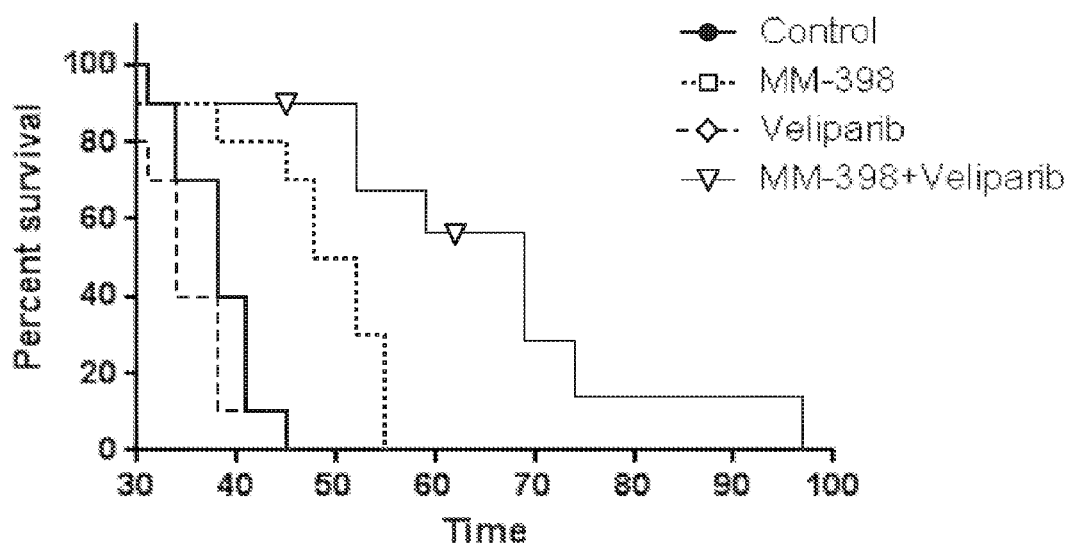
FIG. 9B is a graph showing survival data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9C:
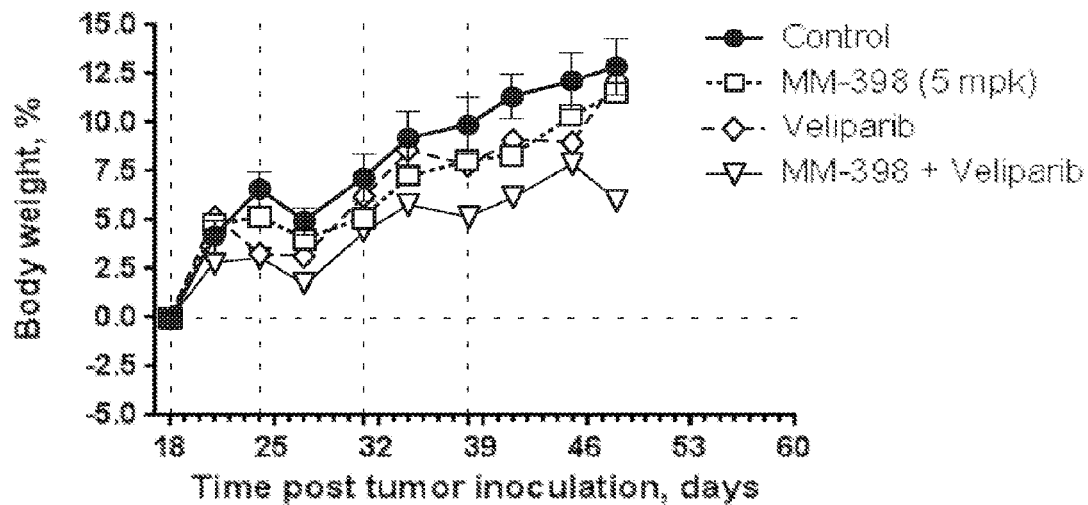
FIG. 9C is a graph that depicts the effect of MM-398 in combinations with veliparib in MS751 xenograft murine model treated with liposomal irinotecan (5 mg/kg MM398) and/or the PARP inhibitor veliparib (50 mpk) on days 3-5 starting after administration of MM398.

FIG. 9A shows that tumor volume decreased when MM-398 (5 mpk dose) was administered in combinations with veliparib in the MS751 xenograft model (p=0.03) as compared to administration of either drug alone. FIG. 9B shows that percent survival was better for mice treated with MM-398 (5 mpk dose) in combinations with veliparib in MS751 xenograft model as compared to treatment with either drug alone either drug administered alone. FIG. 9C shows that treatment with the combination of MM-398 with veliparib in MS751 xenograft model lead to decreases in body weight as compared to administration of either drug alone.

C33A Cervical Xenograft Model

The C33A Xenograft Model details are summarized in Table 7.

TABLE 7

Mice: Female, Ncr Nudes (Taconic), 5-6 weeks.
Cell Lines: C33A
Tumor Inoculation: 5 × $10^6$ in 100 µl Matrigel (30 vol %) sc
15 mice per a cell line

| Groups: | Dose, mpk: |
|---|---|
| MM-398 alone | 2 |
| Veliparib alone | 50 |
| MM-398 + Veliparib (3-4-5 d) | 2 + 60 |

End-life Collection: 72 h after first injection

Frozen (Tumor, Liver, Spleen, Plasma)
FFPA (Tumor)
Analysis:

gamma H2AX and cleaved caspase/Tunnel in FFPE (Lia)
CPT-11 and SN-38 in all tissues for MM-398 flash frozen only (Roswell)

Figure 10:
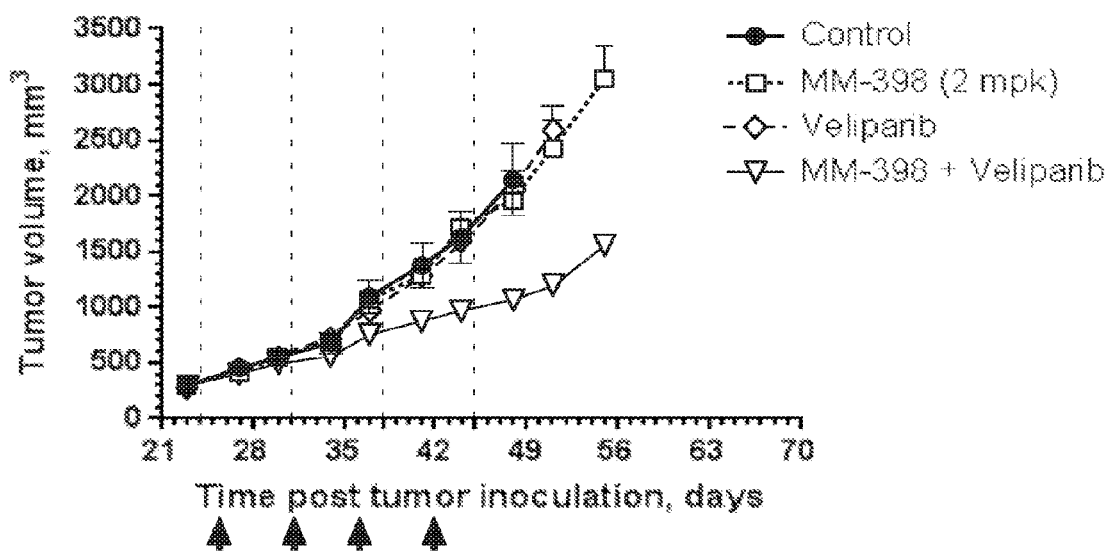
FIG. 10 is a graph showing data from a mouse xenograft study using C33 cervical cancer cells in a murine model treated with liposomal irinotecan (2 mg/kg MM398) and/or the PARP inhibitor veliparib (50 mpk) on days 3-5 starting after administration of MM398.
Figure 11:
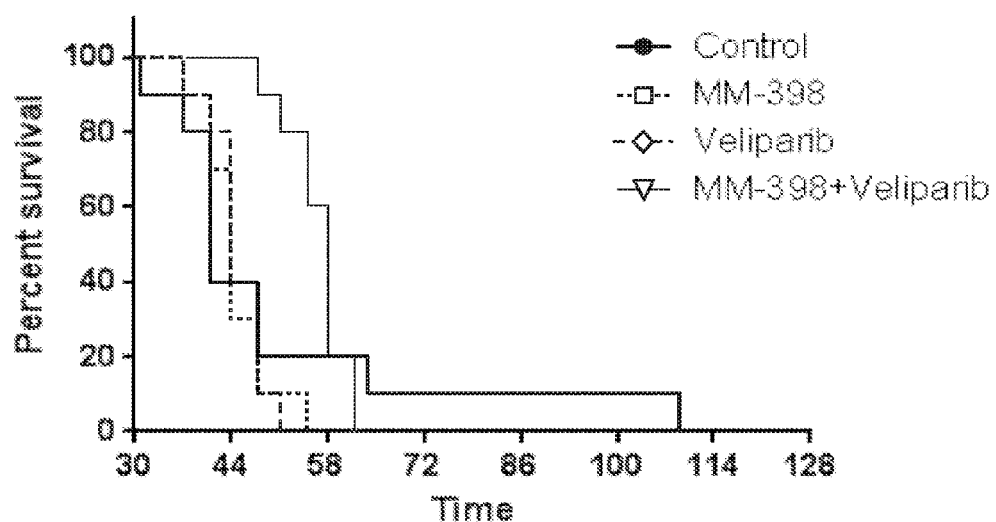
FIG. 11 is a graph showing survival data from a mouse xenograft study using C33 cervical cancer cells in a murine model treated with liposomal irinotecan (5 mg/kg MM398) and/or the PARP inhibitor veliparib (50 mpk) on days 3-5 starting after administration of MM398.

FIG. 10 shows that the combination of MM-398 with veliparib in the C33A xenograft model leads to decreases in tumor volume as compared to either drug alone administered alone. FIG. 11 shows that percent survival was better for mice MM-398 (5 mpk dose) in combinations with veliparib in C33A xenograft model as compared to either drug administered alone.

Example 5: Clinical Use of Liposomal Irinotecan and PARP Inhibitors

Clinical Use of Liposomal Irinotecan and Veliparib

This is a Phase 1 human dose escalation study to characterize the safety, tolerability, MTD and PK of MM-398 in combination with veliparib in order to determine an optimal combination dose and schedule that will be identified as the recommended Phase 2 dose. The following schematic outlines two different schedules of veliparib dosing that will be explored in combination with MM-398 bi-weekly dosing:

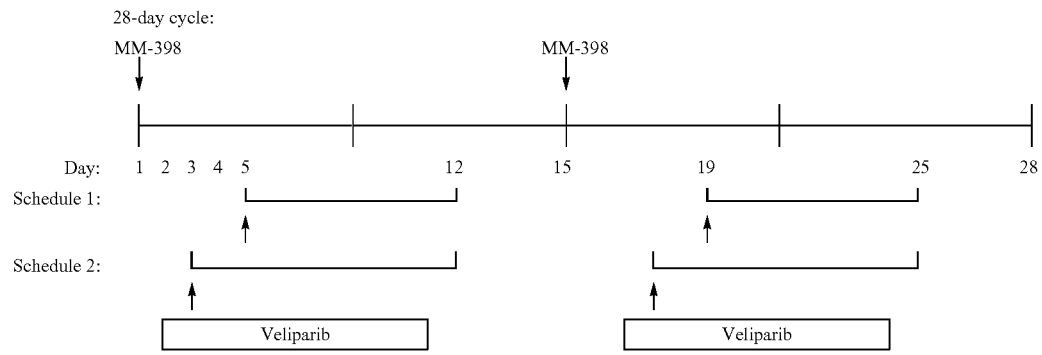

MM-398 will be administered by intravenous (IV) infusion over 90 minutes at a dose of 80 mg/m² every two weeks. MM-398 is administered by intravenous (IV) infusion over 90 minutes at a dose of 80 mg/m² (salt) irinotecan once every two weeks (days 1 and 15 of each 28-day treatment cycle). Veliparib is co-administered orally twice daily by the patient at home according to the following schedule:

TABLE 8

| Dose Level[1] | Veliparib Dose (mg BID) | Veliparib Dose Days | MM-398 Dose (salt) (mg/m² q2w) |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

[1]Additional dose levels and alternate dosing schedules may be explored upon agreement of Sponsor, Medical Monitor and Investigators.
** After the MTD is reached, and for the first cycle only, we plan to enroll approximately 18 patients obtain tumor biopsies according to the schema outlined in the correlates section below.

The study will enroll 3 patients per dose cohort following a traditional 3+3 dose escalation design. Dose limiting toxicities (DLTs) will be evaluated during the first cycle of treatment (28 days) in order to determine the MTD. If there are no DLTs within the safety evaluation period, then the next cohort can be initiated following agreement between the Investigators and Medical Monitor. If a DLT occurs, then the cohort will be expanded to 6 patients. If 2 or more patients have DLTs within a given dose level, then the dose will not be escalated further; however, lower doses may be explored. Additional dosing schedules may also be explored depending on the safety, tolerability, and PK observed.

Given that these individual therapies have been studied in previous clinical trials, it is important that the safety assessment takes into account the expected safety profile of the standard dose regimens. For all treatment regimens, any toxicity that is related to disease progression will not be considered a DLT. The following events, occurring during cycle 1 of the study combination, will be considered DLTs if deemed drug-related:

grade 3 or 4 neutropenia complicated by fever ≥38.5° C. (i.e. febrile neutropenia) and/or documented infection;

grade 4 neutropenia that does not resolve within 7 days despite optimal therapy (withholding study drug and GCSF administration);

grade 4 thrombocytopenia that does not resolve within 7 days or any grade 3-4 thrombocytopenia complicated with hemorrhage;

grade 4 anemia that does not resolve within 7 days despite optimal therapy (withholding study drug and red blood cell transfusions);

inability to begin subsequent treatment course within 14 days of the scheduled date, due to study drug toxicity;

any grade 3-4 non-hematologic toxicity (except fatigue/asthenia <2 weeks in duration; vomiting or diarrhea lasting less than 72 hours whether treated with an optimal anti-emetic or anti-diarrheal regimen or not; or alkaline phosphatase changes).

≥grade 2 seizure

Patients will be treated until disease progression as determined by RECIST v1.1 criteria evaluated by CT scan every 8 weeks from first dose of study drug. The inclusion and exclusion criteria for the clinical trial are summarized in the table 9 below.

TABLE 9

| Inclusion Criteria | Exclusion Criteria |
|---|---|
| Patients must have histologic or cytologic confirmation of cancer for which there is no known standard therapy capable of extending life expectancy. | Active CNS metastasis |
| | Clinically significant GI disorders, including history of small bowel obstruction unless the obstruction |
| ECOG Performance Status 0 or 1 | was a surgically treated remote |
| Tumor lesion(s) amenable to multiple pass percutaneous biopsies and patient willing to undergo required pre- and post-treatment biopsies | episode |
| | Prior irinotecan therapy; or topotecan therapy or bevacizumab therapy within 6 months of first dose of study treatment |
| Must have adequate: | |
| Bone marrow function | Prior chemotherapy or biological |
|     ANC >1,500 cells/µl without the use of hematopoietic growth factors | therapy within 3 weeks, or within a time interval less than 5 half-lives of the agent, prior to first dose of study |
|     Platelet count >100,000 cells/µl | treatment |
|     Hemoglobin >9 g/dL | Prior radiotherapy within 4 weeks of |
| Hepatic function | first dose of study treatment |
|     Normal serum total bilirubin | Patients who have had radiation to |
|     AST and ALT ≤2.5 × ULN (≤5 × ULN is acceptable if liver metastases are present) | the pelvis or other bone marrow-bearing sites will be considered on a case by case basis and may be |
| Renal function | excluded if the bone marrow reserve |
|     Serum creatinine ≤1.5 × ULN | is not considered adequate (i.e. |
| Normal ECG | radiation to >25% of bone marrow) |
| ≥18 years of age | Known hypersensitivity to MM-398 |

TABLE 9-continued

| Inclusion Criteria | Exclusion Criteria |
|---|---|
| Able to understand and sign informed consent | Active infection |
| Prior PARP inhibitor therapy is allowed | Pregnant or breast feeding |
| Willing to undergo pre-treatment ferumoxytol MRI (patients will be excluded from undergoing ferumoxytol MRI if they have evidence of iron overload, a known hypersensitivity to ferumoxytol or any other IV iron product, a documented history of multiple drug allergies, or those for whom MRI is otherwise contraindicated, including claustrophobia or anxiety related to undergoing MRI) | |

The dose escalation portion of the trial may require up to 30 patients if 6 patients are required at each of 5 dose levels. An additional 18 patients may be used to explore the effect of veliparib on the biologic correlates. Thus, the accrual ceiling will be set at 48 patients.

The study is proposed to include all solid tumor types, however, particular indications that are of high interest for this study includes the following: cervical cancer, ovarian cancer, triple negative breast cancer (TNBC), non-small cell lung cancer (NSCLC), small cell lung cancer (SCLC), gastric cancer, pancreatic cancer, and neuroendocrine tumors.

The methods and uses herein can also be applied to other tumor suitable types including those noted for increased frequency of DNA damage response (DDR) pathway deficiencies (or 'BRCAness') found in sporadic tumors, which are predicted to be sensitive to PARP inhibitors. As mentioned previously, BRCA1 or BRCA2 deficiencies, found particularly in triple negative breast cancer and high-grade serous ovarian cancer, sensitize cells to PARP-inhibitors. Likewise, loss of function of other genes and proteins involved in DDR pathways, including the endonuclease XPF-ERCC1, the homologous recombination repair proteins meiotic recombination protein 11 (MRE11) and Fanconi anemia pathway (FANC) proteins, also sensitize cells to PARP inhibitors. Fanconi anemia pathway deficiencies have been demonstrated in lung, cervical, and breast and ovarian cancers. These and other DDR pathway deficiencies may be predictive biomarkers for PARP inhibitor therapy, and will be explored retrospectively in this study. Veliparib, specifically, has also demonstrated clinical activity in a number of indications, including BRCA-positive and BRCA wild-type breast and ovarian cancer, as well as gastric cancer in combination with FOLFIRI. For the proposed study, indications were chosen not only for their high unmet medical need, but for potential sensitivity to irinotecan and/or veliparib based on the afore-mentioned pre-clinical and/or clinical experience. While the PARP inhibitor olaparib has recently been FDA approved as a monotherapy in BRCA+ ovarian cancer, this study will not limit treatment in the ovarian patient population to BRCA+ patients, as this is a phase I study of a combination therapy and may retrospectively identify patients with other DDR pathway deficiencies in addition to BRCA.

Use of Liposomal Irinotecan and Olaparib

MM-398 is administered by intravenous (IV) infusion over 90 minutes at a dose of 80 mg/m² (based on the corresponding amount of irinotecan hydrochloride trihydrate, equivalent to 70 mg/m² irinotecan free base) every two weeks. Olaparib is co-administered orally twice daily by the patient at home according to the following schedule (Table 10).

TABLE 10

| Dose Level[1] | Olaparib Dose (mg BID) | Olaparib Dose Days | MM-398 Dose (mg/m² q2w)* |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

*= The 80 mg/m² MM-398 dose is based on the corresponding amount of irinotecan hydrochloride trihydrate (equivalent to 70 mg/m² based on irinotecan free base).

Example 6: Measuring Phosphorylated H2AX in Tumor Biopsies

Figure 14:
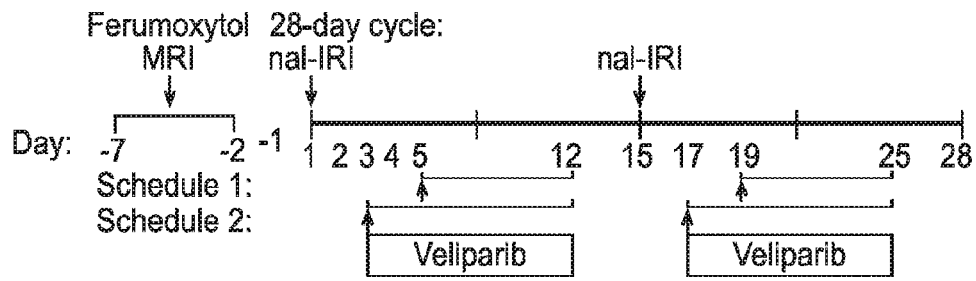
FIG. 14 is a graphical representation of a phase I study design employing the combinations of MM-398 (nal-IRI) and veliparib.

Phosphorylated H2AX (γ-H2AX) plays an important role in the recruitment and/or retention of DNA repair and checkpoint proteins such as BRCA1, MRE11/RAD50/NBS1 complex, MDC1 and 53BP1. DNA damage has been shown to increase H2AX phosphorylation in cancer cells following exposure to camptothecins. If the PARP inhibitor compound(s) is/are able to increase the degree of DNA damage due to irinotecan from MM-398, it may be detectable by measurement of H2AX phosphorylation. An immunofluorescence assay was used in previous clinical studies. Patient peripheral blood mononuclear cells (PBMCs), hair follicles, and/or tumor biopsy samples will be collected if there is readily accessible disease. The association between the pharmacodynamic response measured by γ-H2AX level can be assessed by Fisher's test or the Wilcoxon rank sum test, as appropriate; this evaluation will be done at the MTD+/−a maximum of 2 dose levels (FIG. 14).

TABLE 11

Schedule for biopsies and surrogate samples

| Dose Level | PARPi Dose (mg BID) | PARPi Dose Days | MM-398 Dose (mg/m² q2w) | Biopsy in am for PD marker |
|---|---|---|---|---|
| 1 | 100 | Day 5-12; 19-25 | 80, Day 1, 15 | — |
| 2 | 200 | Day 5-12; 19-25 | 80, Day 1, 15 | — |
| 3 | 200 | Day 3-12; 17-25 | 80, Day 1, 15 | Days 1, 5, 19 |

TABLE 11-continued

Schedule for biopsies and surrogate samples

| Dose Level | PARPi Dose (mg BID) | PARPi Dose Days | MM-398 Dose (mg/m² q2w) | Biopsy in am for PD marker |
|---|---|---|---|---|
| 4 | 300 | Day 3-12; 17-25 | 80, Day 1, 15 | Days 1, 5, 19 |
| 5 | 400 | Day 3-12; 17-25 | 80, Day 1, 15 | Days 1, 5, 19 |
| Con-firm A | MTD | Day 3-12; 19-25 | 80, Day 1, 15 | Days 1, 5, 19 |
| B | MTD | Day 5-12; 17-25 | 80, Day 1, 15 | Days 1, 5, 19 |

Figure 15A:
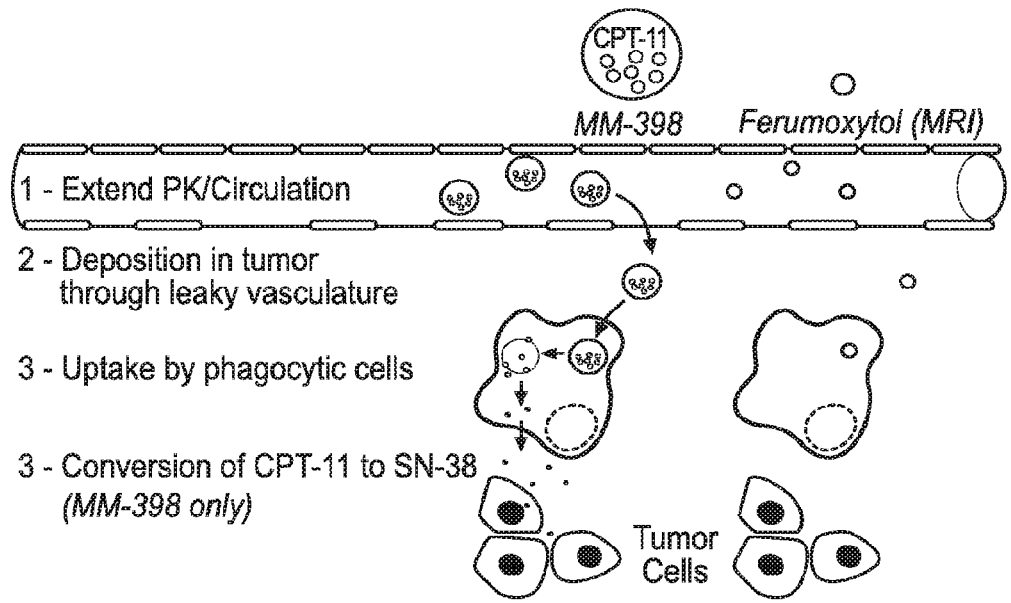
FIG. 15A is a schematic showing a use of ferumoxytol (FMX) as a predictive biomarker for cancer treatment with liposomal irinotecan (e.g., MM-398).
Figure 15B:
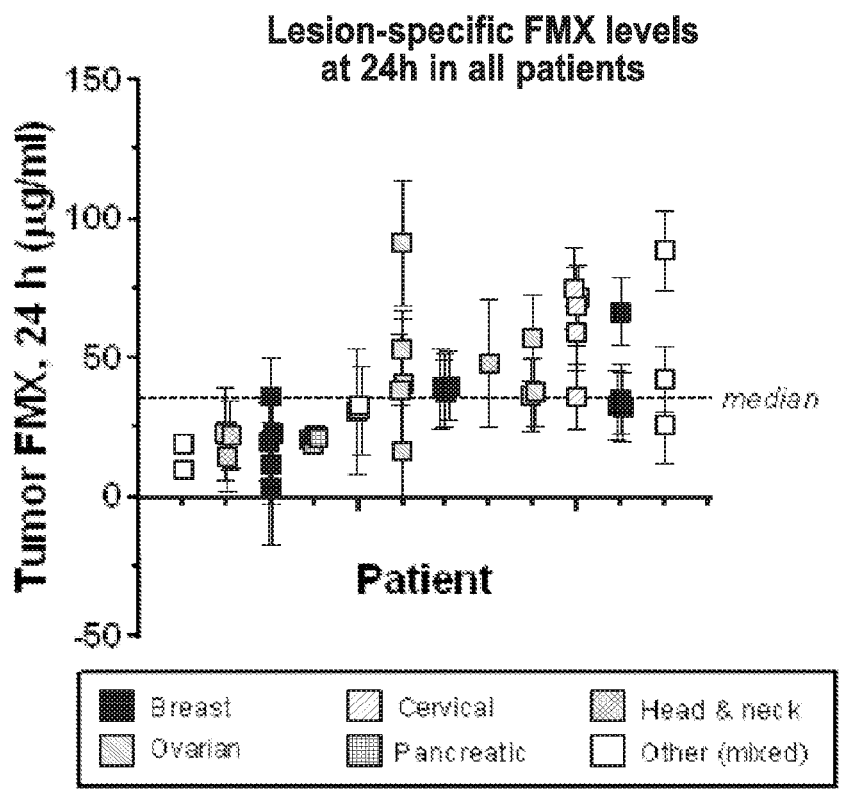
FIG. 15B is a graph showing FMX concentration of individual patient lesions was calculated using a standard curve from MR images obtained 24 h post-FMX injection.
Figure 15C:
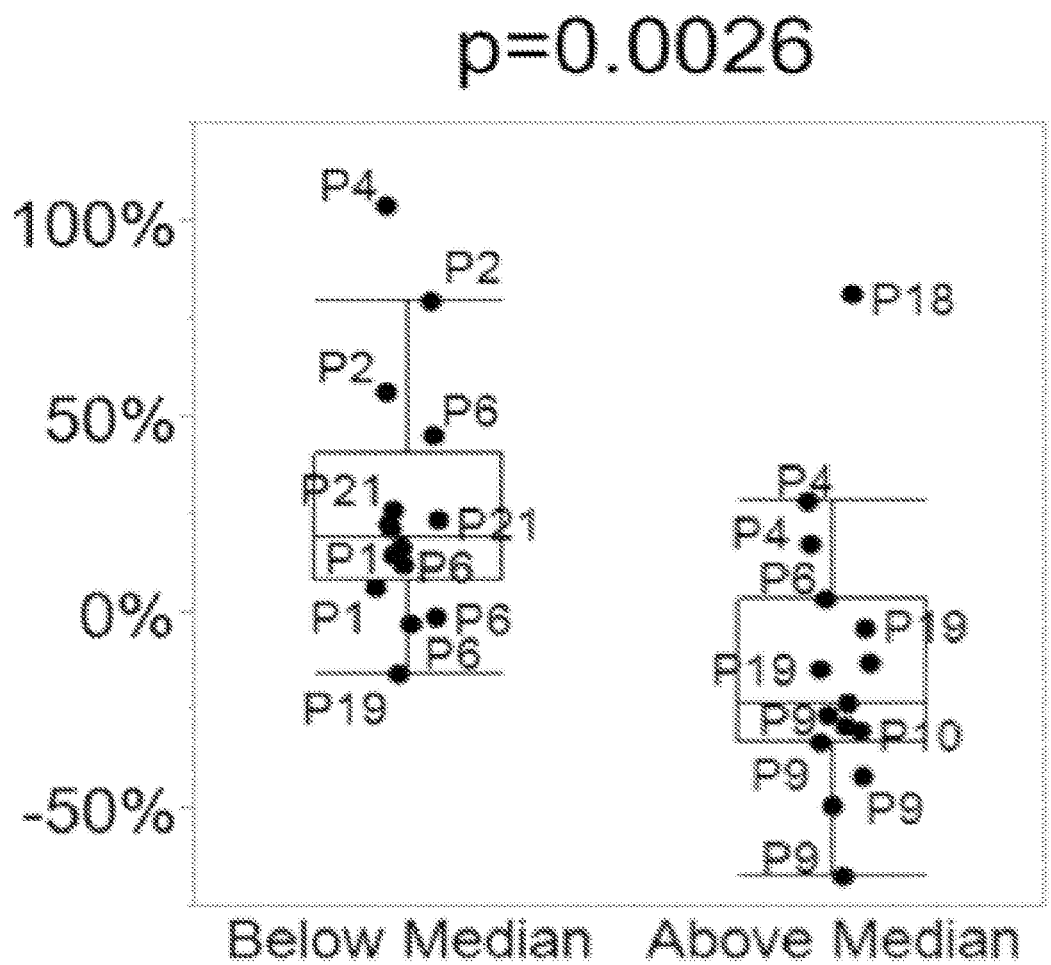
FIG. 15C is a graph showing FMX signal from lesions at 24 h are grouped relative to the median value observed in the FMX MRI evaluable lesions and compared to the best change in lesion size based on CT scans (data available from 9 patients; total of 31 lesions).

Example 7: Administering and Detecting Ferumoxytol to Predict Deposition of Topoisomerase Inhibitor from Liposomal Irinotecan FIGS. 15A-15C show that FMX MRI may be a predictive tool for tumor response to MM-398. FIG. 15A is a schematic showing that MM-398 and FMX have similar properties, including 1) extended PK, 2) the ability to deposit in tumor tissues through the EPR effect (i.e. leaky vasculature), and 3) uptake by macrophages. Therefore, visualization of FMX on MRI may be able to predict MM-398 deposition. (B) FMX concentration of individual patient lesions was calculated using a standard curve from MR images obtained 24 h post-FMX injection. (C) FMX signal from lesions at 24 h are grouped relative to the median value observed in the FMX MRI evaluable lesions and compared to the best change in lesion size based on CT scans (data available from 9 patients; total of 31 lesions).

The phase I study of MM-398 also examined the feasibility of magnetic resonance (MR) imaging to predict tumor-associated macrophage (TAM) content and MM-398 deposition. TAMs appear to play a key role in the deposition, retention and activation of MM-398 within the tumor microenvironment. In this clinical study, ferumoxytol (FMX) a microparticulate preparation of a superparamagnetic iron oxide coated with polyglucose sorbitol carboxymethylether) was used as an imaging contrast agent and MR images were obtained at 1 h, 24 h, and 72 h following FMX injection. FMX is an approved therapy that is indicated for the treatment of iron deficiency anemia in adult patients with chronic kidney disease; however a growing number of cancer patients without iron deficiency are being administered FMX as an imaging agent to visualize macrophage content and vasculature. Like MM-398, FMX is also a nanoparticle with a diameter of approximately 17-31 nm. As tumor permeability was predicted to be an important factor in MM-398 efficacy, FMX was also investigated for use as a surrogate for liposome deposition (FIG. 15A). A benefit of FMX is that this agent helps to identify patients that are less likely to respond to MM-398 because of poor drug uptake. Ferumoxytol as a diagnostic test enables the detection of a patient population that would significantly benefit from MM-398 that would otherwise be uncategorized.

The MRI results from a human clinical trial study demonstrated that the amount of FMX depositing in tumor lesions was able to be quantified (FIG. 15B), and it was subsequently shown that a correlation existed between tumor lesion ferumoxytol uptake by MRI and response to MM-398 (FIG. 15C). This correlation is now being studied further in an expansion of the Phase 1 study, and is included as a correlative imaging study for a trial of MM-398+veliparib.

FMX is an iron replacement product indicated for the treatment of iron deficiency anemia in adult patients with chronic kidney disease. Although not approved as an indication, ferumoxytol has also been used as an imaging agent in cancer patients and will be utilized as such in this study. At least 2 days prior to Cycle 1 Day 1 (maximum of 8 days prior) a single dose of 5 mg/kg FMX will be administered by intravenous injection. The total single dose will not exceed 510 mg, the maximum approved single dose of FMX. This dosing schedule is less intense than the approved label, which recommends two doses of 510 mg 3 to 8 days apart; however since FMX is being used as imaging agent in this study as opposed to a replacement product for iron deficiency, a lower dose is more appropriate. Three MRIs will be performed for each patient over 2 days. All patients will have a baseline image acquired prior to the FMX infusion, and a second image acquired 1-4 h after the end of FMX administration. All patients will return the following day for a 24 h FMX-MRI using the same protocol and sequences as previously. Each patient will be required to complete their FMX-MRIs on the same scanner to reduce inter-scan variability. The body area to be scanned will be determined by the location of the patient's disease. Each MRI study will be evaluated for image quality and signal characteristics of tumors and reference tissue on T1-, T2- and T2*-weighted sequences. Once a completed set of images from each patient has been received, a qualitative review will be performed and sent to a quantitative lab for analysis. The data will be analyzed in a similar fashion as described above.

TABLE 12

Imaging Correlates

| Correlative Objective | Imaging Technique | Organ(s) Scanned and Timing of Scans |
|---|---|---|
| Ferumoxytol (FMX) uptake | MRI | Sites of disease; 3 scans completed approximately 2-6 days prior to Cycle 1 Day 1. Scan time points: baseline (immediately prior to FMX infusion) 1 h (post-FMX infusion) 24 h (post-FMX infusion) |
| Histone gamma-H2AX (Pommier, DTB-CCR; Doroshow, Leidos) | Immunofluorescence microscopy ELISA (in development) | Tumor biopsy before treatment, and during treatment. Hair follicles during treatment. PBMC before treatment and during treatment |

Imaging Correlate Study

Patients will be eligible to participate in the FMX imaging study if they do not meet any of the following criteria:
- Evidence of iron overload as determined by:
  - Fasting transferrin saturation of >45% and/or
  - Serum ferritin levels >1000 ng/ml
- A history of allergic reactions to any of the following:
  - compounds similar to ferumoxytol or any of its components as described in full prescribing information for ferumoxytol injection
  - any IV iron replacement product (e.g. parenteral iron, dextran, iron-dextran, or parenteral iron polysaccharide preparations)
  - multiple drugs
- Unable to undergo MRI or for whom MRI is otherwise contraindicated (e.g. presence of errant metal, cardiac pacemakers, pain pumps or other MRI incompatible devices; or history claustrophobia or anxiety related to undergoing MRI)

If a patient consents to FMX-MRI, the patient will receive ferumoxytol infusion and undergo the required FMX-MRI scans approximately 2-6 days prior to beginning MM-398 treatment (the FMX period). FMX will be administered at a dose of 5 mg/kg up to a maximum of 510 mg. All other aspects of administration will be consistent with the latest ferumoxytol prescribing information. A detailed FMX-MRI protocol will be included in the study imaging manual. Briefly, each patient will be required to complete their FMX-MRIs on the same scanner to reduce inter-scan variability. Each MRI study will be evaluated for image quality and signal characteristics of tumors and reference tissue on T1-, T2- and T2*-weighted sequences. Once a completed set of images from each patient has been received, the images will be loaded onto the viewing workstation for qualitative review and then sent to a quantitative lab (handled by central imaging CRO) for analysis.

Multiple MR images will be collected on Day 1-Day 2 of the FMX period at various time points: a baseline image acquired prior to the FMX infusion, a second image occurring 1-4 h after the end of FMX administration, and a third image at approximately 24 h post-FMX, using the same protocol and sequences as on Day 1. The body areas to be scanned will be determined by the location of the patient's disease; detailed instructions will be described in the study imaging manual.

Example 8: Clinical Use of Liposomal Irinotecan in Combination with 5-Fluorouracil and Leucovorin Clinical efficacy of MM-398 has also been demonstrated in gemcitabine-refractory metastatic pancreatic cancer patients: in a randomized, Phase 3, international study (NAPOLI-1), MM-398 was given in combination with 5-fluorouracil/leucovorin (5-FU/LV) and significantly prolonged overall survival (OS) compared to 5-FU/LV treatment alone. The median OS for the MM-398-containing arm was 6.1 months compared to 4.2 months for the control arm (HR=0.67, p=0.0122). Because the active pharmaceutical ingredient in MM-398 is irinotecan, the safety profile was, as anticipated, qualitatively similar to irinotecan, where the most common adverse events (≥30%) are nausea, vomiting, abdominal pain, diarrhea, constipation, anorexia, neutropenia, leukopenia (including lymphocytopenia), anemia, asthenia, fever, body weight decreasing, and alopecia (irinotecan package insert). Table 14 provides a summary of Grade 3 or higher safety data of patients treated with MM-398 plus 5-FU/LV from the NAPOLI-1 study. Table 13 provides toxicities observed in the Phase I monotherapy study, for comparison.

TABLE 13

Summary of the most common (>10%) grade 3 or greater adverse events from the 13 patients treated with MM-398 monotherapy at a dose of 80 mg/m² every 2 weeks during the phase I study. Adverse Events ≥ Grade 3 in Study MM-398-01-01-02

|  | n (%) |
| --- | --- |
| Diarrhea | 4 (30.8) |
| Hypokalemia | 3 (23.1) |
| Abdominal pain | 2 (15.4) |
| Anemia | 2 (15.4) |
| Nausea | 2 (15.4) |
| Neutropenia | 2 (15.4) |

TABLE 14

Summary of Grade 3 or higher AEs from the NAPOLI-1 phase III study.

|  | MM-398 + 5-FU/LV[1] (N = 117) % | 5-FU/LV[2] (N = 134) % |
| --- | --- | --- |
| GRADE ≥3 NON-HEMATOLOGIC AEs IN >5% PATIENTS, %[3] | | |
| Fatigue | 14 | 4 |
| Diarrhea | 13 | 5 |
| Vomiting | 11 | 3 |
| Nausea | 8 | 3 |
| Asthenia | 8 | 7 |
| Abdominal pain | 7 | 6 |
| Decreased appetite | 4 | 2 |
| Hypokalemia | 3 | 2 |
| Hypernatremia | 3 | 2 |
| GRADE ≥3 HEMATOLOGIC AES BASED ON LABORATORY VALUES, %[3,4] | | |
| Neutrophil count decreased | 20 | 2 |
| Hemoglobin decreased | 6 | 5 |
| Platelet count decreased | 2 | 0 |

[1]Dose: 80 mg/m² MM-398 + 2400 mg/m² over 46 h/400 mg/m² 5-FU/LV q2w
[2]Dose: 2000 mg/m² over 24 h/200 mg/m² 5-FU/LV weekly x 4, q6w
[3]Per CTCAE Version 4
[4]Includes only patients who had at least one post-baseline assessment

Example 9: Cell Survival for Various TNBC Cell Lines Following SN-38 and PARP Inhibitor Combination Treatment Tables 15a, 15b, 16a, and 16b provide the results of in vitro measurements of cell survival for various triple negative breast cancer (TNBC) cancer cell lines to determine the cell viability following treatment with SN-38 and/or a PARP inhibitor. Tables 15a and 15b provide IC50 data, and Tables 16a and 16b provide Maximum Kill data.

TABLE 15a

IC50 log10 (μM)

Exp. 1

| Treatment | Cell Line | | |
|---|---|---|---|
| | BT20 | SUM159PT | HCC38 |
| SN38 | −0.18 | −2.35 | −2.80 |
| Niraparib | 2.14 | 0.35 | 1.23 |
| SN38 & Niraparib (3 ug/ml) | −0.67 | −3.99 | −0.12 |
| SN38 & Niraparib (1 ug/ml) | −0.70 | −3.42 | −4.09 |
| SN38 & Niraparib (0.3 ug/ml) | −0.71 | −2.85 | −4.23 |
| SN38 & Niraparib (0.1 ug/ml) | −0.61 | −2.87 | −4.05 |

Exp. 2

| Treatment | Cell Line | | |
|---|---|---|---|
| | BT20 | SUM149PT | SUM159PT |
| SN38 | −0.69 | 0.24 | −2.39 |
| Olaparib | 1.24 | 2.40 | 0.18 |
| SN38 & Olaparib (3 ug/ml) | −1.48 | −0.19 | −3.70 |
| SN38 & Olaparib (1 ug/ml) | −1.49 | −0.34 | −3.31 |
| SN38 & Olaparib (0.3 ug/ml) | −1.44 | −0.18 | −2.92 |
| SN38 & Olaparib (0.1 ug/ml) | −1.29 | −0.11 | −2.92 |

Exp. 3

| Treatment | Cell Line | | |
|---|---|---|---|
| | BT20 | SUM149PT | SUM159PT |
| SN38 | −0.37 | 0.27 | −2.66 |
| Rucaparib | 1.27 | 1.68 | −0.07 |
| SN38 & Rucaparib (3 ug/ml) | −1.33 | −0.16 | −3.64 |
| SN38 & Rucaparib (1 ug/ml) | −1.47 | −0.23 | −3.28 |
| SN38 & Rucaparib (0.3 ug/ml) | −1.48 | −0.49 | −3.23 |
| SN38 & Rucaparib (0.1 ug/ml) | −1.24 | −0.10 | −3.11 |

Exp. 4

| Treatment | Cell Line | | |
|---|---|---|---|
| | BT20 | SUM159PT | HCC38 |
| SN38 | −0.24 | −2.33 | −2.75 |
| Talazoparib | 1.45 | −1.03 | −1.23 |
| SN38 & Talazoparib (3 ug/ml) | −1.88 | −4.01 | −3.41 |
| SN38 & Talazoparib (1 ug/ml) | −1.70 | −4.01 | −4.01 |
| SN38 & Talazoparib (0.3 ug/ml) | −1.10 | −4.01 | −5.46 |
| SN38 & Talazoparib (0.1 ug/ml) | −1.36 | −4.01 | −2.87 |

TABLE 15b

IC50 log10 (μM)

Exp. 1

| Treatment | Cell Line | | |
|---|---|---|---|
| | HCC1187 | HCC1806 | BT549 |
| SN38 | −0.68 | −2.08 | −0.10 |
| Niraparib | 2.11 | 1.27 | 2.03 |
| SN38 & Niraparib (3 ug/ml) | −1.58 | −2.80 | −0.39 |
| SN38 & Niraparib (1 ug/ml) | −1.45 | −2.62 | −0.64 |
| SN38 & Niraparib (0.3 ug/ml) | −1.61 | −2.55 | −0.74 |
| SN38 & Niraparib (0.1 ug/ml) | −1.41 | −2.52 | −0.55 |

Exp. 2

| Treatment | Cell Line | | |
|---|---|---|---|
| | HCC70 | HCC1187 | BT549 |
| SN38 | −0.07 | −0.64 | −0.04 |
| Olaparib | $-4.2 \times 10^7$ | 2.41 | 2.04 |
| SN38 & Olaparib (3 ug/ml) | −0.58 | −1.77 | −0.55 |
| SN38 & Olaparib (1 ug/ml) | −0.49 | −1.67 | −0.48 |
| SN38 & Olaparib (0.3 ug/ml) | −0.50 | −1.35 | −0.35 |
| SN38 & Olaparib (0.1 ug/ml) | −0.48 | −1.56 | −0.04 |

Exp. 3

| Treatment | Cell Line | | |
|---|---|---|---|
| | HCC38 | HCC1954 | BT549 |
| SN38 | −2.89 | −0.97 | −0.05 |
| Rucaparib | −0.07 | 1.60 | 1.75 |
| SN38 & Rucaparib (3 ug/ml) | 4.93 | −1.22 | −0.48 |
| SN38 & Rucaparib (1 ug/ml) | −3.88 | −1.33 | −0.57 |
| SN38 & Rucaparib (0.3 ug/ml) | −4.01 | −1.51 | −0.49 |
| SN38 & Rucaparib (0.1 ug/ml) | −3.29 | −1.57 | −0.52 |

Exp. 4

| Treatment | Cell Line | | |
|---|---|---|---|
| | HCC1187 | HCC1954 | SKBR3 |
| SN38 | −0.98 | −0.65 | −1.38 |
| Talazoparib | 2.28 | 3.64 | $-2.8 \times 10^4$ |
| SN38 & Talazoparib (3 ug/ml) | −1.79 | −1.64 | −2.05 |
| SN38 & Talazoparib (1 ug/ml) | −1.79 | −1.51 | −2.65 |
| SN38 & Talazoparib (0.3 ug/ml) | −1.94 | −1.45 | −2.23 |
| SN38 & Talazoparib (0.1 ug/ml) | −1.92 | −1.29 | −2.41 |

TABLE 16a

Maximum Kill Percent

Exp. 1

| Treatment | Cell Line | | |
|---|---|---|---|
| | BT20 | SUM159PT | HCC38 |
| SN38 | 100 | 97 | 96 |
| Niraparib | 100 | 97 | 100 |
| SN38 & Niraparib (3 ug/ml) | 100 | 100 | |
| SN38 & Niraparib (1 ug/ml) | 100 | 100 | 93 |
| SN38 & Niraparib (0.3 ug/ml) | 100 | 99 | 100 |
| SN38 & Niraparib (0.1 ug/ml) | 100 | 100 | 100 |

Exp. 2

| Treatment | Cell Line | | |
|---|---|---|---|
| | BT20 | SUM149PT | SUM159PT |
| SN38 | 100 | 96 | 97 |
| Olaparib | 98 | 100 | 94 |
| SN38 & Olaparib (3 ug/ml) | 98 | 97 | 100 |
| SN38 & Olaparib (1 ug/ml) | 99 | 96 | 97 |
| SN38 & Olaparib (0.3 ug/ml) | 100 | 98 | 99 |
| SN38 & Olaparib (0.1 ug/ml) | 100 | 96 | 99 |

Exp. 3

| Treatment | Cell Line | | |
|---|---|---|---|
| | BT20 | SUM149PT | SUM159PT |
| SN38 | 100 | 95 | 99 |
| Rucaparib | 100 | 99 | 97 |
| SN38 & Rucaparib (3 ug/ml) | 92 | 97 | 99 |
| SN38 & Rucaparib (1 ug/ml) | 100 | 97 | 99 |
| SN38 & Rucaparib (0.3 ug/ml) | 94 | 95 | 100 |
| SN38 & Rucaparib (0.1 ug/ml) | 96 | 100 | 97 |

Exp. 4

| Treatment | Cell Line | | |
|---|---|---|---|
| | BT20 | SUM159PT | HCC38 |
| SN38 | 100 | 96 | 92 |
| Talazoparib | 100 | 94 | 92 |
| SN38 & Talazoparib (3 ug/ml) | 100 | | |
| SN38 & Talazoparib (1 ug/ml) | 90 | | |
| SN38 & Talazoparib (0.3 ug/ml) | 93 | | |
| SN38 & Talazoparib (0.1 ug/ml) | 93 | | |

TABLE 16b

Maximum Kill Percent

Exp. 1

| Treatment | Cell Line | | |
|---|---|---|---|
| | HCC1187 | HCC1806 | BT549 |
| SN38 | 90 | 93 | 95 |
| Niraparib | 98 | 100 | 100 |
| SN38 & Niraparib (3 ug/ml) | 89 | 91 | 94 |
| SN38 & Niraparib (1 ug/ml) | 93 | 92 | 92 |
| SN38 & Niraparib (0.3 ug/ml) | 89 | 92 | 92 |
| SN38 & Niraparib (0.1 ug/ml) | 89 | 93 | 94 |

Exp. 2

| Treatment | Cell Line | | |
|---|---|---|---|
| | HCC70 | HCC1187 | BT549 |
| SN38 | 97 | 100 | 93 |
| Olaparib | 50 | 87 | 100 |
| SN38 & Olaparib (3 ug/ml) | 98 | 100 | |
| SN38 & Olaparib (1 ug/ml) | 100 | 91 | 96 |
| SN38 & Olaparib (0.3 ug/ml) | 100 | 99 | 94 |
| SN38 & Olaparib (0.1 ug/ml) | 100 | 99 | 96 |

Exp. 3

| Treatment | Cell Line | | |
|---|---|---|---|
| | HCC38 | HCC1954 | BT549 |
| SN38 | 92 | 94 | 94 |
| Rucaparib | 87 | 100 | 100 |
| SN38 & Rucaparib (3 ug/ml) | | 96 | 93 |
| SN38 & Rucaparib (1 ug/ml) | 98 | 94 | 92 |
| SN38 & Rucaparib (0.3 ug/ml) | 98 | 95 | 93 |
| SN38 & Rucaparib (0.1 ug/ml) | 97 | 93 | 94 |

Exp. 4

| Treatment | Cell Line | | |
|---|---|---|---|
| | HCC1187 | HCC1954 | SKBR3 |
| SN38 | 88 | 100 | 88 |
| Talazoparib | | 100 | |
| SN38 & Talazoparib (3 ug/ml) | 89 | 93 | 90 |
| SN38 & Talazoparib (1 ug/ml) | 89 | 94 | 89 |
| SN38 & Talazoparib (0.3 ug/ml) | 89 | 94 | 100 |
| SN38 & Talazoparib (0.1 ug/ml) | 100 | 96 | 87 |

The experiments that generated these data were performed in 384 well format. Cells were plated at 1000 cells/well and then incubated for 24 hours. Then SN-38 and/or one of four different PARP inhibitors (talazoparib niraparib, olaparib or rucaparib) was added and incubated for an additional 24 hours then the wells were washed with PBS to remove the drug and fresh media was added back into the wells. The plates were then allowed to incubate for 72 hours period. After the 72 hour incubation period the media was removed and cell viability was determined using the CellTiter-Glo® cell viability assay (Promega, Madison Wis.) according to the product instructions. FIGS. 3A and 3B are line graphs that depict cell viability in BT20 and HCC38 breast cancer cell lines, respectively, following treatment with SN-38 and/or talazoparib.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every U.S., international or other patent or patent application or publication referred to herein is hereby incorporated herein by reference in its entirety.

The invention claimed is:

1. A method of treating a patient having a solid tumor, the method comprising
    i) administering to the patient liposomal irinotecan once every two weeks; and
    ii) administering a Poly(ADP-ribose) Polymerase (PARP) inhibitor daily for 3 to 10 days between consecutive administrations of the liposomal irinotecan wherein the PARP inhibitor is administered starting at least 2 days after the liposomal irinotecan and ending at least 1 day prior to the administration of additional liposomal irinotecan.

2. The method according to claim 1, wherein each administration of liposomal irinotecan is administered as a dose of 70 mg/m² (free base).

3. The method of claim 2, wherein the patient has been diagnosed with a cancer selected from the group consisting of: cervical cancer, ovarian cancer, triple negative breast cancer (TNBC), non-small cell lung cancer (NSCLC), small cell lung cancer (SCLC), gastric cancer and a neuroendocrine cancer.

4. The method of claim 3, wherein the patient does not have a BRCA1 or a BRCA2 mutation and wherein the PARP inhibitor is selected from the group consisting of niraparib, olaparib, veliparib, rucaparib and talazoparib.

5. The method according to claim 2, wherein the PARP inhibitor is administered on each of consecutive days 5 to 10.

6. The method of claim 5, wherein the patient has been diagnosed with a cancer selected from the group consisting of: cervical cancer, ovarian cancer, triple negative breast cancer (TNBC), non-small cell lung cancer (NSCLC), small cell lung cancer (SCLC), gastrointestinal stromal tumors, gastric cancer, pancreatic cancer, colorectal cancer, and a neuroendocrine cancer.

7. The method of claim 6, wherein the patient does not have a BRCA1 or a BRCA2 mutation and wherein the PARP inhibitor is selected from the group consisting of niraparib, olaparib, veliparib, rucaparib and talazoparib.

8. A method of treating a patient with cancer and having a tumor, the method comprising
    i) administering to the patient an effective amount of liposomal irinotecan, wherein the liposomal irinotecan is a unilamellar lipid bilayer vesicle which encapsulates irinotecan sucrosofate salt and the vesicle comprises 1,2-distearoyl-sn-glycero-3-phosphocholine, cholesterol, and methoxy-terminated polyethylene glycol (MW 2000)-distearoylphosphatidylethanolamine, at a weight ratio of 6.81 mg:2.22 mg:0.12 mg; and
    ii) administering to the patient an effective amount of a PARP inhibitor selected from the group consisting of niraparib, olaparib, veliparib, rucaparib and talazoparib, wherein the PARP inhibitor is administered after an effective irinotecan plasma clearing interval of at least 2 days after the administration of the liposomal irinotecan.

9. The method of claim 8, wherein the effective irinotecan plasma clearing interval is from about 48 to about 120 hours.

10. The method of claim 9, wherein the effective irinotecan plasma clearing interval is 2, 3, 4 or 5 days.

11. The method of claim 10, wherein the patient does not have a BRCA1 or a BRCA2 mutation and wherein the patient has been diagnosed with a cancer selected from the group consisting of: cervical cancer, ovarian cancer, triple negative breast cancer (TNBC), non-small cell lung cancer (NSCLC), small cell lung cancer (SCLC), gastrointestinal stromal tumors, gastric cancer, pancreatic cancer, colorectal cancer, and a neuroendocrine cancer.

12. The method of claim 11, wherein the effective amount of liposomal irinotecan is 70 mg/m² (free base) administered during a 90 minute infusion.

13. The method of claim 12, wherein each administration of the PARP inhibitor is administered at a dose of from about 20 mg/day to about 800 mg/day.

14. A method of treating a patient diagnosed with cancer and having a solid tumor, the method comprising administering to the patient an antineoplastic therapy in a 28-day treatment cycle, the antineoplastic therapy consisting of:
    i) intravenously administering to the patient an effective amount of a liposomal irinotecan antineoplastic agent only on days 1 and 15 of the treatment cycle, the liposomal irinotecan having an irinotecan terminal elimination half-life of about 26.8 hours and a maximal irinotecan plasma concentration of about 38.0 micrograms/ml; and
    ii) administering an effective amount of a PARP inhibitor antineoplastic agent to the patient on days 5-12 and 19-25 or 3-12 and 17-25 of the treatment cycle.

15. The method of claim 14, wherein the PARP inhibitor is selected from the group consisting of niraparib, olaparib, veliparib, rucaparib and talazoparib.

16. The method of claim 15, wherein the therapeutically effective amount of the liposomal irinotecan is 70 mg/m² (free base) administered during a 90 minute infusion.

17. The method of claim 16, further comprising administering one or more subsequent 28-day treatment cycles of the antineoplastic therapy to the patient in the absence of disease progression or unacceptable toxicity during the prior treatment cycle of the antineoplastic therapy.

18. The method of claim 17, wherein the patient has been diagnosed with a cancer selected from the group consisting of: cervical cancer, ovarian cancer, triple negative breast cancer (TNBC), non-small cell lung cancer (NSCLC), small cell lung cancer (SCLC), gastrointestinal stromal tumors, gastric cancer, pancreatic cancer, colorectal cancer, and a neuroendocrine cancer.

19. The method of claim 18, wherein the patient does not have a BRCA1 or a BRCA2 mutation.

20. The method of claim 19, wherein each administration of the PARP inhibitor is administered at a dose of from about 20 mg/day to about 800 mg/day.

* * * * *